United States Patent
Blatter

(10) Patent No.: US 6,248,117 B1
(45) Date of Patent: Jun. 19, 2001

(54) ANASTOMOSIS APPARATUS FOR USE IN INTRALUMINALLY DIRECTED VASCULAR ANASTOMOSIS

(76) Inventor: Duane D. Blatter, 4220 Brockbank Way, Salt Lake City, UT (US) 84124

( * ) Notice: Subject to any disclaimer, the term of this patent is extended or adjusted under 35 U.S.C. 154(b) by 0 days.

(21) Appl. No.: 09/293,617

(22) Filed: Apr. 16, 1999

(51) Int. Cl.$^7$ .................................................. A61B 17/08
(52) U.S. Cl. ......................................... 606/153; 606/158
(58) Field of Search ................................... 606/167, 150, 606/151, 152, 153, 217, 219, 157, 158; 227/180.1, 175.1

(56) References Cited

U.S. PATENT DOCUMENTS

| | | |
|---|---|---|
| 4,018,228 | 4/1977 | Goosen . |
| 4,366,819 | 1/1983 | Kaster . |
| 4,523,592 | 6/1985 | Daniel . |
| 4,553,542 | 11/1985 | Schenck et al. . |
| 4,607,637 | 8/1986 | Berggren et al. . |
| 4,657,019 | 4/1987 | Walsh et al. . |

(List continued on next page.)

FOREIGN PATENT DOCUMENTS

| | | | |
|---|---|---|---|
| WO 97/12555 | 4/1997 | (WO) | ............................ A61B/17/11 |
| WO 98/06356 | 2/1998 | (WO) | ............................ A61F/2/06 |
| WO 98/19629 | 5/1998 | (WO) | ............................ A61F/2/06 |
| WO 98/19634 | 5/1998 | (WO) | ............................ A61F/2/06 |
| WO 99/11180 | 3/1999 | (WO) | ............................ A61B/17/11 |

OTHER PUBLICATIONS

Bass, Lawrence S. MD, and Michael R. Treat MD, Laser Tissue Welding: A Comprehensive Review of Current and Future Clinical Applications, Laser Surgery and Medicine Principles and Practice, 1996, pp. 381–415.

Boeckx, Willy D. MD, PhD, Scanning Electron Microscopic Analysis of the Stapled Microvascular Anastomosis in the Rabbit, http://198.76.172.231/cig–bin/bio/con/annals/atseq/63/S128/1997/ALL, Ann of Thorac Surgery, 1997, pp 63:S128–34.

(List continued on next page.)

*Primary Examiner*—Henry J. Recla
*Assistant Examiner*—Lien Ngo
(74) *Attorney, Agent, or Firm*—Workman, Nydegger & Seeley

(57) ABSTRACT

The present invention relates to new and useful apparatus for use with an intraluminally directed anvil apparatus for intraluminally directed vascular anastomosis of an end of a graft vessel to the wall of a receiving blood vessel that is performed according to a minimally invasive procedure. The intraluminally directed vascular anastomosis does not require the interruption of blood flow in the receiving blood vessel and it is versatile enough to suitably combine a variety of cutting, welding, soldering, sealing, and joining techniques such as stapling. The intraluminally directed anvil apparatus comprises an anvil and a wire used for signaling the optimal anastomosis site; this signaling can be performed when the initial exploration is performed. The intraluminally directed anvil apparatus is typically used with a catheter.

79 Claims, 38 Drawing Sheets

U.S. PATENT DOCUMENTS

| | | |
|---|---|---|
| 4,721,109 | 1/1988 | Healey . |
| 4,803,984 | 2/1989 | Narayanan et al. . |
| 4,819,637 | 4/1989 | Dormandy, Jr. et al. . |
| 4,846,186 | 7/1989 | Box et al. . |
| 4,848,367 | 7/1989 | Avant et al. . |
| 4,873,977 | 10/1989 | Avant et al. . |
| 4,907,591 | 3/1990 | Vasconcellos et al. . |
| 4,917,087 | 4/1990 | Walsh et al. . |
| 4,917,090 | 4/1990 | Berggren et al. . |
| 4,917,091 | 4/1990 | Berggren et al. . |
| 4,930,674 | 6/1990 | Barak . |
| 5,047,039 | 9/1991 | Avant et al. . |
| 5,047,041 | 9/1991 | Samuels . |
| 5,222,970 | 6/1993 | Reeves . |
| 5,254,113 | 10/1993 | Wilk . |
| 5,290,306 | 3/1994 | Trotta et al. . |
| 5,336,233 | 8/1994 | Chen . |
| 5,366,462 | 11/1994 | Kaster et al. . |
| 5,411,475 | 5/1995 | Atala et al. . |
| 5,456,712 | 10/1995 | Maginot . |
| 5,478,320 | 12/1995 | Trotta . |
| 5,478,354 | 12/1995 | Tovey et al. . |
| 5,522,834 | 6/1996 | Fonger et al. . |
| 5,613,979 | 3/1997 | Trotta et al. . |
| 5,616,114 | 4/1997 | Thornton et al. . |
| 5,620,649 | 4/1997 | Trotta . |
| 5,634,936 | 6/1997 | Linden et al. . |
| 5,662,580 | 9/1997 | Bradshaw et al. . |
| 5,662,700 | 9/1997 | Lazarus . |
| 5,690,662 | 11/1997 | Chiu et al. . |
| 5,695,504 | 12/1997 | Gifford, III et al. . |
| 5,702,412 | 12/1997 | Popov et al. . |
| 5,732,872 | 3/1998 | Bolduc et al. . |
| 5,766,158 | 6/1998 | Opolski . |
| 5,779,731 | 7/1998 | Leavitt . |
| 5,817,113 * | 10/1998 | Gifford, III et al. ................. 606/153 |
| 5,830,228 | 11/1998 | Knapp et al. . |
| 5,843,027 | 12/1998 | Stone et al. . |
| 5,860,992 | 1/1999 | Daniel et al. . |
| 5,861,005 | 1/1999 | Kontos . |
| 5,868,763 | 2/1999 | Spence et al. . |
| 5,893,369 | 4/1999 | LeMole . |
| 5,951,576 * | 9/1999 | Wakabayaski ........................ 606/151 |
| 5,976,178 * | 11/1999 | Goldsteen et al. ........................ 623/1 |

OTHER PUBLICATIONS

Boeckx, Willy D. MD, PhD, et al., Scanning Electron Microscopic Analysis of the Stapled Microvascular Anastomosi in the Rabbit, Ann Thorac Surg, 1997, pp. 63:S128–134.

Borst, Cornelius MD, Ph.D, et al., Minimally Invasive Coronary Artery Bypass Grafting: On the Beating Heart and via Limited Access, Ann Thorac Surg, 1997, pp. S1–S5.

Brittinger, Wolf Dieter et al., Vascular Access for Hemodialysis in Children, Pediatric Nephrology, 1997, pp. 11:87–95.

Cecchetti, W., et al., 980nm High Power Diode Laser in Surgical Applications, Biomedical Optical Instrumentation an Laser–Assisted Biotechnology, 1996, pp. 227–230.

Chikamatsu, Eiji MD, et al., Comparison of Laser Vascular Welding, Interrupted Sutures, and Continuous Sutures in Growing Vascular Anastomoses, Lasers in Surgery and Medicine, vol. 16, No. 1, 1995, pp. 34–40.

Cooley, Brian C. MD, Heat–induced Tissue Fusion for Microvascular Anastomosis, Microsurgery, vol. 17, No. 4, 1996 pp. 198–208.

Cope, Constantin and Stanley Baum, Catheters, Methods, and Injectors for Superselective Catheterization, Abrams' Angiography Vascular and Interventional Radiology, vol. 1, Fourth Edition, pp. 155–165.

D'Amelio, Frank D. et al., Fiber Optic Angioscopes, Novel Optical Fiber Techniques for Medical Applications, vol. 494, Aug. 21, 1984, pp. 44–51.

Deckelbaum, Lawrence I. MD, Cardiovascular Applications of Laser Technology, Laser Surgery and Medicine Principles and Practice, 1996, pp. 1–27.

Dumanian, G.A. MD et al., A New Photopolymerizable Blood Vessel Glue That Seals Human Vessel Anastomoses Without Augmenting Thrombogenicity, Plastic and Reconstructive Surgery, vol. 95, No. 5, Apr. 1995, pp. 901–907.

Dumitras, D.C. D.C.A. DUTU, Surgical Properties and Applications of Sealed–Off $CO_2$ Lasers, Biomedical Optical Instrumentation and Laser–Assisted Biotechnology, 1996, pp. 231–239.

Falciai, R. et al., Oxide Glass Hollow Fiber for $CO_2$ Laser Radiation Transmission, Novel Optical Fiber Techniques for Medical Applications, vol. 494, Aug. 21, 1984, pp. 84–87.

Gershony, Gary MD et al., Novel Vascular Sealing Device for Closure of Percutaneous Vascular Access Sites, Catherization and Cardiovascular Diagnosis, Sep. 1998, pp. 82–88.

Giele, Henk M.B.B.S., Histoacryl Glue as a Hemostatic Agent in Microvascular Anastomoses, Plastic and Reconstructive Surgery, vol. 94, No. 6, Nov. 1994, p. 897.

Goldman, Leon and W.A. Taylor, Development of a Laser Intravascular Fiber Optic Probe for the Treatment of Superficial Telangiectasia of the Lower Extremity in Man, Novel Optical Fiber Techniques for Medical Applications vol. 494, Aug. 21, 1984, pp. 76–83.

Gray, John L. MD et al., FGF–1 Affixation Stimulates ePTFE Endothelialization without Intimal Hyperplasia[1,2], Journal of Surgical Research Clinical and Laboratory Investigation, vol. 57, No. 5, Nov. 1994, pp. 596–612.

Greisler, Howard P. et al., Biointeractive Polymers and Tissue Engineered Blood Vessels, Biomaterials, vol. 17, No. 3, Feb. 1996, pp. 329–336.

Han, Seung–kyu MD, PhD et al., Microvascular Anastomosis with Minimal Suture and Fibrin Glue: Experimental and Clinical Study, Microsurgery, vol. 18, No. 5, 1998, pp. 306–311.

Haruguchi, Hiroaki et al., Clinical Application of Vascular Closure Staple Clips for Blood Access Surgery, ASAIO Journal, Sep.–Oct. 1998, pp. M562–564.

Humar, Abhinav MD et al., The Acutely Ischemic Extremity After Kidney Transplant: An Approach to Management, Surgery, Mar. 1998, pp. 344–350.

Jaber, Saad F. MD et al., Role of Flow Measurement Technique in Anastomotic Quality Assessment in Minimally Invasive CABG, Ann Thorac Surg, 1998, pp. 66:1087–1092.

Jones, Jon W. MD, A New Anastomotic Technique in Renal Transplants Reduces Warm Ischemia Time, Clinical Transplantation, 1998, 12:70–72.

Keskil, S. et al., Early Phase Alterations in Endothelium Dependent Vasorelaxation Responses Due to Aneurysm Clip Application and Related Manipulations, The European Journal of Neurosurgery, vol. 139, No. 1, 1997, pp. 71–76.

Kirschner, R.A. The Nd: YAG Laser—Applications in Surgery, Laser Systems for Photobiology and Photomedicine, 1991, pp. 53–56.

Kung, Robert T.V. PhD et al., Absorption Characteristics at 1.9 μm: Effect on Vascular Welding, Lasers in Surgery an Medicine, vol. 13, No. 1, 1993, pp. 12–17.

Lanzetta, M. MD, et al., Fibroblast Growth Factor Pretreatment of 1–MM PTFE Grafts, Microsurgery, vol. 17, No. 11, 1996, pp. 606–611.

Lisi, Gianfranco MD et al., Nonpenetrating Stapling: A Valuable Alternative for Coronary Anastomoses? Ann Thorac Surg 1998, 66, pp. 1705–1708.

Marek, Christopher A., BS et al., Acute Thrombogenic Effects of Fibrin Sealant on Microvascular Anastomoses in a Rat Model, *Annals of Plastic Surgery,* Oct. 1998, pp. 415–419.

Menovsky, Thomas MD et al., Use of Fibrin Glue to Protect Tissue During $CO_2$ Laser Surgery, The Laryngoscope, vol. 108, No. 9, pp. 1390–1393.

Mignani, A.G. and A.M. Scheggi, The Use of Optical Fibers in Biomedical Sensing, Laser Systems for Photobiology and Photomedicine, 1991, pp. 233–245.

Nataf, Patrick MD et al., Facilitated Vascular Anastomoses: The One Shot Device, Ann of Thorac Surg, 1998, pp. 66:1041–1044.

Nataf, Patrick MD, et al., Nonpenetrating Clips for Coronary Anastomosis, Ann Thorac Surg, 1997, pp. 63:S135–S137.

Nataf, Patrick MD, et al., Nonpenetrating Clips for Coronary Anastomosis, http://198.76.172.231/cgi–bin/bio/con/annals/atseq/63/S135/1997/ALL, Ann of Thorac Surg, 1997, pp. 63:S135–S137.

Nelson, Christine C. MD, et al., Eye Shield for Patients Undergoing Laser Treatment, American Journal of Ophthalmology, Series 3, vol. 110, No. 1, Jul. 1990, pp. 39–43.

Niemz, Markolf H. References, Laser–Tissue Interactions—Fundamentals and Applications, Springer, 1996, pp. 267–290.

Niemz, Markolf H. Interaction Mechanisms, Laser–Tissue Interactions—Fundamentals and Applications, Springer, 1996 pp. 45–47.

Niemz, Markolf H. Lasers in Angioplasty and Cardiology, Laser–Tissue Interactions—Fundamentals and Applications, Springer, 1996, pp. 216–221.

Papalois, V.E. et al., Use of Vascular Closure Staples in Vascular Access for Dialysis, Kidney and Pancreas Transplantation, International Surgery, Apr.–Jun. 1998, pp. 177–180.

Perkins, Rodney MD, Lasers in Medicine, Lasers Invention to Application, 1987, pp. 101–110.

Piano, Giancarlo MD et al., Assessing Outcomes, Costs, and Benefits of Emerging Technology for Minimally Invasiv Saphenous Vein In Situ Distal Arterial Bypasses, Archives of Surgery, Jun. 1998, pp. 613–618.

Pikoulis, Emmanouil MD, et al., Rapid Arterial Anastomosis with Titanium Clips, The American Journal of Surgery, Jun. 1998, pp. 494–496.

Poppas, Dix P. MD et al., Preparation of Human Albumin Solder for Laser Tissue Welding, Laser in Surgery and Medicine, vol. 13, No. 5, 1993, pp. 577–580.

Reardon, M. J. et al., Coronary Artery Bypass Conduits: Review of Current Status, The Journal of Cardiovascular Surgery, Jun. 1997, pp. 201–209.

Reichenspumer, Hermann MD, PhD et al., Minimally Invasive Coronary Artery Bypass Grafting: Port–Access Approach Versus Off–Pump Techniques, Ann of Thorac Surg, 1998, pp. 63:1036–1040.

Rouhi, A. Maureen, Contemporary Biomaterials, Chemical & Engineering News, vol. 77, No. 3, Jan. 1999, pp. 51–63.

Russel, D.A. et al., A Comparison of Laser and Arc–Lamp Spectroscopic Systems for In–Vivo Pharmacokinetic Measurements of Photosensitizers Used in Photodynamic Therapy, Laser Systems for Photobiology and Photomedicine 1991, 193–199.

Saitoh, Satoru MD and Yukio Nakatsuchi MD, Telescoping and Glue Technique in Vein Grafts for Arterial Defects, Plastic and Reconstructive Surgery, vol. 96, No. 6, Nov. 1995, pp. 1401–1408.

Sanbom, Timothy A. Laser Angioplasty, Vascular Medicine A Textbook of Vascular Biology and Diseases, pp. 771–787.

Schnapp, Lynn M. MD, Elmer's Glue, Elsie and You: Clinical Applications of Adhesion Molecules, The Mount Sinai Journal of Medicine, May 1998, pp. 224–231.

Self, Steven B. MD et al., Limited Thrombogenicity ofLow Temperature, Laser–Welded Vascular Anastomoses, Laser in Surgery and Medicine, vol. 18, No. 3, 1996, pp. 241–247.

Shennib, Hani MD et al., Computer–Assisted Telemanipulation: An Enabling Technology for Endoscopic Coronary Artery Bypass, Ann Thorac Surg 1998, pp. 66:1060–1063.

Shindo, Maisie L. MD et al., Use of a Mechanical Microvascular Anastomotic Device in Head and Neck Free Tissue Transfer, Archives of Otolaryngology–Head & Neck Surgery, May, 1996, pp. 529–532.

Shinoka, Toshiharu MD et al., Creation of Viable Pulmonary Artery Autografts Through Tissue Engineering, The Journal of Thoracic and Cardiovascular Surgery, Mar. 1998, pp. 536–546.

Spinelli, P. et al., Endoscopic Photodynamic Therapy: Clinical Aspects, Laser Systems for Photobiology and Photomedicine, 1991, pp. 149–155.

Stephenson, Jr., Edward R MD et al., Robotically Assisted Microsurgery for Endoscopic Coronary Artery Bypass Grafting, Ann of Thorac Surg, 1998, pp. 66:1064–1067.

Tulleken, Cornelis A.F. MD PhD, et al., Nonocclusive Excimer Laser–Assisted End–to–Side Anastomosis, Ann Thora Surg, 1997, pp. 63:S138–S142.

Tulleken, Cornelis A. F. MD, PhD, et al., Nonocclusive Excimer Laser–Assisted End–to–Side Anastomosis, http://198.76.172.231/cgi–bin/bio/con/annals/atseq/63/S138/1997/ALL, Ann Thorac Surg, 1997, pp. 63:S138–S142.

Turi, Zoltan G., MD et al., Plugging the Artery With a Suspension: A Cautious Appraisal, Catherization and Cardiovascular Diagnosis, Sep. 1998, pp. 90–91.

Underwood, M.J. et al., Autogenous Arterial Grafts for Coronary Bypass Surgery: Current Status and Future Perspectives, International Journal of Cardiology 46, 1994, pp. 95–102.

Viligiardi, R. et al., Excimer Laser Angioplasty in Human Artery Disease, Laser Systems for Photobiology and Photomedicine, 1991, pp. 69–72.

Weinschelbaum, Ernesto MD et al., Left Anterior Descending Coronary Artery Bypass Grafting Through Minimal Thoracotomy, Ann Throacic Surg, 1998, pp. 66:1008–1011.

Werker, Paul M.N. MD, Ph.D, et al., Review of Facilitated Approaches to Vascular Anastomosis Surgery, Ann Throa Surg; 1997, pp. S122–S127.

Zarge, Joseph I. MD et al., Fibrin Glue Containing Fibroblast Growth Factor Type 1 and Heparin Decreases Platelet Deposition, The American Journal of Surgery; Aug. 1997, pp. 188–192.

Jules S. Scheltes, Msc, et al., *Assessment of Patented Coronary End–to–Side Anastromotic Devices Using Micromechanical Bonding*, Ann Thorac Surg, 2000, pp. 218–221.

Ling Zhang, et al., *Venous Microanastomosis with the Unilink System, Sleeve, and Suture Techniques: A Comparative Study in the Rat*, Journal of Reconstructive Microsurgery, Vol. 13, No. 4, May 1997, pp. 257–262.

Web Page, *http://198.76.172.231/cgi–bin/bio/con/annuals/atseq/63/S122/1997 figs./5081f6*, The Microvascular Anastomotic System as marketed by the Medical–Surgical Division of 3M Health Care, The Society of Thoracic Surgeons, 1997.

\* cited by examiner

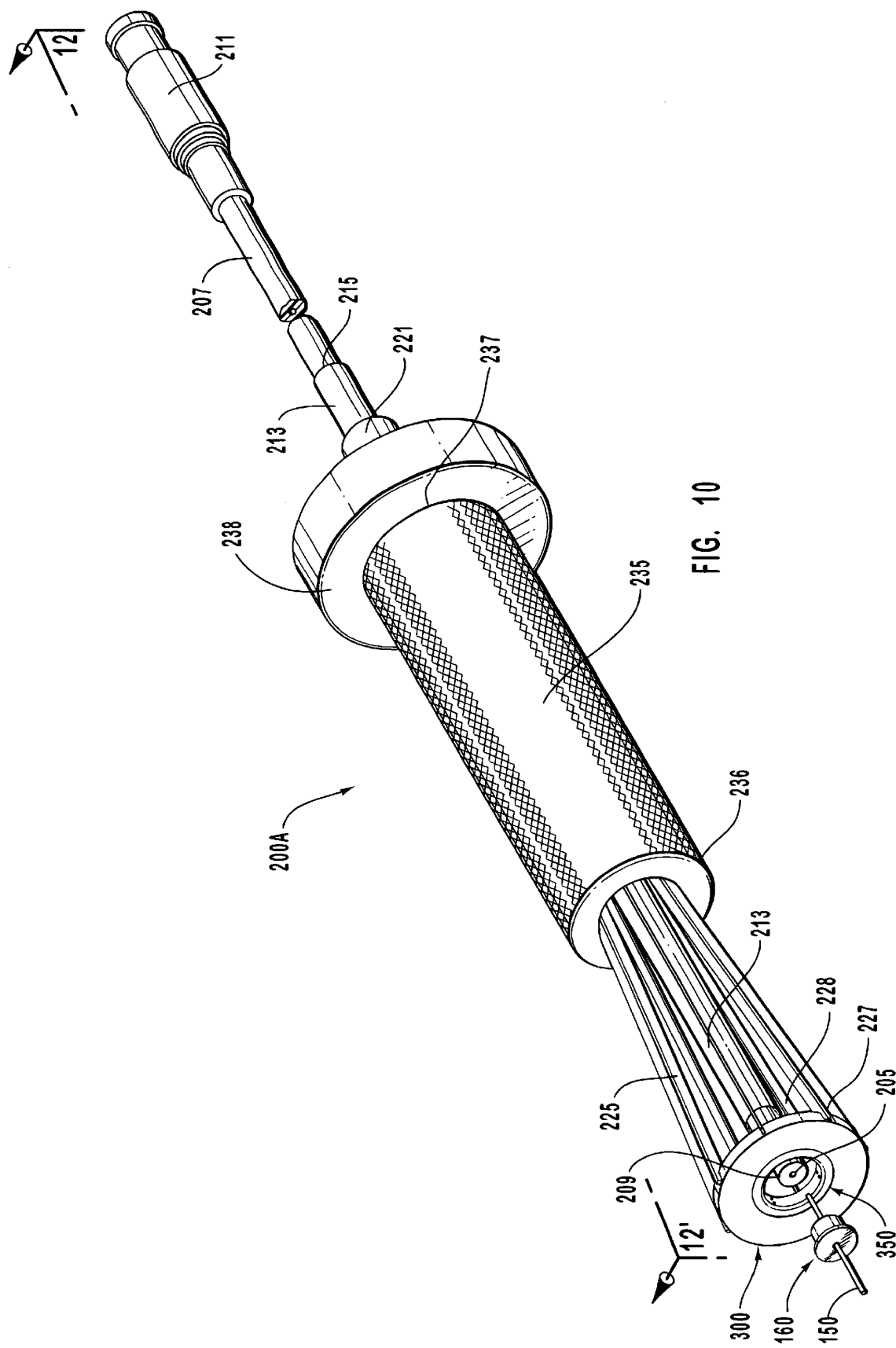

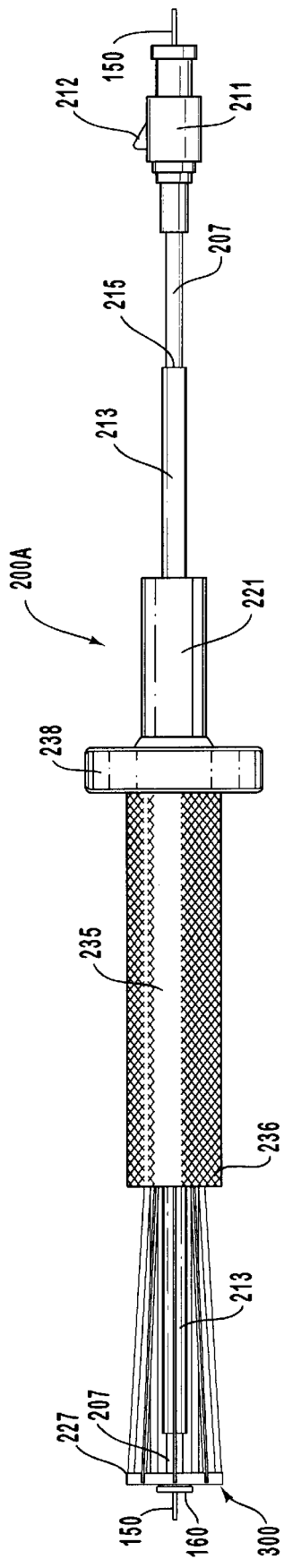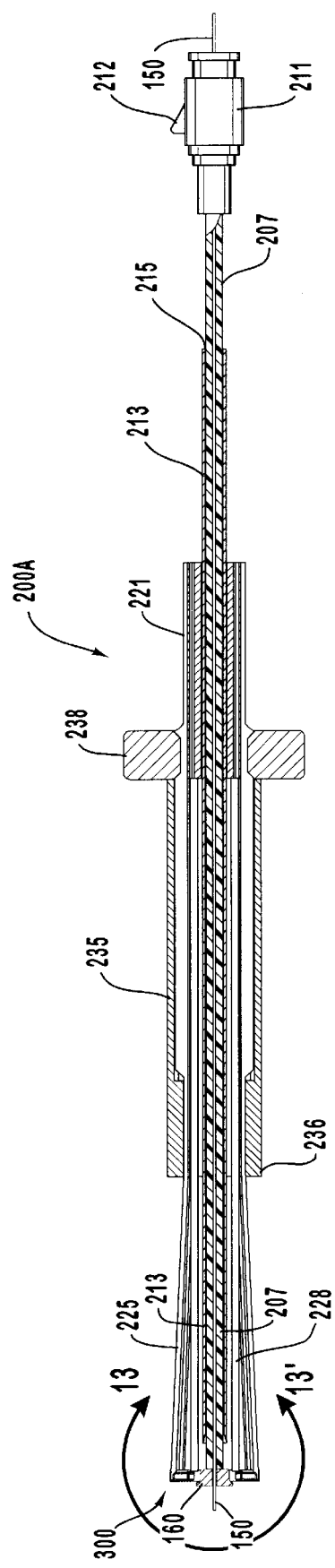
FIG. 11
FIG. 12

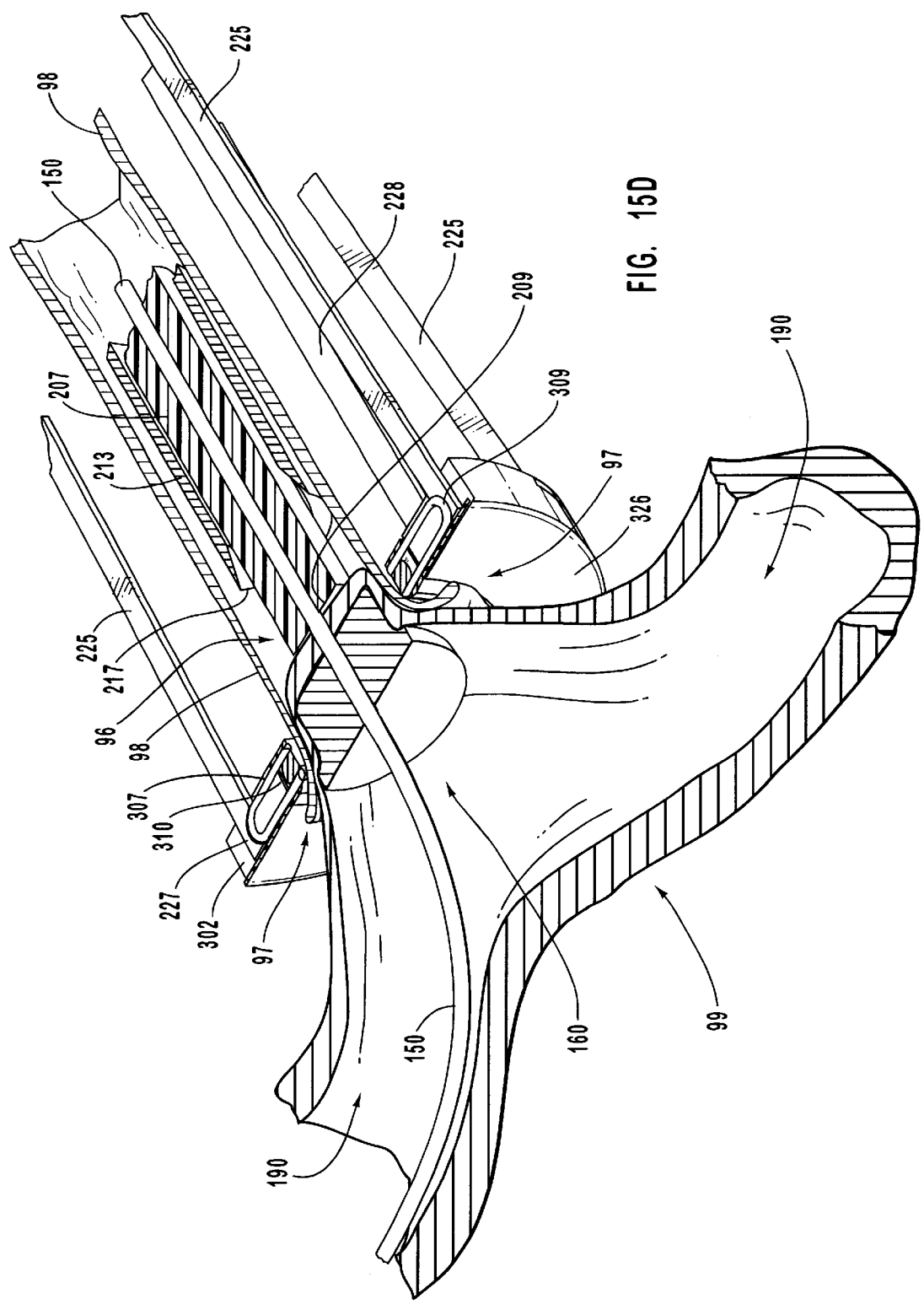

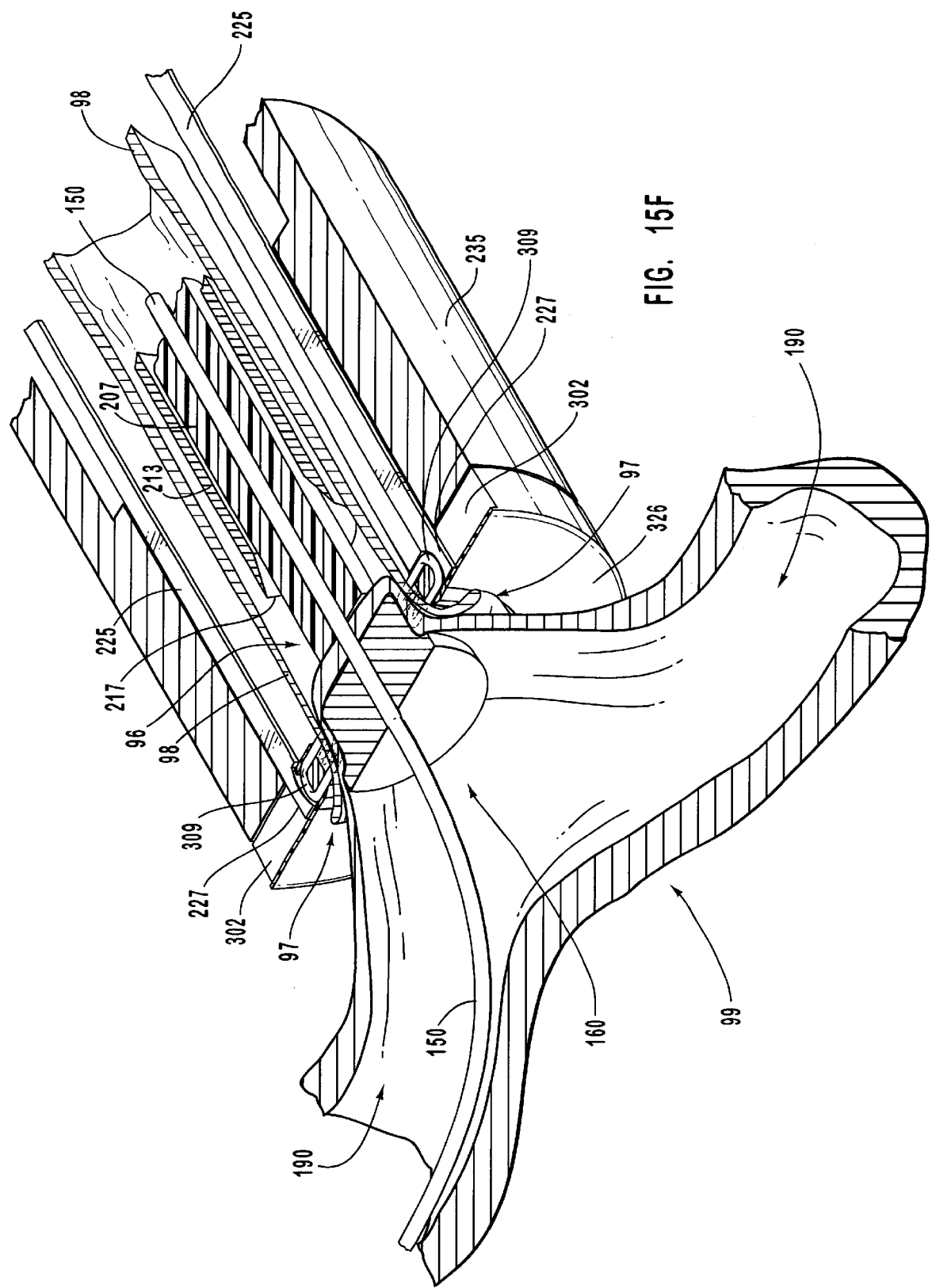

ANASTOMOSIS APPARATUS FOR USE IN INTRALUMINALLY DIRECTED VASCULAR ANASTOMOSIS

BACKGROUND OF THE INVENTION

1. The Field of the Invention

The present invention is directed generally to an anastomosis apparatus for use in intraluminally directed vascular anastomosis. More specifically the present invention is directed to an apparatus for attaching, and in particular for stapling, an end of a graft vessel to a wall of a blood vessel.

2. Relevant Technology

An endoscope is an instrument for the examination of the interior of a canal or hollow viscus. Most endoscopic procedures operate according to passive techniques, namely exploring and diagnosing. However, some endoscopic procedures have evolved so that they operate according to active or interventional procedures. In addition to exploring and diagnosing, active endoscopic procedures perform corrective tasks such as therapeutic and/or surgical tasks.

Active endoscopic procedures are highly effective because of a plurality of reasons. These reasons include: (a) minimal invasion of the patient's body; (b) reduced requirements of medical facilities and medical skill, and (c) quasi-simultaneity, if so desired, of the exploration, diagnosis, and corrective tasks.

For example, in merely a few hours, an active endoscopic technique such as a colonoscopy permits the exploration of the entire colon and rectum, the recording of selected images, the localization of abnormalities such as intestinal polyps, the removal of any polyp, and the extraction of any polyp for additional examination. If the colonoscopy had not been performed and any existing polyp had been left attached to the intestinal wall, such polyp might have become a malignant tumor thus giving rise to a perhaps lethal colorectal cancer. Such a colonoscopy is performed without the administration of general anesthesia. Furthermore, it is performed by a team that involves only a few health practitioners who do not necessarily have to be trained in the techniques that are required in surgical or other more invasive procedures.

The preceding characterization of active endoscopic procedures and the accompanying illustrative example aid in explaining why active endoscopic procedures enjoy great acceptance. This is because active endoscopic procedures lead to considerable savings in time and resources, they are minimally invasive, they can be repeatedly applied with minimal risk of undesirable side effects, and the corrective action may provide preventive effects that would otherwise be hard or even impossible to accomplish.

The foregoing description and characterization of active endoscopic procedures is intended to encompass the characteristics and advantages of peripheral techniques that do not necessarily require the use of an endoscope. Endoscopic applications are generally used in intracavity procedures such as intrathoracic and intraabdominal procedures. Peripheral techniques are usually employed in other body regions, such as arms and legs.

In short, it is a desirable goal to be able to provide by active endoscopic or peripheral procedures a variety of medical services that are currently provided by techniques that are more invasive and more demanding in time and in medical resources and skills. This goal is justified by the efficiency, effectiveness, safety, low cost, and preventive accomplishments of active endoscopic or peripheral procedures. In particular, this invention provides new methods and systems for performing vascular anastomoses by intraluminally directed active endoscopic or peripheral procedures. The intraluminally directed or intravascular part of the procedures of this invention is based on an examination performed by, for example, fluoroscopy, and extraluminal manipulation is performed endoscopically or according to a peripheral technique.

One aspect of this invention encompasses the quasi-simultaneity of the exploration, diagnosis and corrective tasks that can be achieved in vascular anastomoses performed by the intraluminally directed active endoscopic or peripheral procedures of this invention. Another aspect of this invention includes the minimally invasive character of the vascular anastomoses that are performed by the active endoscopic or peripheral procedures of this invention. These procedures are also characterized by comparatively reduced requirements of medical facilities and skill. To more effectively describe and enable the present invention, a review of some basic terminology and related technology is offered in the immediately following subsections.

2.1. Terminology

An anastomosis is an operative union of two hollow or tubular structures. Anastomotic structures can be part of a variety of systems, such as the vascular system, the digestive system or the genitourinary system. For example, blood is shunted from an artery to a vein in an arteriovenous anastomosis, and from the right pulmonary artery to the superior vena cava in a cavopulmonary anastomosis. In other examples, afferent and efferent loops of jejunum are joined in a Braun's anastomosis after gastroenteroscopy; the ureter and the Fallopian tube are joined in a ureterotubal anastomosis, and the ureter and a segment of the sigmoid colon are joined in a ureterosigmoid anastomosis. In microvascular anastomosis, very small blood vessels are anastomosed usually under surgical microscope.

An anastomosis is termed end-to-end when the terminal portions of tubular structures are anastomosed, and it is termed end-to-side when the terminal portion of a tubular structure is anastomosed to a lateral portion of another tubular or hollow structure. In an end-to-side anastomosis, we often refer to the structure whose end is anastomosed as the "graft vessel" while the structure whose side wall is anastomosed is referred to as the "receiving structure".

Anastomotic material typically includes autologous material, but it can also include heterologous material or synthetic material. An autologous graft is a graft in which the donor and recipient areas are in the same individual. Heterologous material is derived from an animal of a different species. The graft can be made of a synthetic material such as expanded polytetrafluoroethylene ("ePTFE"). Wolf Dieter Brittinger, Gottfried Walker, Wolf-Dieter Twittenhoff, and Norbert Konrad, *Vascular Access for Hemodialysis in Children, Pediatric Nephrology*, Vol. 11 (1997) pp. 87–95. When both ends of the graft are attached to a receiving structure, the configuration of the receiving structure with the anastomosed graft is called a bypass.

Depending on the anastomotic cross-section, anastomoses are termed bevelled or circular. In a bevelled anastomosis, the structures are joined in an oblique fashion, whereas in a circular anastomosis the structures are joined in a plane that is vertical with respect to the ultimate flow through the structures.

A nonocclusive anastomosis is typically an end-to-side anastomosis in which the flow of matter through the vessel that is anastomosed in its side is not interrupted while the anastomosis is performed. Most conventional techniques for vascular anastomosis require the interruption of blood flow through the receiving vessel while the anastomosis is performed.

Although the parts of a blood vessel are designated by well-known terms in the art, a few of these parts are briefly characterized here for introducing basic terminology. A blood vessel is in essence a tubular structure. In general, the region comprised within tubular walls, such as those defining a blood vessel or the walls defining the tubular member of an endoscope, is termed the lumen or the intraluminal space. A lumen that is not occluded is a patent lumen and the higher the patency of a blood vessel, the less disrupted the blood flow through such vessel is. A reduction of a blood vessel's patency can be caused by a stenosis, which is generally a stricture or narrowing of the blood vessel's lumen. A hyperplasia, or tissue growth, can also reduce a blood vessel's patency. Reduction of blood vessel patency, and in general a disruption in a vessel's blood flow, can lead to ischemia, which is a local lack of oxygen in tissue due to a mechanical obstruction of the blood supply.

A stent is a device that can be used within the lumen of tubular structures to assure patency of an intact but contracted lumen. Placement of a stent within an occluded blood vessel is one way of performing an angioplasty, which is an operation for enlarging a narrowed vascular lumen. Angioplasty and bypass are different ways for reestablishing blood supply, an operation that is called revascularization.

A blood vessel is composed of three distinct layers. From inside to outside, these layers include the intima, the media and the adventitia. The intima is a single layer of flat cells that collectively line the lumen. The media is a thick middle layer composed of smooth muscle cells. The adventitia is an outer layer that comprises fibrous covering.

Angiography is a technique for performing a radiography of vessels after the injection of a radio-opaque contrast material. This technique usually requires percutaneous injection of a radio-opaque catheter and positioning under fluoroscopic control. An angiogram is a radiograph obtained by angiography. Fluoroscopy is an examination technique with an apparatus, the fluoroscope, that renders visible the patterns of X-rays which have passed through a body under examination.

2.2 Related Technology

The operative union of two hollow or tubular structures requires that the anastomosis be tight with respect to the flow of matter through such structures and also that the anastomosed structures remain patent for allowing an uninterrupted flow of matter therethrough. For example, anastomosed blood vessels should not leak at the anastomosis site, the anastomotic devices should not significantly disrupt the flow of blood, and the anastomosis itself should not cause a biological reaction that could lead to an obstruction of the anastomosed blood vessels. In particular, anastomosed blood vessels should remain patent and they should ideally not develop hyperplasia, thrombosis, spasms or arteriosclerosis.

Because anastomosed structures are composed of tissues that are susceptible to damage, the anastomosis should furthermore not be significantly detrimental to the integrity of these tissues. For example, injury to endothelial tissue and exposure of subintimal connective tissue should be minimized or even eliminated in vascular anastomosis.

Because structures to be anastomosed are internal, an anastomosis requires a degree of invasion. The invasive character of an anastomosis, however, should be minimized subject to the reliable performance of a satisfactory anastomosis. Accordingly, there has been a noticeable trend during the last quarter of this century towards less invasive surgical intervention, a surgical style that is termed minimally invasive surgery. This style is characterized by pursuing a maximal treatment effect with minimal damage to surrounding and overlying normal structures. In addition, successful minimally invasive procedures should procure patency and they should minimize damage to the tissues of the anastomosed structures themselves.

A plurality of factors provide a propitious environment for this trend towards minimally invasive surgery. These factors include the development of high-technology diagnostic devices, the innate characteristics of human psychology and economic imperatives.

High-technology diagnostic devices such as flexible fiber-optic endoscopes and intravascular catheters have considerably enhanced our ability for performing a reliable spacio-temporal location of disease. More specifically, these devices permit the early and accurate determination of disease processes and their loci. Furthermore, it is known that the earlier a tumor or growth can be identified, the more responsive it is to therapy by a minimally invasive technique. See Rodney Perkins, *Lasers in Medicine in Lasers— Invention to Application*, edited by John R. Whinnery, Jesse H. Ausubel, and H. Dale Langford, p. 104, National Academy of Engineering, National Academy Press, Washington, D.C. 1987. (This work will hereinafter be referred to as "Lasers—Invention to Application"). See also Edward R. Stephenson, Sachin Sankholkar, Christopher T. Ducko, and Ralph J. Damiano, *Robotically Assisted Microsurgery for Endoscopic Coronary Artery Bypass Grafting, Annals of Thoracic Surgery*, Vol. 66 (1998) p. 1064. (This article will hereinafter be referred to as "Endoscopic Coronary Artery Bypass Grafting").

Human psychology also contributes to the growing trend towards minimally invasive techniques. This is attributed to the accepted prevailing preference of a minimally invasive technique with respect to a more invasive surgical technique whenever the outcomes of these two techniques are equivalent.

Finally, minimally invasive techniques are generally cost effective to insurers and to society in general because they are performed on an outpatient basis or else they require comparatively shorter hospitalization time. Furthermore, the less tissue is invasively effected in a procedure, the more likely it is that the patient will recover in a comparatively shorter period of time with lower cost hospitalization. Therefore, economic factors also favor the development of minimally invasive techniques because they can be performed with lower morbidity risk and they satisfy economic imperatives such as reduced cost and reduced loss of productive time. See Rodney Perkins in *Lasers—Invention to Application*, p. 104; *Endoscopic Coronary Artery Bypass Grafting*, pp. 1064, 1067.

Particularly in the field of vascular anastomosis, it is acknowledged that there is an increasing demand for an easier, quicker, less damaging, but reliable procedure to create vascular anastomosis. This demand is further revitalized by the movement of vascular procedures towards minimally invasive procedures. See Paul M. N. Werker and Moshe Kon, *Review of Facilitated Approaches to Vascular Anastomosis Surgery, Annals of Thoracic Surgery*, Vol. 63 (1997) pp. S122–S127. (This work will hereinafter be referred to as "Review of Facilitated Approaches to Vascular Anastomosis").

Conventional exploration and anastomosis techniques are not always implemented in such a way as to satisfy the demand for an easier, quicker, less damaging, but reliable vascular anastomosis. The following overview of conventional exploration and anastomosis techniques closes this background section on related technology.

Exploration of a blood vessel typically provides necessary information for locating and diagnosing vascular abnormalities such as those that reduce vascular patency. This exploration is usually performed with angiography, a procedure that detects vascular abnormalities fluoroscopically. When it is concluded that the appropriate corrective action requires an anastomosis, conventional procedures ordinarily follow a sequence in which the anastomosis is not performed at the time when the initial exploration and diagnostic are performed, but at a later time and in a typically different clinical setup. Accordingly, the time and resources that are spent during the exploration and diagnostic phases are not directly employed in the performance of an appropriate corrective action, such as an anastomosis.

By performing an anastomosis considerably after the initial exploration has taken place and in a different location and clinical environment, these conventional procedures also waste a significant part of the information acquired at the exploration phase. Images obtained during an angiographic procedure are typically recorded on film or digital medium. In current clinical practice, these recorded images are reviewed in a subsequent clinical setting and based upon a knowledge of external anatomy, the lesion location and optimal site for anastomosis are estimated. This process sacrifices potentially useful information. Fluoroscopic visualization is no longer available without repeating the angiogram procedure, and in conventional practice external anatomic localization is used in correlation with previously recorded images. In addition to this external inspection, conventional procedures could rely on imaging for determining the optimal anastomosis site when corrective action is taken. However, having to reacquire information leads to a waste of resources, it significantly increases the period of time from exploration to corrective action, it is an additional burden on the patient, and it enhances the invasive character of the treatment that is administered to the patient. Furthermore, reacquisition of information might have to be done in an environment that demands higher skills and more resources than they would have been otherwise needed. For example, the opening of a body cavity to expose the anatomical region around a potential anastomosis site, the determination of the optimal anastomosis site by external inspection, and the surgical performance of the anastomosis are part of a treatment that is more complex, requires practitioners with more training, and may be more time and resource consuming than the treatment provided by the methods, systems and apparatuses of the present invention.

Vascular anastomosis techniques can be classified in a plurality of groups. Although with various degrees of success, all these techniques generally intend to provide leak-proof joints that are not susceptible to mechanical failure, and they also intend to minimize damage and reduce the undesirable effects of certain operational features that may lead to post-anastomosis complications. Damage to be minimized and operational features whose undesirable effects should be reduced include endothelial coverage injury, exposure of subintimal connective tissue, exposure of an intraluminal foreign component, blood flow interruption, irregularities at the junction, adventitial tissue stripping, intimal injury, installment of a foreign rigid body, use of materials that may have toxic effects, damage to surrounding tissue, extensive vessel eversion, and tissue plane malalignment. Post-anastomosis complications include intimal hyperplasia, atherosclerosis, thrombosis, stenosis, tissue necrosis, vascular wall thinning, and aneurism formation. In addition, vascular anastomosis techniques are characterized by varying abilities to successfully cope with the dilating character of the structures to be anastomosed, their diversity in size, and the possibility that at least one structure may grow after the anastomosis has been performed. Other variables that partially determine the suitability of a specific anastomosis technique include the nature of the material to be anastomosed (for example, autologous, heterologous, or synthetic), the desired reduction in operative time, the skill requirements, and the healing time.

Each one of the techniques discussed hereinbelow for joining anastomosed structures presents a compromise for reducing undesirable effects in the practice of vascular anastomosis. High standards in one or a few aspects of the anastomosis can sometimes be achieved only at the expense of sacrificing what otherwise would have been the benefits of other aspects of the anastomosis.

Since early in the 20th century when vessel anastomoses were performed with an acceptable degree of reliability, the standard for creation of a vascular anastomosis has been manual suturing. *Review of Facilitated Approaches to Vascular Anastomosis*, p. S122. Suturing devices and methods are still being developed with the aim at performing less invasive surgical procedures within a body cavity. See, for example, U.S. Pat. No. 5,860,992 disclosing devices and methods for suture placement while performing less invasive procedures.

Regarding the application of sutures in vascular anastomoses, it has been generally reported that "the insertion of transmural stitches, even in experienced hands that employ atraumatic techniques and fine sutures, causes significant damage to the vessel wall. As the result of this the subendothelial matrix becomes exposed to the bloodstream and initiates the formation of a thrombus. The same process takes place at the actual site of the anastomosis in the case of intima-intima apposition. These processes are multifactorial but can cause obstruction of the complete anastomosis, especially in small vessels." *Review of Facilitated Approaches to Vascular Anastomosis*, p. S122. In addition to proximal occlusion, needle-and-suture-mediated intimal penetration is believed to represent a source of platelet emboli, which can cause distal embolization and thus a hazard in brain revascularization and myocardial circulation. Patrick Nataf, Wolff Kirsch, Arthur C. Hill, Toomas Anton, Yong Hua Zhu, Ramzi Ramadan, Leonardo Lima, Alain Pavie, Christian Cabrol, and Iradj Gandjbakhch, *Nonpenetrating Clips for Coronary Anastomosis, Annals of Thoracic Surgery*, Vol. 63 (1997) p. S137. (This article will hereinafter be referred to as "Nonpenetrating Clips for Coronary Anastomosis"). Furthermore, it is considered that "suture anastomosis of small vessels is time-consuming and tedious and demands a long and continuous training if high patency rates are to be regularly achieved." Willy D. Boeckx, Oliskevigius Darius, Bert van den hof, and Carlo van Holder, *Scanning Electron Microscopic Analysis of the Stapled Microvascular Anastomosis in the Rabbit, Annals of Thoracic Surgery*, Vol. 63 (1997) p. S128. (This work will hereinafter be referred to as "Microscopic Analysis of Stapled Microvascular Anastomosis"). In contrast, in all specialties that employ vascular surgery, "there is an increasing demand for a simple, time-saving, but reliable automated, semiautomated, or at least facilitated method to replace the process of manually sutured anastomosis. The most important reason for this demand is the movement of cardiac bypass surgery toward a minimally invasive and possibly even an endoscopic procedure." *Review of Facili-* tated *Approaches to Vascular Anastomosis*, p. S122. In this respect, improvement "may come from techniques that do not lead to exposure of [a] damaged vessel wall to the bloodstream." Id., p. S122.

Besides the group that includes techniques which rely on suturing, vascular anastomosis techniques can generally be classified in four groups depending on how the tissue is joined and on the type of device or material used for joining the tissue of the anastomosed vessels. These groups are: Stapling and clipping techniques, coupling techniques, pasting techniques, and laser techniques. Id., pp. S122–S127.

2.2.1. Stapling and Clipping Techniques

Although some staplers have been reported as providing leaky joints, a variety of staplers have been developed for end-to-end and for end-to-side anastomosis. U.S. Pat. No. 5,366,462 discloses a method of end-to-side vascular anastomosis. According to this method, the end of the graft blood vessel that is to be anastomosed is everted by 180°; one end of the staple pierces both vessels with punctures exposed to the blood flow and the other end of the staple pierces the outside of the receiving vessel. U.S. Pat. No. 5,732,872 discloses a surgical stapling instrument that comprises an expandable anvil for aiding in the stapling of a 180° everted end of a graft vessel to a receiving vessel. This patent also discloses a stapling instrument for joining the 180° everted second end of a graft vessel whose opposite end has already been anastomosed. To anastomose this second end, this technique requires clearance around the area in which the anastomosis is performed, exposure of the receiving blood vessel, external anatomic identification, and significant external manipulation in the open area around the anastomosis site. U.S. Pat. No. 4,930,674 discloses methods of end-to-end and end-to-side anastomosis and a surgical stapler that comprises a vessel gripping structure for joining the 180° everted end of a graft vessel to another vessel. U.S. Pat. No. 5,695,504 discloses methods and a system for performing an end-to-side vascular anastomosis, where the system is applicable for performing an anastomosis between a vascular graft and the ascending aorta in coronary artery bypass surgery, particularly in port-access coronary artery bypass graft surgery. This system includes a staple with a configuration that combines the functions of an anchor member and a coupling member into a one-piece anastomosis staple. U.S. Pat. No. 5,861,005 discloses an arterial stapling method and device for stapling an opening in an anatomical structure, whether the opening is deliberately formed or accidentally caused. This device employs a balloon catheter that helps positioning the stapling mechanism properly on the organ to be stapled.

Some stapling devices rely on access to the anastomosis area through an opening that might be as big as or comparable to typical openings that are required in surgical procedures. Furthermore, the 180° eversion of vessel ends is viewed as an operation that can be difficult, particularly in sclerotic vessels. *Review of Facilitated Approaches to Vascular Anastomosis*, p. S123.

In general, clipping techniques rely on arcuate legged clips for achieving a flanged, nonpenetrated, intimal approximation of the anastomosed structures. Reportedly, the use of clips leads to a biologically and technically superior anastomosis as compared to the penetrating microsuture. *Review of Facilitated Approaches to Vascular Anastomosis*, p. S123. By approximating the everted walls of the two vessels to be anastomosed, a clipping technique avoids stitching and reportedly the subsequent risk of intimal hyperplasia. Gianfranco Lisi, Louis P. Perrault, Philippe Menasché, Alain Bel, Michel Wassef, Jean-Paul Vilaine, and Paul M. Vanhoutte, *Nonpenetrating Stapling: A Valuable Alternative to Coronary Anastomoses, Annals of Thoracic Surgery*, Vol. 66 (1998) p. 1707. In addition, maintenance of an uninjured endothelial coverage and avoidance of exposure of subintimal connective tissue are considered important features because "regenerated endothelium presents selective dysfunction that may predispose to spasm and atherosclerosis, thereby affecting both medium-term and long-term graft patency" and the risk of thrombosis at the anastomotic site can be reduced. Id., p. 1707.

Nonpenetrating vascular closure staples ("VCS") have been used in anastomoses performed to provide access for dialysis, as well as in kidney and pancreas transplantation. It has been concluded in light of these anastomoses that "the fact that VCS staples are interrupted and do not disrupt the endothelium or have an intraluminal component makes them ideal" for achieving the goals of kidney transplantation. V. E. Papalois, J. Romagnoli, and N. S. Hakim, *Use of Vascular Closure Staples in Vascular Access for Dialysis, Kidney and Pancreas Transplantation, International surgery*, Vol. 83 (1998) p. 180. These goals include the avoidance of postoperative thrombosis and the avoidance of renal artery stenosis. As with kidney transplants, no anastomotic abnormalities were detected in pancreatic transplants, where the avoidance of arterial stenosis is also very important. Id., p. 180. The results of anastomoses performed for providing vascular access for dialysis were also reported successful. Id., p. 179. In addition, it has been reported that the "VCS applier is easy to manipulate, is as safe as hand-suture methods, and has time saving potential. VCS clips are useful for vascular anastomoses of blood access." Hiroaki Haruguchi, Yoshihiko Nakagawa, Yasuko Uchida, Junichiro Sageshima, Shohei Fuchinoue and Tetsuzo Agishi, *Clinical Application of Vascular Closure Staple Clips for Blood Access Surgery, ASAIO Journal*, Vol. 44(5) (1998) pp. M562–M564.

In a study of microvascular anastomosis of rabbit carotid arteries, some anastomosis were stapled using non-penetrating 0.9 mm microclips and some anastomosis were conventionally sutured. Arcuate-legged, nonpenetrating titanium clips are applied according to a clipping technique in an interrupted fashion to everted tissue edges at high compressive forces. It is considered that this technique "enables rapid and precise microvascular reconstructions, but requires both training and evertable tissue walls." *Nonpenetrating Clips for Coronary Anastomosis, Annals of Thoracic Surgery*, p. S135. An example of this clip applier is the VCS device, Autosuture, United States Surgical Corporation, Norwalk, Conn. *Nonpenetrating Clips for Coronary Anastomosis*, pp. S135–S137. U.S. Pat. No. 5,702,412 discloses a method and devices for performing end-to-side anastomoses where the side wall of one of the structures is cut from the intraluminal space of the graft vessel and the anastomosed structures can be secured by a plurality of clips or by suturing.

It has been concluded that stapled microvascular anastomosis is fast and reliable and histomorphologic examination of the anastomotic site revealed no major differences between sutured and stapled groups. *Microscopic Analysis of stapled Microvascular Anastomosis*, p. S128. Furthermore, it has also been reported that the "clipped anastomotic technique has a rapid learning curve, the same safety as suture methods, and the potential for facilitating endoscopic vascular reconstruction." *Nonpenetrating Clips for Coronary Anastomosis*, p. S135. In a study undertaken to compare VCS clips with sutured arterial end-to-end anastomosis in larger vessels, it was concluded that this type of anastomosis "can be performed more rapidly with VCS clips than continuous sutures", and that VCS clips "are potentially useful situations where the clamp time of the vessel is critical." Emmanouil Pikoulis, David Burris, Peter Rhee, Toshiya Nishibe, Ari Leppäniemi, David Wherry and Nonnan Rich, *Rapid Arterial Anastomosis with Titanium Clips, The American Journal of Surgery*, Vol. 175 (1998) pp. 494–496.

Nevertheless, clipping may lead to irregularities at the junction of the anastomosed vessels. In addition, it has been reported that "both periadventitial tissue stripping and microvascular clip application have deleterious effects in the early postoperative period" and that "temporary clips with a lesser width must be used in place of microvascular clips" while performing microvascular anastomosis. S. Keskil, N. Ceviker, K. Baykaner, Ö. Uluoğlu and Z. S. Ercan, *Early Phase Alterations in Endothelium Dependent Vasorelaxation Responses Due to Aneurysm Clip Application and Related Manipulations, Acta Neurochirurgica*, Vol. 139(1) (1997) pp. 71–76.

2.2.2. Coupling

Tissue bonding by coupling with the aid of devices such as stents, ferrules, or rings without staples is considered to be older than stapling. Among the more recent devices and techniques, U.S. Pat. No. 4,523,592 discloses anastomotic coupling means capable of end-to-end and end-to-side anastomosis without resorting to suturing. The vessels are coupled with a pair of coupling disc members that cooperatively lock and secure the everted tissue from the anastomosed structures. These everted tissues remain in intima-intima contact with no foreign material exposed to the lumen of the anastomosed vessels. U.S. Pat. Nos. 4,607,637, 4,917,090 and 4,917,091 also disclose the use of anastomosis rings and an instrument for joining vessels or tubular organs which are threaded to the annular devices before the joining. The instrument and the anastomosis rings are shaped and adapted to be utilized mainly in microsurgery. U.S. Pat. Nos. 4,657,019 and 4,917,087 disclose devices, kits and methods for non-suture end-to-end and end-to-side anastomosis of tubular tissue members that employ tubular connection members and provide intima-intima contact at the anastomosis site with no foreign material exposed to the lumen of the vessels being joined. An annuli pair that provides an anastomotic clamp and that is especially adapted for intraluminal disposition is disclosed in U.S. Pat. No. 5,336,233. Because of the intraluminal disposition, this device is exposed to the blood flow in the anastomosed vessels. U.S. Pat. No. 4,907,591 discloses a surgical instrument for use in the installation of an assembly of interlocking coupling members to achieve compression anastomosis of tubular structures. Other coupling devices include the use of intraluminal soluble stents and extraluminal glues, such as cyanoacrylates, for creating nonsuture anastomoses. Reportedly, 98% patency was obtained with these soluble polyvinyl alcohol stents. *Review of Facilitated Approaches to Vascular Anastomosis*, pp. S124–S125. An absorbable anastomotic device for microvascular surgery relies on the cuffing principle with injection-molding techniques using the polymer polyglactin. Vessel ends that are everted 180° are joined in this technique by an interconnecting collar so that an intima-intima seal is achieved. Reportedly, 96% patency was obtained with these absorbable interconnecting collars. *Review of Facilitated Approaches to Vascular Anastomosis*, p. S125.

The major advantage of a coupling microvascular anastomotic device has been reported to be the reduction in the time needed for a venous anastomosis, which decreases the total ischemic time. Maisie L. Shindo, Peter D. Constantino, Vincent P. Nalbone, Dale H. Rice and Uttam K. Sinha, *Use of a Mechanical Microvascular Anastomotic Device in Head and Neck Free Tissue Transfer, Archives of Otolaryngology—Head & Neck Surgery*, Vol. 122(5) (1996) pp.529–532. Although a number of coupling techniques do not place any foreign body in the intraluminal space of the anastomosed vessels, it is considered that the use of a foreign rigid body such as a ring that encloses a dynamically dilating structure is a disadvantage of this type of technique. Furthermore, this type of technique is viewed as not being flexible enough for its application to significant vessel size discrepancies in end-to-side anastomosis, and the devices are characterized as being of limited availability and needed in sets of different sizes. *Microscopic Analysis of stapled Microvascular Anastomosis*, p. S128. In addition, most coupling techniques require considerable eversion, incisions and mounting of the coupling devices that are difficult or impossible to apply endoscopically.

2.2.3. Adhesives

Pasting by applying adhesives or glues is widely employed in medicine. Several glues have been tested in anastomotic procedures, including fibrin glue, cyanoacrylic glues and photopolymerizable glues.

Fibrin glue is a biological two-component sealant comprising fibrinogen solution and thrombin combined with calcium chloride solution. These components are typically available deep-frozen in preloaded syringes, and they are mixed during application after thawing. Commercially available fibrin glue Tissucol has reportedly been approved by the Food and Drug Administration for use in the United States. See, Thomas Menovsky and Joost de Vries, *Use of Fibrin Glue to Protect Tissue During $CO_2$ Laser Surgery, Laryngoscope* Vol. 108 (1998) pp. 1390–1393. This article will hereinafter be referred to as "Fibrin Glue in Laser Surgery."

The use of fibrin glue has been found to be practical in telescoping anastomoses and in microanastomoses. Satoru Saitoh and Yukio Nakatsuchi, *Telescoping and Glue Technique in Vein Grafts for Arterial Defects, Plastic and Reconstructive Surgery*, Vol. 96(6) (1995) pp. 1401–1408, (this article will hereinafter be referred to as "Telescoping and Glue Technique"); Seung-Kyu Han, Sung-Wook Kim and Woo-Kyung Kim, *Microvascular Anastomosis With Minimal Suture and Fibrin Glue: Experimental and Clinical Study, Microsurgery*, Vol. 18(5) (1998) pp. 306–311, (this article will hereinafter be referred to as "Microvascular Anastomosis With Minimal Suture and Fibrin Glue"). In contrast, it has been reported that the application of thrombin-based fibrin sealant (fibrin glue) to microvascular anastomoses can have noticeable deleterious effects, particularly when used in venous anastomosis. Christopher A. Marek, Lester R. Amiss, Raymond F. Morgan, William D. Spotnitz and David B. Drake, *Acute Thrombogenic Effects of Fibrin Sealant on Microvascular Anastomoses in a Rat Model, Annals of plastic Surgery*, Vol. 41(4) (1998) pp. 415–419, (this article will hereinafter be referred to as "Thrombogenic Effects of Fibrin Sealant on Microvascular Anastomoses").

A biological procoagulant solution has been described as promising. The mixture contains bovine microfibrillar collagen and thrombin. Gary Gershony, John M. Brock and Jerry S. Powell, *Novel Vascular Sealing Device for Closure of Percutaneous Vascular Access Sites, Catheterization and Cardiovascular Diagnosis*, Vol. 45(1) (1998) pp. 82–88; Ted Feldman, *Percutaneous vascular Closure: Plugs, Stitches, and Glue, Catheterization and Cardiovascular Diagnosis*, Vol. 45(1) (1998) p. 89; Zoltan G. Turi, *Plugging the Artery With a Suspension: A Cautious Appraisal, Catheterization and Cardiovascular Diagnosis*, Vol. 45(1) (1998) pp. 90–91. (The immediately preceding three publications will hereinafter be referred to collectively as "Novel Vascular Sealing Device").

Cyanoacrylic glues tested on vessels include methyl cyanoacrylate and butyl cyanoacrylate, such as Histoacryl glue (butyl-2-cyanoacrylate). The ultra-violet polymerizable glue polyethyleneglycol 400 diacrylate has also been tested and reported that it "is able to effectively seal vessel puncture sites and anastomotic junctions without acutely augmenting local vascular thrombogenicity." G. A. Dumanian, W. Dascombe, C. Hong, K. Labadie, K. Garrett, A. S. Sawhney, C. P. Pathak, J. A. Hubbell and P. C. Johnson, *A new Photopolymerizable Blood Vessel Glue That Seals Human Vessel Anastomoses Without Augmenting Thrombogenicity, Plastic and Reconstructive Surgery*, Vol. 95(5) (1995) pp. 901–907, (this article will hereinafter be referred to as "Photopolymerizable Blood Vessel Glue").

Glues used in anastomotic practice face the challenges inherent to factors that include toxicity, thrombogenicity, vascular wall thinning, and mechanical strength of the joint. *Review of Facilitated Approaches to Vascular Anastomosis*, p. S125; Henk Giele, *Histoacryl Glue as a Hemostatic Agent in Microvascular Anastomoses, Plastic and Reconstructive Surgery*, Vol. 94(6) (1994) p. 897, (this work will hereinafter be referred to as "Histoacryl Glue as a Hemostatic Agent").

2.2.4. Lasers

Lasers have been used in angioplastic revascularization since about 1984. See for example, Markolf H. Niemz, *Laser Tissue Interactions*, pp. 216–221, Springer Verlag 1996, (this work will hereinafter be referred to as "Laser Tissue Interactions"); R. Viligiardi, V. Gallucci, R. Pini, R. Salimbeni and S. Galiberti, *Excimer Laser Angioplasty in Human Artery Disease, in Laser Systems in Photobiology and Photomedicine*, edited by A. N. Chester, S. Martellucci and A. M. Scheggi, pp. 69–72, Plenum Press, New York, 1991, (this work will hereinafter be referred to as "Excimer Laser Angioplasty in Human Artery Disease"); Timothy A. Sanbom, *Laser Angioplasty, in Vascular Medicine*, edited by Joseph Loscalzo, Mark A. Creager and Victor Brounwald, pp. 771–787, Little Brown Co., (this work will hereinafter be referred to as "Laser Angioplasty"). Whereas balloon angioplasty typically fractures, compresses or displaces plaque material, laser angioplasty typically removes plaque material by vaporizing it. Lawrence I. Deckelbaum, *Cardiovascular Applications of Laser Technology, in Laser Surgery and Medicine*, edited by Carmen A. Puliafito, pp. 1–27, Wiley-Liss, 1996, (this work will hereinafter be referred to as "Cardiovascular Applications of laser Technology").

The refinement of anastomosis techniques that rely on laser technology has been progressing since the reportedly first use of a neodymium yttrium-aluminum-garnet laser ("Nd-YAG laser") on vascular anastomosis in 1979. Particularly in an end-to-side vascular anastomosis, the end of a graft in the form of a tubular structure is connected to the side wall of a receiving vessel so that the anastomosed end of the graft encompasses the anastomosis fenestra, or artificial window, that has been formed into the side wall of the receiving vessel. Consequently, lasers can be used in anastomoses for welding the anastomosed structures and/or for opening the anastomosis fenestra. In addition to YAG lasers, such as Nd-YAG and Ho-YAG lasers, Excimer, diode, $CO_2$ and argon lasers have also been used in vascular anastomoses.

Laser welding has been defined as the process of using laser energy to join or bond tissues. Typically, laser welding relies on photothermal effects, but efforts are being made to develop laser welding that relies on photochemical effects, where the laser radiation activates cross-linking agents that are expected to produce stronger links than those produced by photothermal welding. Lawrence S. Bass and Michael R. Treat, *Laser Tissue Welding: A Comprehensive Review of Current and Future Clinical Applications, in Laser Surgery and Medicine*, edited by Carmen A. Puliafito, pp. 381–415. (This work will hereinafter be referred to as "Laser Tissue Welding").

Generally, the use of lasers in anastomotic practice faces the challenges inherent to factors that include the cost of laser purchase, maintenance and training, radiation damage to surrounding tissue, aneurism formation, the need for about three or four sutures (versus the nine or ten sutures applied in conventional anastomosis), side effects of heat-induced tissue welding, and mechanical failure at the anastomosis site. *Review of Facilitated Approaches to Vascular Anastomosis*, pp. S125–S126; *Laser Tissue Welding*, pp. 407–410; Brian C. Cooley, *Heat-Induced Tissue Fusion For Microvascular Anastomosis, Microsurgery*, Vol 17(4) (1996) pp. 198–208 (this article will hereinafter be referred to as "Heat-Induced Tissue Fusion For Microvascular Anastomosis"). It has been reported, however, that the "nonocclusive Excimer laser-assisted anastomosis technique is safe and yields a high long-term patency rate in neurosurgical patients" and that there might be indications for this method in coronary bypass surgery. Cornelis A. F. Tulleken, Rudolf M. Verdaasdonk, and Hendricus J. Mansvelt Beck, *Nonocclusive Excimer Laser-Assisted End-to-Side Anastomosis, Annals of Thoracic Surgery*, Vol. 63 (1997) pp. S138–S142. (This article will hereinafter be referred to as "Nonocclusive Excimer Laser-Assisted End-to-Side Anastomosis"). In addition, laser anastomosis is considered to offer moderately reduced operative time, reduced skill requirements, faster healing, ability to grow, and possibly reduced intimal hyperplasia. *Laser Tissue Welding*, pp. 407–410 (further reporting on selected microvascular anastomosis studies with lasers that include $CO_2$, argon, and diode lasers). Furthermore, research is being done to replace some of the initial laser sources by other lasers that are believed to be more suitable for clinical applications. For example, recent work with the 980 nm diode laser indicates that it may "replace in the near future laser sources of older conception such as the Nd-YAG." W. Cecchetti, S. Guazzieri, A. Tasca and S. Martellucci, 980 *nm High Power Diode Laser in Surgical Applications, in Biomedical Optical Instrumentation and Laser-Assisted Biotechnology*, edited by A. M. Verga Scheggi, S. Martellucci, A. N. Chester and R. Pratesi, pp. 227–230, Kluwer Academic Publishers, Dordrecht, The Netherlands, 1996. (This work will hereinafter be referred to as "980 nm High Power Diode Laser in Surgical Applications").

The $CO_2$ laser can seal blood vessels, including small blood vessels of about 0.5 mm in diameter or less and it has been used in microvascular anastomosis such as in human lympho-venous anastomosis. D. C. Dumitras and D. C. A. Dutu, *Surgical Properties and Applications of Sealed-off $CO_2$ Lasers, in Biomedical Optical Instrumentation and Laser-Assisted Biotechnology*, edited by A. M. Verga Scheggi, S. Martellucci, A. N. Chester and R. Pratesi, pp. 231–239, Kluwer Academic Publishers, Dirdrecht, The Netherlands, 1996. (This work will hereinafter be referred to as "Surgical Properties and Applications of Sealed-off $CO_2$ Lasers"). In addition to the $CO_2$ laser which is an efficient vaporizer of tissue, other lasers that effectively vaporize tissue include the argon and the KTP/532 lasers. *Lasers—Invention to Application*, p. 106.

The argon laser has been reported to offer advantages over conventional end-to-end anastomosis procedures applied to growing vessels. Eiji Chikamatsu, Tsunehisa Sakurai, Naomichi Nishikimi, Takashi Yano and Yuji Nimura, *Comparison of Laser Vascular Welding, Interrupted Sutures, and Continuous Sutures in Growing Vascular Anastomoses, Lasers in Surgery and Medicine*, Vol. 16(1) (1995) pp. 34–40. (This article will hereinafter be referred to as "Comparison of Laser Welding and Sutures in Vascular Anastomoses"). It has also been reported that low temperature argon laser welding limits anastomotic thrombogenicity, which is thought of as a factor that may improve early patency of venous and small arterial bypass grafts. Steven B. Self, Douglas A. Coe and James M. Seeger, *Limited Thrombogenicity of low Temperature Laser-Welded Vascular Anastomoses, Lasers in Surgery and Medicine*, Vol. 18(3) (1996) pp. 241–247, (this article will hereinafter be referred to as "Low Temperature Laser-Welded Vascular Anastomoses").

The use of lasers for medical purposes requires safety measures for protecting health care practitioners who handle the laser device and for shielding surrounding tissues and avoiding unintended radiation induced damage. Laser shield materials include layers of polymethylmethacrylate and tinfoil. See, Christine C. Nelson, Krystyna A. Pasyk and Gregory L. Dootz, *Eye Shield for Patients Undergoing Laser Treatment, American Journal of Ophthalmology* Vol. 110 (1990) pp. 39–43. Laser shield materials are known and they have been disclosed in a variety of sources such as Alex Mallow and Leon Chabot, *Laser Safety Handbook*, Van Nostrand Reinhold Co., New York (1978), and A. Roy Henderson, *A Guide to Laser Safety*, Chapman & Hall, London (1997). In particular, for example, the biological sealant fibrin glue can prevent severe damage to tissue when accidentally exposed to $CO_2$ laser radiation and intraoperative coating with fibrin glue can serve as a shield to protect arteries, veins, and nerves from accidental $CO_2$ laser exposure. Furthermore, it is considered that the use of fibrin glue for laser radiation protective processes "is especially attractive in . . . fields in which the glue is already used for sealing." *Fibrin Glue in Laser Surgery* at p. 1393.

2.2.5. Other Devices and Techniques

It is known that some anastomosis techniques combine different approaches. For example, biological glues that are based on proteins and other compounds are combined with laser radiation in laser soldering. "Laser soldering is a bonding technique in which a proteinaceous solder material is applied to the surfaces to be joined followed by application of laser light to seal the solder to the tissue surfaces." *Laser Tissue Welding*, pp. 389–392. Egg albumin, heterologous fibrin glue, and human albumin have been used as laser solders, also known as adjuvant materials for laser tissue welding. Dix P. Poppas, Theodore J. Choma, Christopher T. Rooke, Scott D. Klioze and Steven M. Schlossberg, *Preparation of Human Albumin Solder for Laser Tissue Welding, Lasers in Surgery and Medicine*, Vol. 13(5) (1993) pp. 577–580, (this article will hereinafter be referred to as "Human Albumin Solder for Laser Tissue Welding").

In an even newer technique, a chromophore is added to the solder to achieve photoenhancement effects that lead to an enhanced light absorption in the solder and not in the nontargeted tissue. Id., p. 391. In laser sealing, also known as laser-activated tissue sealing, sutured or stapled repairs are reinforced with laser solder, which is expected to provide "the strength and security of sutures and the watertightness of solder." Id., pp. 403–404.

The graft in a vascular anastomosis does not necessarily have to be an autologous blood vessel. In addition to ePTFE tubular grafts that have been referred to in a preceding subsection, several synthetic materials for vascular grafts have been used or are being developed.

Synthetic biomaterials that are being developed include polymeric materials with the proteins elastin and fibronectin. A. Maureen Rouhi, *Contemporary Biomaterials, Chemical & Engineering News*, Vol. 77(3) (1999) pp. 51–63.

ePTFE has been used with a variety of coatings. One type of coating includes fibrin glue that contains fibroblast growth factor type 1 and heparin. John L. Gray, Steven S. Kang, Gregory C. Zenni, Dae Un Kim, Petre I. Kim, Wilson H. Burgess, William Drohan, Jeffrey A. Winkels, Christian C. Haudenschild and Howard P. Greisler, *FGF*-1 *Affixation Stimulates ePTFE Endothelialization without Intimal Hyperplasia, Journal of Surgical Research*, Vol. 57(5) (1994) pp. 596–612; Joseph I. Zarge, Vicki Husak, Peter Huang and Howard P. Greisler, *Fibrin Glue Containing Fibroblast Growth Factor Type 1 and Heparin Decreases Platelet Deposition, The American Journal of Surgery*, Vol. 174(2) (1997) pp. 188–192; Howard P. Greisler, Claire Gosselin, Dewei Ren, Steven S. Kang and Dae Un Kim, *Biointeractive Polymers and Tissue Engineered Blood Vessels, Biomaterials*, Vol. 17(3) (1996) pp. 329–336. Another coating contains basic fibroblast growth factor in fibrin glue. M. Lanzetta, D. M. Crowe and M. J. Hickey, *Fibroblast Growth Factor Pretreatment of 1-mm PTFE Grafts, Microsurgery*, Vol. 17(11) (1996) pp. 606–611.

Other grafts comprise a synthetic biodegradable tubular scaffold, such as a vessel made of polyglactin/polyglycolic acid, that has been coated with autologous cells from a tissue culture. Toshiharu Shinoka, Dominique Shum-Tim, Peter X. Ma, Ronn E. Tanel, Noritaka Isogai, Robert Langer, Joseph P. Vacanti and John E. Mayer, Jr., *Creation of Viable Pulmonary Artery Autografts Through Tissue Engineering, The Journal of Thoracic and Cardiovascular Surgery*, Vol. 115(3) (1998) pp. 536–546.

A common feature of most conventional stapling, coupling and clipping techniques, particularly when applied to small-diameter vessels, is that they require a temporary interruption of the blood stream in the recipient vessel, a disruption that is thought to be not very well tolerated in cardiac bypass surgery. *Review of Facilitated Approaches to Vascular Anastomosis*, p. S126. In revascularization procedures of the brain, temporary occlusion of a proximal brain artery may cause brain ischemia, and consequently a non-occlusive anastomosis technique is required. *Nonocclusive Excimer Laser-Assisted End-to-Side Anastomosis*, p. 141. As the instrumentation that is needed at the anastomosis site becomes complex and cumbersome, a wider open area is needed for accessing the anastomosis site, thus leading to an increasingly invasive procedure. Furthermore, conventional anastomosis techniques are usually performed at a site that is determined by external observation of the affected area. This observation is performed at a time and in a medical setup that are different from the time and medical setup of a previous exploratory or diagnosis procedure.

Techniques that require the perforation of blood vessel tissue have raised concerns regarding intimal injury, adventitial stripping, tissue plane malalignment, and anastomotic bleeding. In addition, techniques that rely on devices that are exposed to the blood flow may lead to technical problems associated with a persistent intraluminal foreign body. These factors are thought to "contribute to both early and late anastomotic failure, particularly in the form of neointimal hyperplasia." *Nonpenetrating Clips for Coronary Anastomosis*, p. S135.

The need for completely endoscopic anastomosis procedures has been clearly expressed in the context of coronary artery bypass grafting. For example, it is currently acknowledged that "the goal of a completely endoscopic coronary artery bypass procedure has not yet been realized, and will require further technological advances." *Endoscopic Coronary Artery Bypass Grafting*, p. 1064. Furthermore, totally endoscopic coronary artery bypass grafting "is perceived by many as the ultimate surgical model of minimally invasive coronary artery bypass grafting". Hani Shennib, Amr Bastawisy, Michael J. Mack, and Frederic H. Moll, *Computer-Assisted Telemanipulation: An Enabling Technology for Endoscopic Coronary Artery Bypass*, Annals of Thoracic Surgery, Vol. 66 (1998) p. 1060.

Minimally invasive vascular grafting according to a peripheral procedure is equally desirable, and intraluminally directed minimally invasive active endoscopic or peripheral methods, systems and apparatuses are specially desirable. These methods, systems and apparatuses are specially desirable when, in particular, they are versatile enough as to be able to incorporate a plurality of the desirable features that have been discussed hereinabove while reviewing different groups of vascular anastomosis techniques. This desirability is consistent with the reported expectation that reliable methods for facilitated anastomosing of vessels will be developed by combining the best features of a variety of techniques. *Review of Facilitated Approaches to Vascular Anastomosis*, p. S126.

Each one of the afore-mentioned patents and publications is hereby incorporated by reference in its entirety for the material disclosed therein.

SUMMARY AND OBJECTS OF THE INVENTION

Conventional vascular anastomosis techniques do not rely on intraluminally directed active endoscopic or peripheral procedures. It is therefore desirable to provide methods, systems and apparatuses for their implementation as active endoscopic or peripheral procedures in vascular anastomosis.

An object of the present invention is to provide methods, systems, and apparatuses for performing a minimally invasive anastomosis by directly relying on the information acquired at the time of performing an initial angiographic exploration.

Another object of this invention is to provide methods, systems, and apparatuses such that the minimally invasive anastomosis is performed under a catheter assisted active endoscopic or peripheral procedure.

Additionally, another object of this invention is to provide methods, systems, and apparatuses to enable the performance of minimally invasive anastomoses that do not require the interruption of blood flow in the receiving blood vessel.

Still another object of the present invention is to provide methods, systems, and apparatuses that are versatile enough to be able to suitably combine a variety of cutting, welding, and joining techniques in the practice of vascular anastomosis.

A feature of the catheter assisted active endoscopic or peripheral procedure of this invention is that catheter assistance is provided following an intravascular approach. Accordingly, a catheter is inserted into and along the intraluminal space of a receiving blood vessel; characteristics of this catheter include its use for signaling the optimal anastomosis site at the time of performing an initial angiographic examination.

Another feature of the catheter assisted active endoscopic or peripheral procedure of this invention is that the minimally invasive anastomosis is performed with an extravascular endoscopic or peripheral device that is typically introduced percutaneously, and this is done in cooperation with an endovascular catheter. The extravascular device can be endoscopic or nonendoscopic. An extravascular endoscopic device is typically used in a procedure such as an intraabdominal or intrathoracic procedure, whereas a nonendoscopic extravascular device (hereinafter referred to as "peripheral device") is typically used when there is no need to use a visual aid, such as an endoscope, in a peripheral procedure.

One advantage of performing a minimally invasive anastomosis under the catheter assisted active endoscopic or peripheral procedure that is based on the methods, systems, and apparatuses of the present invention is that its practice does not require the same level of training in surgical methods and techniques that the practice of surgery requires. Cross-specialty teams of practitioners including those with training in endovascular intervention as well as conventional surgical training can consequently perform minimally invasive anastomoses according to the methods, apparatuses, and systems of this invention.

Another feature of the catheter assisted active endoscopic or peripheral procedure of this invention is that it directly employs information while it is being acquired in an angiographic examination. This efficient use of information, and in particular imaging, has the advantage that the anastomosis is actually performed in less time and without having to rely on the correlation of previously recorded images with external anatomic inspection for locating the optimal anastomosis site. The shorter procedure according to this invention consequently requires less or no hospitalization time and less medical resources.

Still another feature of the catheter assisted active endoscopic or peripheral procedure of this invention is that it requires no sutures, although it can be implemented in conjunction with suturing. The avoidance of sutures has the advantages of reducing the invasive character of the procedure, reducing the number of mechanical elements in the practice of the anastomosis, and shortening the time needed to perform the anastomosis.

By not requiring the interruption of blood flow in the receiving blood vessel, the catheter assisted active endoscopic or peripheral procedure of this invention advantageously reduces or even eliminates the risk of ischemia in organs that receive their main supply of blood through the receiving blood vessel. Furthermore, the exposure of the anastomosis area is reduced because no devices have to be introduced to temporarily interrupt blood flow. This feature advantageously enhances the minimally invasive character of the methods, systems, and apparatuses of this invention and the intervention time for the practice of the anastomosis.

The minimal disruption of blood flow in the receiving blood vessel by the catheter assisted active endoscopic or peripheral procedure of this invention advantageously makes it suitable in the context of coronary artery bypass grafting (CABG), whether blood circulation is intracorporeal or extracorporeal, and whether the grafting is performed on a beating heart or an arrested heart.

Another feature of the catheter assisted active endoscopic or peripheral procedure of this invention is the efficient use of information and the simpler procedural and technical approach relative to more invasive procedures. This feature advantageously permits the reduction in the number of practitioners involved in the anastomosis and consequently enhances the consistency of the results, which become less operator-dependent.

The methods, systems, and apparatuses of this invention enable the performance of minimally invasive vascular anastomosis following a diagnostic catheter angiogram. The anastomosis is preferably performed according to this procedure by inserting a catheter into and along the intraluminal space of a receiving blood vessel while an angiographic examination is taking place. The catheter distal end is intravascularly placed at the optimal anastomosis site and this site is signaled with the aid of one of the catheter's features.

In a preferred embodiment, the anastomosis site is signaled with a mechanical device such as a catheter wire that has an anvil attached to it. The distal end of the catheter wire is pushed along one of the catheter lumens so the wire's distal end pierces the wall of the receiving blood vessel from the intima outward through the media and adventitia. At the same time, a device such as an intravascular anvil that is attached to the catheter wire abuts the wall of the receiving blood vessel at the anastomosis site, shaping the abutted portion of the wall at the site where the anastomosis fenestra will be opened.

An endoscopic or peripheral device preferably carries the graft vessel and engages the extravascular portion of the catheter wire in such a way that the distal end of the graft vessel is brought into contact with the abutted portion of the outer wall of the receiving blood vessel. The anastomosis fenestra is subsequently cut and the graft vessel is joined to the receiving blood vessel.

As discussed in more detail hereinbelow, the opening of the anastomosis fenestra can be performed mechanically or with the aid of a radiation-based device. In addition, the graft vessel is joined to the outer wall of the receiving blood vessel by any one among a variety of techniques and combinations thereof. These techniques include clipping, stapling, suturing, welding, soldering, and gluing. Moreover, the signaling of the anastomosis site is preferably performed with the aid of a mechanical device such as the combination of a catheter wire and an anvil.

A feature of the catheter assisted endoscopic or peripheral procedure of this invention is the versatility of the intravascular catheter and of the extravascular device for signaling the anastomosis site and cooperatively performing the anastomosis. Accordingly, a variety of devices and techniques can be advantageously combined in the context of this invention to enhance the performance of its methods, systems and apparatuses.

To achieve the foregoing objects, and in accordance with the invention as embodied and broadly described herein, the present invention relates to new and useful apparatuses, systems and methods for performing vascular anastomosis.

These and other objects and features of the present invention will become more fully apparent from the following description and appended claims, or may be learned by the practice of the invention as set forth hereinafter.

BRIEF DESCRIPTION OF THE DRAWINGS

In order to more fully understand the manner in which the above-recited and other advantages and objects of the invention are obtained, a more particular description of the invention will be rendered by reference to a specific embodiment thereof which is illustrated in the appended drawings. Understanding that these drawings depict only a typical embodiment of the invention and are not therefore to be considered to be limiting of its scope, the invention in its presently understood best mode for making and using the same will be described and explained with additional specificity and detail through the use of the accompanying drawings in which:

FIG. 10 is a schematic perspective view of the embodiment of the peripheral device shown in FIG. 8 in an assembled configuration.

FIG. 11 shows a side view of the embodiment shown in FIG. 10.

FIG. 12 is a longitudinal cross sectional view of the embodiment shown in FIG. 11 along plane 12.

FIG. 15D is a cut away perspective view of an end of the peripheral device shown in FIG. 15C holding the graft vessel in contact with the receiving vessel at the anastomosis site.

FIG. 15F is a perspective view like the view shown in FIG. 15D at another stage in the process of attaching the graft vessel to the receiving blood vessel.

DETAILED DESCRIPTION OF THE PREFERRED EMBODIMENTS

The present invention relates to systems, methods and apparatuses for intraluminally directed active endoscopic or peripheral procedures, and more particularly to systems, methods and apparatuses for performing intraluminally directed minimally invasive vascular anastomosis.

In contrast to conventional procedures, this invention provides for the direct utilization of the information acquired during an initial angiographic exploration in the actual creation of an anastomosis. Accordingly, this invention enables the determination of an optimal anastomosis site with the information acquired during the initial exploration and provides for an active endoscopic or peripheral technique for performing a minimally invasive anastomosis immediately following the initial angiographic exploration and in the same clinical environment. Minimally invasive anastomosis according to this invention is performed with an integrated method and system that relies on intraluminally directed active intervention and active endoscopic or peripheral intervention.

Figure 1:
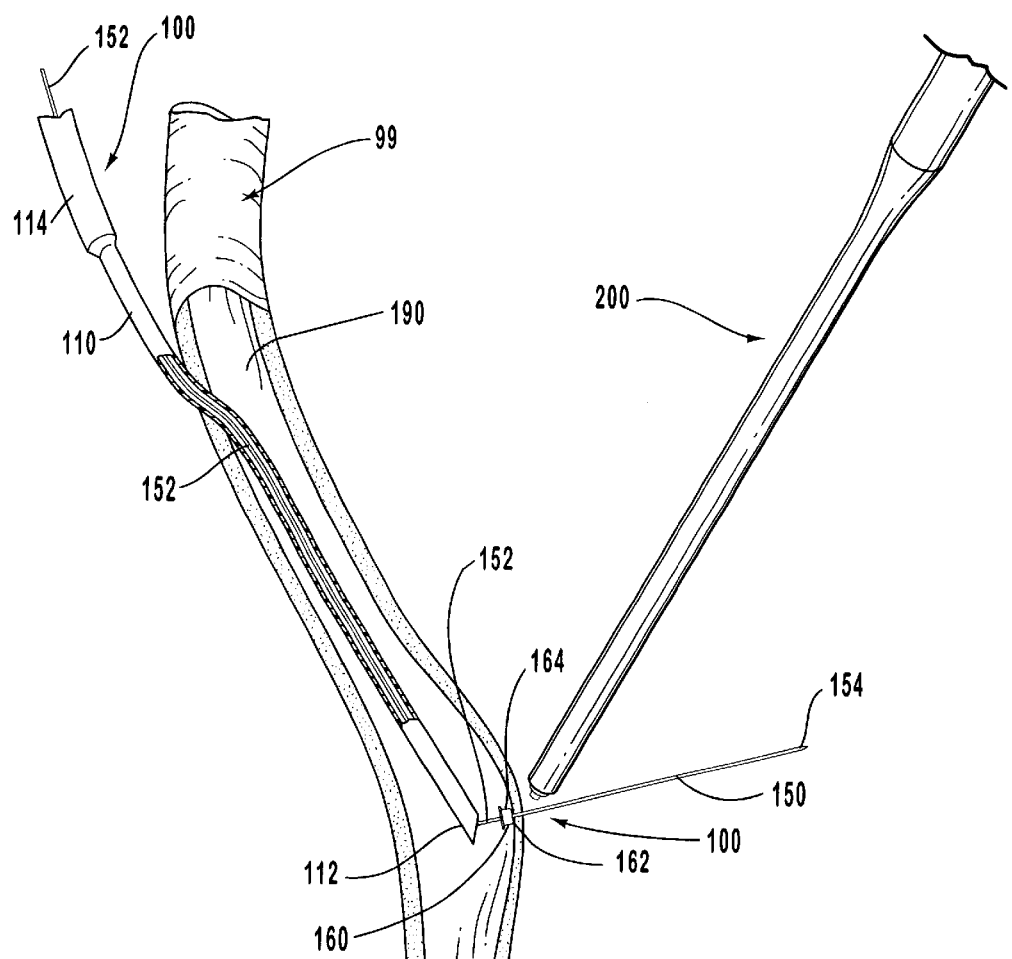
FIG. 1 is a partially cut-away view of the general disposition of the intraluminally directed anvil apparatus, wire and endoscopic or peripheral device of this invention.

As schematically shown in FIG. 1, an anastomosis according to this invention is performed at a site that is signaled with the aid of an imaging technique and an intraluminally directed anvil apparatus that is embodied in this Figure by catheter apparatus 100. In FIG. 1, the anastomosis is performed with an anastomosis device shown at 200 that generically and exemplarily represents an embodiment of an extravascular device, whether endoscopic or peripheral device. Anastomosis device 200 is operated in conjunction with an intraluminally directed anvil apparatus, such as catheter apparatus 100.

Specific examples of embodiments of the intraluminally directed apparatus and of anastomosis device 200 are given and discussed hereinbelow. More specifically, FIGS. 2–7 are directed to features of the intraluminally directed anvil apparatus; FIGS. 8–22I show different views of structural and operational features of different embodiments of the anastomosis device.

Intraluminally Directed Anvil Apparatus

In one exemplary embodiment of this invention, the intraluminally directed anvil apparatus is embodied by catheter apparatus 100. Catheter apparatus 100 comprises tubular shaft 110, positioning wire or stem 152, anvil 160, and piercing wire 150. This embodiment of the intraluminally directed anvil apparatus is referred to as a catheter apparatus. Other embodiments of the intraluminally directed anvil apparatus without a tubular shaft such as that shown at 110, however, are disclosed herein. These embodiments are also utilized to signal the location of an anastomosis site and to form an anastomosis in conjunction with an anastomosis device.

Distal end 112 of tubular shaft 110 can be percutaneously introduced in the intraluminal space 190 of receiving blood vessel 99 according to conventional catheterization techniques. Catheterization techniques are described, for example, by Constantin Cope and Stanley Baum, *Catheters, Methods, and Injectors for Superselective Catheterization*, in *Abrams' Angiography*, edited by Stanley Baum, 4th ed. (This work will hereinafter be referred to as "Catheters, Methods, and Injectors", and it is hereby incorporated by reference in its entirety). Tubular shaft 110 is inserted along intraluminal space 190 until distal end 112 reaches the proximity of a blood vessel occlusion or another abnormality that has been detected by a conventional exploration technique. With tubular shaft 110 so disposed, piercing wire 150 is introduced into tubular shaft 110 through proximal end 114 and it extends along tubular shaft 110. Piercing wire 150 is inserted within and along tubular shaft 110 of catheter apparatus 100 so that distal piercing end 154 punctures receiving blood vessel 99 from its intraluminal space and it extends outwardly by protruding at the optimally chosen anastomosis site. To facilitate this operation, distal end 154 is preferably sharp enough as to be able to puncture the wall of receiving blood vessel 99 from its intima outwards without causing undue tearing around the puncture.

Piercing wire in the context of this invention, and in particular when referring to piercing wire 150, refers to any thin and elongated device that is used for penetrating the wall of a blood vessel. A guidewire suited for inserting both diagnostic and therapeutic catheters is disclosed in U.S. Pat. No. 4,846,186, which is hereby incorporated by reference in its entirety, and catheters and guidewires for vascular and interventional radiology are disclosed in Catheters, Methods, and Injectors, at 155-174, references which are hereby incorporated by reference in their entirety. Piercing wire 150, however, is preferably pointed and sharp to effectively puncture the wall of receiving blood vessel 99.

In the embodiment shown in FIG. 1, piercing wire 150 extends from anvil 160 and positioning wire 162 extends also from anvil 160, but opposite to piercing wire 150. The combined length of piercing wire 150 and positioning wire 152 varies depending on the separation between the insertion site of catheter apparatus 100 and the anastomosis site. For example, this combined length would be approximately 180 cm long, depending on the patient's height, if an anastomosis were to be performed in a blood vessel in the arm such as the brachial artery, and catheter apparatus 100 were inserted into the femoral artery.

Figure 2A:
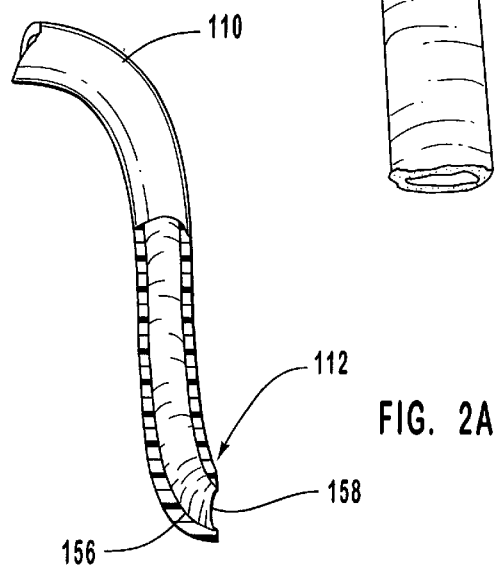
FIG. 2A is a partial cut-away view of one of the ends of the catheter shown in FIG. 1.
Figure 2B:
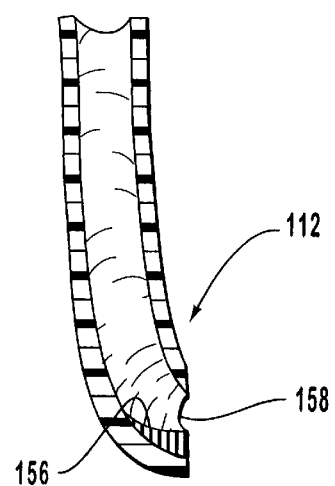
FIG. 2B is a partial cut-away view of another embodiment of one of the ends of the catheter depicted in FIG. 1.

Distal end 112 can be modified as shown in FIG. 2 to provide a lateral exit to distal end 154 of piercing wire 150. In one embodiment of catheter apparatus 100, shown in FIG. 2B, distal end 112 comprises deflecting surface 156 and lateral aperture 158 that guide distal end 154 of piercing wire 150 towards the intima of receiving blood vessel 99. Because distal end 154 is very sharp, deflecting surface 156 is preferably a puncture and abrasion resistant surface. In addition, distal end 112 can be provided with an appropriate marker for imaging the orientation of the aperture at distal end 112 and/or the position of distal end 112 itself. Such radio-opaque markers can be any of the radio-opaque markers known in the practice of angiography. Piercing wire 150 is typically radio-opaque itself, although very thin embodiments of this wire are preferably coated with a material such as gold or barium to make them more visible. Catheter distal end configurations for directing outwardly an elongated member have been disclosed in US Pat. Nos. 4,578,061, 4,861,336, 5,167,645, 5,342,394, and 5,800,450, which are hereby incorporated by reference in their entirety.

Figure 3A:
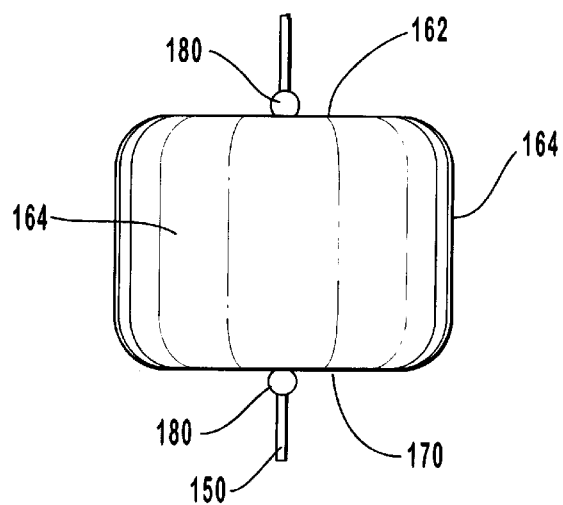
FIG. 3A shows an embodiment of the anvil of this invention that is attached to the wire with the aid of two stoppers.

In a preferred embodiment, the intraluminally directed anvil apparatus, such as catheter apparatus 100, comprises an anvil that is placed in intraluminal space 190. The anvil in this invention is preferably fixed to piercing wire 150 at its proximal end. Alternatively, the anvil of this invention could be slidably mounted on and around piercing wire 150, in which case piercing wire 150 and positioning wire 152 are typically an integral wire. In one exemplary embodiment of the intraluminally directed anvil apparatus, the anvil of this invention is embodied by anvil 160 that is integrally attached to and around piercing wire 150. Anvil 160 can also be attached to piercing wire 150 with the aid of any other fastening device or devices that retain anvil 160 in a fixed position relative to piercing wire 150, whether this wire is inserted into or extracted from intraluminal space 190. Stoppers 180 shown in FIG. 3A are an exemplary embodiment of fastening devices that facilitate the effective pushing on anvil 160 as positioning wire 152 and piercing wire 150 are inserted through proximal end 114 of tubular shaft 110 and facilitate also the extraction of anvil 160 as positioning wire 152 is pulled out, thus extracting piercing wire 150 through proximal end 114 of tubular shaft 110.

The anvil of this invention provides a receiving surface, such as receiving surface 162 of anvil 160, destined to be in direct contact with the blood vessel's intima at the anastomosis site when the anvil abuts the receiving blood vessel wall. Anvil 160 is sized so that it can slide within the lumen of tubular shaft 110 while presenting a receiving surface 162 that has an area approximately matched to the cross-sectional area of the lumen of the graft blood vessel. Anvil 160 and particularly receiving surface 162 are preferably made of a puncture resistant material that can withstand the abrasive action of the pointed end of a device that bends upon having its pointed end deflected by receiving surface 162. For example, anvil 160 is preferably made of stainless steel when it is to withstand the abrasive action of a cutting device or of a sharp pointed end. When cutting of the anastomosis fenestra is made with radiant energy, the anvil of this invention is preferably coated with radiation absorbing material that prevents radiation scattering. Such coated anvil embodiments are hereinafter referred to as a "laser shield anvil". In addition, the anvil of this invention does not have to be puncture resistant when the anastomosed structures are joined in a way that does not require staples, such as clipping, gluing, welding or soldering. This embodiment of the anvil of this invention is hereinafter referred to as a "soft anvil".

In one embodiment of this invention, the anvil is made of expandable material so that the deflated anvil can optionally be moved within and along catheter apparatus 100 and it can be inflated at the anastomosis site. This embodiment of the anvil of this invention is hereinafter referred to as "balloon anvil". A coating of laser shield material can be incorporated particularly at the receiving surface of the anvil of this invention. One example of a laser shield material is a shield consisting of a sandwich of polymethylmethacrylate and tinfoil that is known to provide corneal and retinal protection from inadvertent injury during argon, Nd-YAG or dye laser treatment at the tested laser power outputs.

In one embodiment of this invention, receiving surface 162 is destined to provide a stopping surface for a cutting blade and deflecting surface 164 of anvil 160 is destined to receive the ends of staples that bend upon being deflected by deflecting surface 164. Deflecting surface 164 and receiving surface 162 can in some embodiments of anvil 160 be differentiated as two parts of anvil 160, whereas in some embodiments deflecting surface 164 is a continuation of receiving surface 162. The terms "receiving surface" and "deflecting surface" will collectively refer to the surface of anvil 164. The constituent materials and/or the features of receiving surface 162 are preferably different from those of deflecting surface 164 when the anvil of this invention is embodied, for example, by a balloon anvil. In other embodiments of this invention, however, receiving surface 162 and deflecting surface 164 are made of the same materials and/or have similar features.

Figure 3B:
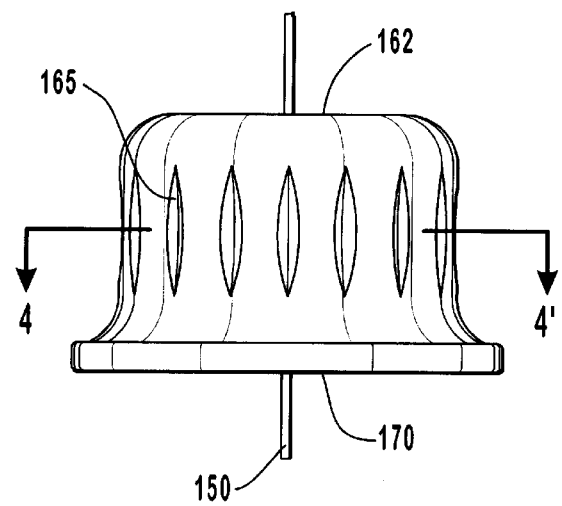
FIG. 3B shows another embodiment of the anvil of this invention that is integrally attached to the wire and has concave side features on its surface.
Figure 3C:
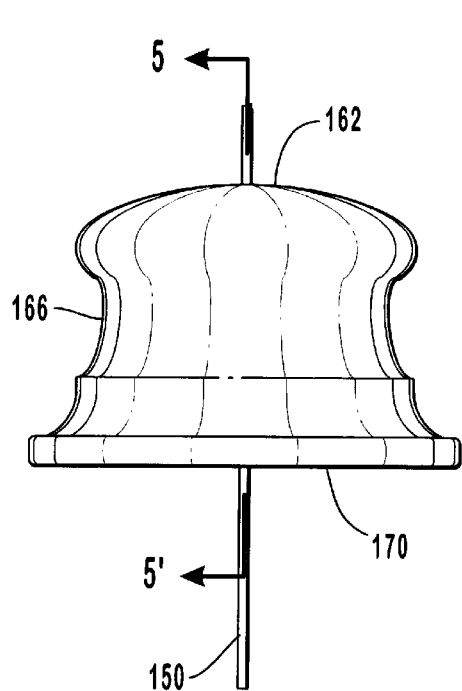
FIG. 3C shows another embodiment of the anvil of this invention that is integrally attached to the wire and has side surface features for bending staples or clips.
Figure 3D:
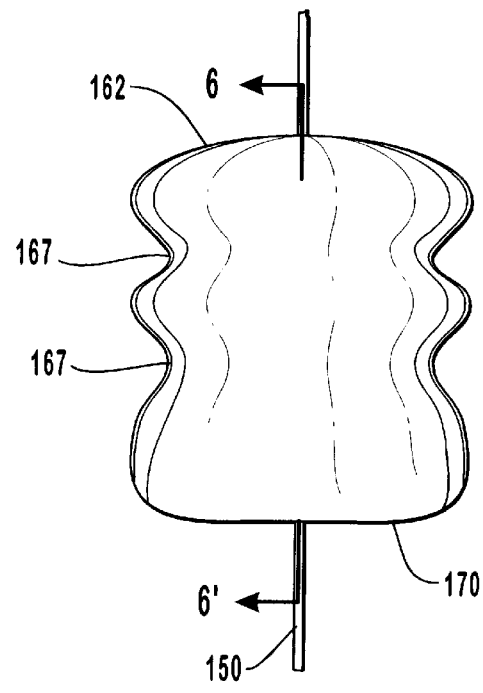
FIG. 3D shows another embodiment of the anvil of this invention that is integrally attached to the wire and has another set of side surface features for bending staples or clips.
Figure 4:
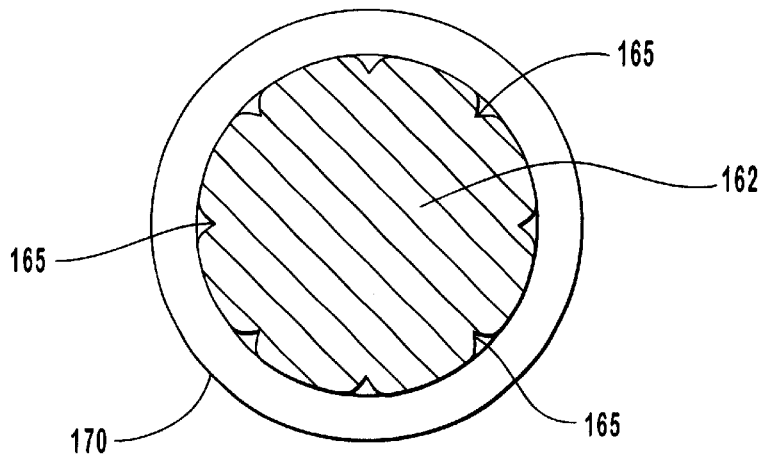
FIG. 4 is a cross sectional view along plane 4 of the anvil shown in FIG. 3B.
Figure 5:
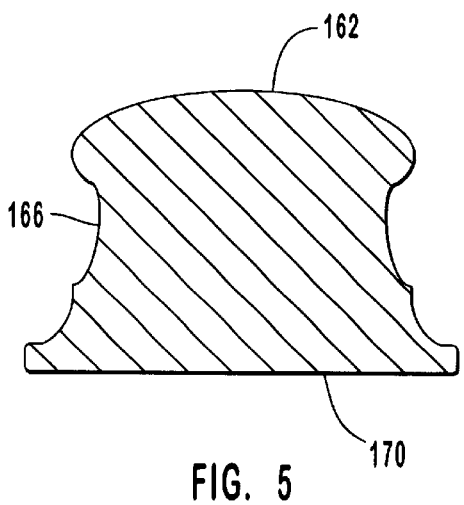
FIG. 5 is a cross sectional view along plane 5 of the anvil shown in FIG. 3C.
Figure 6:
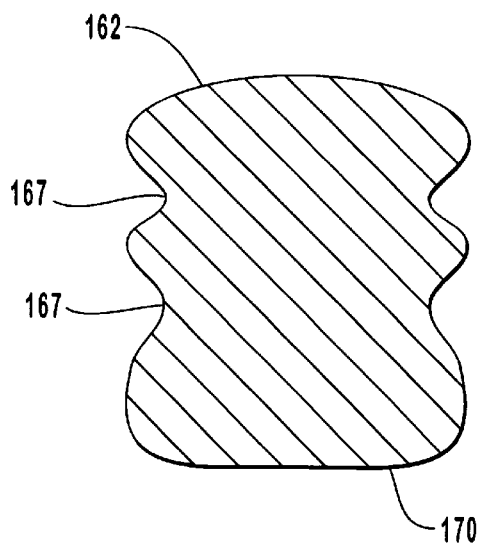
FIG. 6 is a cross sectional view along plane 6 of the anvil shown in FIG. 3D.

As shown in FIG. 3A, deflecting surface 164 of anvil 160 can be smooth, or it can be provided with depressions as shown in FIGS. 3B–3D. These depressions are formed with the appropriate shape for deflecting a pointed end such as the pointed end of a needle or a staple, and they can include a variety of concave shapes such as depressions 165 and 166, or a combination of concave and convex shapes such as in 167. FIGS. 4, 5 and 6 show cross sections along the lines 4–4', 5–5' and 6–6', respectively of the embodiments of the anvil shown in FIGS. 3B–3D.

Although receiving surface 162 is schematically shown in FIGS. 1–6 as a flat surface that is perpendicular to the longitudinal axis of each one of the embodiments of the anvil of this invention, other embodiments may have a slanted receiving surface such as surface 168 when the anvil abutting the wall of the receiving blood vessel has to cooperate in the formation of, for example, a bevelled anastomosis. This shape of an embodiment of an anvil according to this invention is schematically illustrated in FIG. 7. Furthermore, the outer perimeter of a cross section perpendicular to the longitudinal axis of an embodiment of an anvil according to this invention can be shaped in anyone of a plurality of curved figures, such as a circumference, an ellipse, an ovoid, and combinations of arcuate portions.

Receiving surfaces 162 and 168 can additionally, or alternatively, provide an absorbing medium for radiation directed against it. Radiation to which receiving surfaces 162 and 168 might be exposed to is radiation from one of the laser sources typically used in surgical procedures. Materials that absorb this type of radiation have been discussed hereinabove.

As shown in FIGS. 3A, 3D, 6 and 7A, base 170 of the anvil of this invention does not necessarily have to form a flange or ledge at the edge of a broad and generally flat surface, but it can also be shaped with smooth rounded edges, have a shape generally symmetrical to that of receiving surface 162, or be shaped in a combination of curved and/or straight contours. Shapes of base 170 such as those shown in FIGS. 3D, 6 and 7A can be more useful for diminishing the drag while the anvil is moved within and along the receiving blood vessel.

In another embodiment of this invention, the anvil of this invention can be embodied by a puncture resistant balloon. Puncture and scratch resistant balloons have been disclosed in U.S. Pat. Nos. 5,766,158, 5,662,580, 5,620,649, 5,616,114, 5,613,979, 5,478,320, 5,290,306, and 5,779,731, which are hereby incorporated by reference in their entirety. In still another embodiment of this invention, the anvil of this invention can be embodied by the combination of a balloon and a puncture resistant balloon sheath. A balloon plus balloon sheath combination has been disclosed in U.S. Pat. No. 5,843,027 which is hereby incorporated by reference in its entirety.

The dimensions of any of the embodiments of the anvil of this invention are determined by the size of the lumen of the receiving blood vessel and by the dimension of the passage that will ensure the fluid communication between the graft vessel and the receiving vessel after they have been anastomosed. The inclination of receiving surface 168 in an embodiment of the anvil of this invention as schematically shown in FIG. 7 is appropriately chosen depending on the diameter of the graft vessel and on the angle at which the graft vessel is to be anastomosed to the receiving blood vessel. These dimensions are known to anyone with ordinary skill in the art.

For example, when the anvil of this invention is embodied by a device as one shown in any of FIGS. 3A–3D and a graft vessel of about 4 mm in diameter is to be anastomosed to a receiving vessel with an approximate lumen diameter of about 8 mm, the height from base 170 to receiving surface 162 can typically range from about 3 mm to about 4 mm, and the diameter of a cross section parallel to receiving surface 162 can typically range from about 3.5 mm to about 4.5 mm. The methods, systems and apparatuses of this invention are preferably used for anastomosing graft vessels whose diameter ranges between about 2 mm and about 20 mm, but there is no fundamental limitation for using embodiments of this invention with graft vessels whose diameter is less than 2 mm.

In general, the material of which any of the exemplary embodiments of the anvil of this invention is made is appropriately chosen to be abrasion resistant, puncture resistant, distortion resistant and/or an effective absorber of radiation depending on whether it is to be exposed to the abrasive action of a cutting device, to the perforating action of a sharp pointed end, to the twisting or distorting action of a gripping device, or to radiation. A cutting device can be, for example, a cutting blade; a sharp pointed end can be, for example, the penetrating end of a staple or the sharp end of a needle; a gripping device can be, for example, a clip, and radiation can be emitted by, for example, a surgical laser.

It is understood that the shapes, specific geometric features and constitutive materials of the foregoing embodiments of catheter apparatus 100 are given for exemplary purposes and they and/or equivalents thereof can be suitably combined or varied by one of ordinary skill in the art to satisfy the objectives of this invention The proximal end of the intraluminally directed apparatus of this invention, and in particular proximal end 114 of catheter apparatus 100, can comprise one or a plurality of access ports or luer fittings. For the purpose of simplicity, only one access port is shown in the embodiment of catheter apparatus 100 schematically shown in FIG. 1. Also for the purpose of showing a simple sketch, the embodiment of catheter apparatus 100 as schematically shown in FIG. 1 only displays one lumen, but catheter apparatus 100, and more generally the intraluminally directed anvil apparatus, can also have a plurality of lumens. The manufacture and handling of an apparatus with a plurality of lumens and a plurality of access ports are part of the ordinary skill in the art. For example, U.S. Pat. Nos. 5,662,580 and 5,616,114, which have herein been incorporated by reference in their entirety, disclose catheters with a plurality of access ports or luer fittings and a plurality of lumens.

Figure 17A:
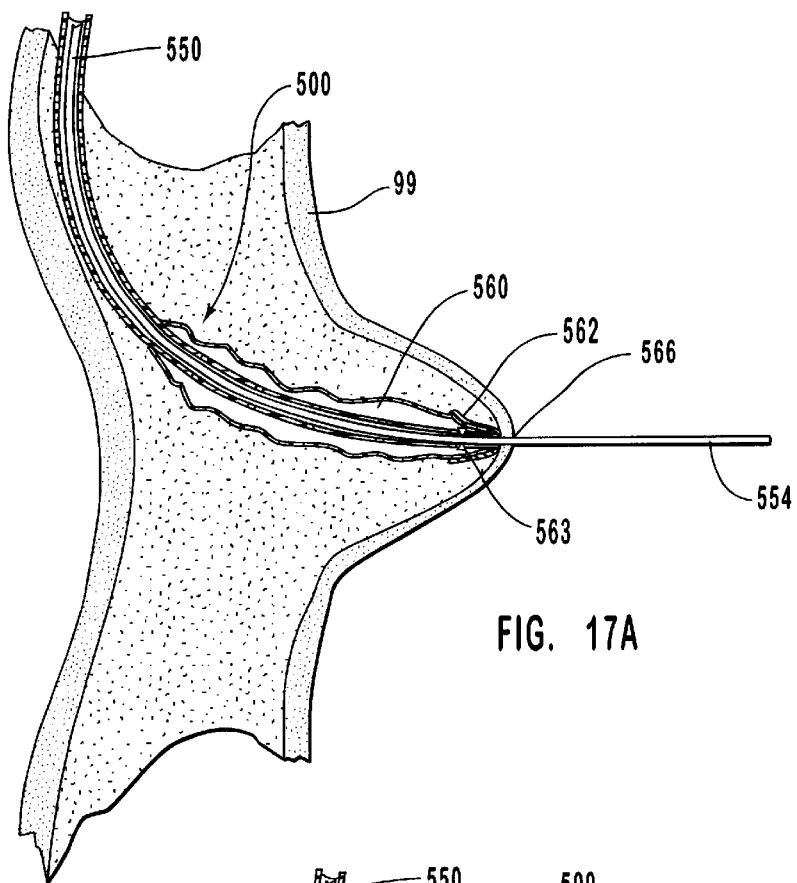
FIG. 17A shows a cross sectional view of another embodiment of the intraluminally directed anvil apparatus with a deflated balloon anvil.
Figure 17B:
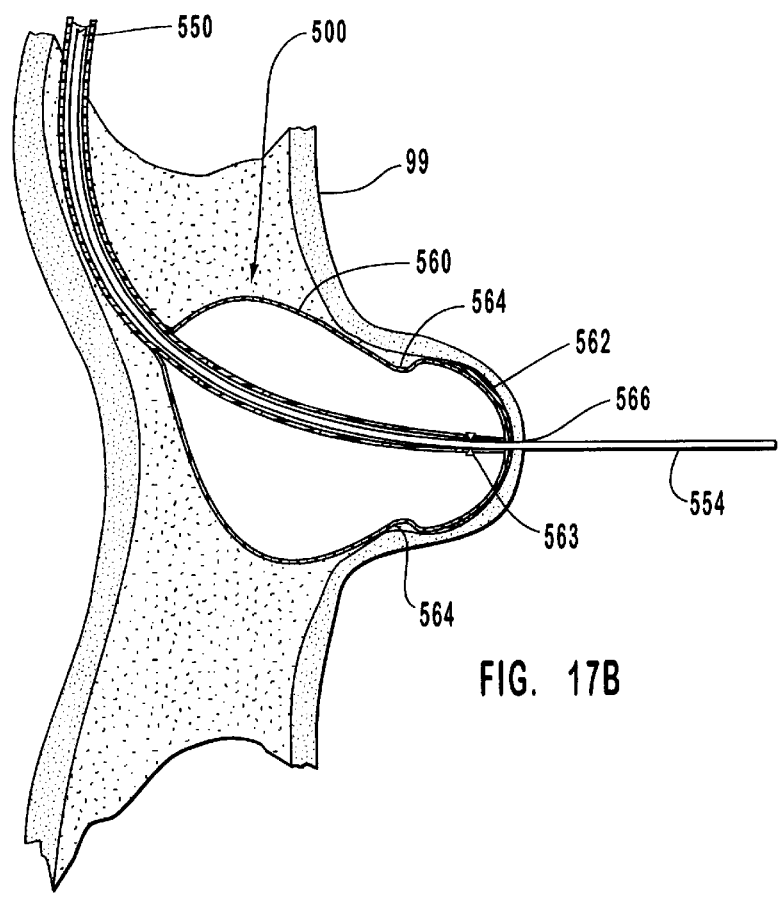
FIG. 17B shows a cross sectional view of the embodiment shown in FIG. 17A where the balloon anvil is inflated and abutting the receiving blood vessel.

Another exemplary embodiment of the intraluminally directed anvil apparatus of this invention is given by catheter apparatus 500 as shown in FIGS. 17A and 17B comprises tubular shaft 505, positioning shaft 550, piercing wire 554, and balloon anvil 560. Dilation of balloon anvil 560 from its collapsed configuration shown in FIG. 17A to its expanded configuration shown in FIG. 17B is accomplished by conventional methods and implements such as inflation with the aid of an additional inflation lumen (not shown in FIGS. 17A and 17B). Although balloon anvil 560 is hereinbelow described as being "inflated" or "deflated", this terminology merely illustrates one possible way of expanding and contracting an embodiment of the balloon anvil of this invention.

Deflated balloon anvil 560 is inserted into the intraluminal space of receiving blood vessel 99 as shown in FIG. 17A and it is inflated at the anastomosis site so that receiving surface 562 of balloon anvil 560 abuts the wall of receiving blood vessel 99 from its intraluminal space. Receiving surface 562 is preferably made of a laser absorbing material when the anastomosis fenestra is to be opened by laser radiation. In addition, the structure of the wall of balloon 560 is such that groove 564 forms when balloon anvil 560 is inflated as shown in FIG. 17B.

Balloon anvil 560, positioning wire 550, and piercing wire 554 are provided with an engagement feature that can be embodied by an attachment 563 as shown in FIGS. 17A and 17B. Attachment 563 can be embodied by any other engagement feature that prevents balloon anvil 560 to slide along positioning wire 550 when extravascular pressure is applied against receiving blood vessel 99 and receiving surface 562.

Another preferred characteristic of balloon anvil 560 is that its dimensions and shape are such that, when inflated, balloon anvil 560 will provide an effective fluid tight seal at the anastomosis site, so that the anastomosis can be performed without interruption of blood flow along the lumen of receiving blood vessel 99. Although not shown in any of FIGS. 17A and 17B, piercing wire 554 has a distal piercing end, like piercing distal end 154 of piercing wire 150, which is sharp enough to pierce the wall of receiving blood vessel 99 at the abutted portion 566.

Figure 7A:
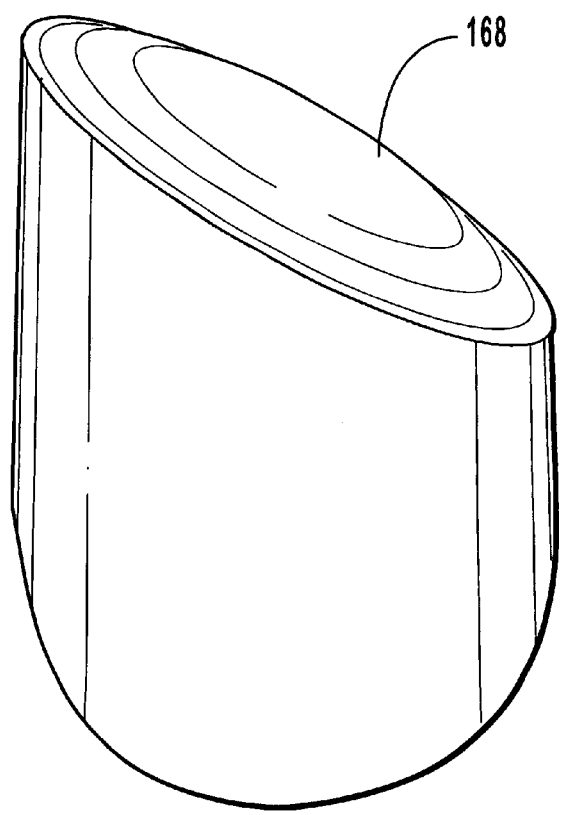
FIG. 7A is a perspective view of an embodiment of the anvil of this invention with a slanted receiving surface.
Figure 7B:
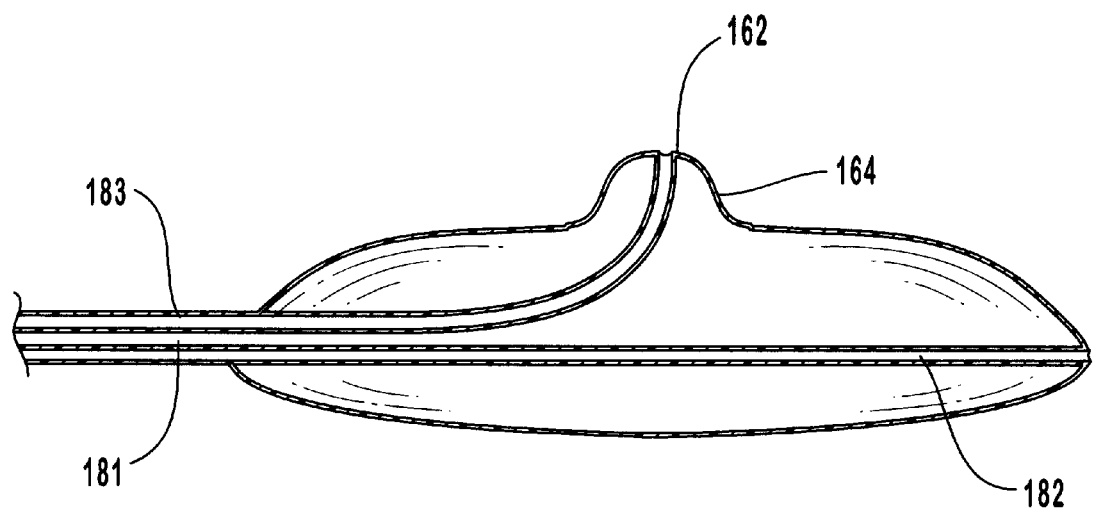
FIG. 7B shows a cross sectional view of an embodiment of a balloon anvil of this invention.

In another embodiment of a balloon anvil of this invention, an inflatable balloon is provided as shown in FIG. 7B with a surface feature that is shaped like the combination of receiving surface 162 and deflecting surface 164. This feature is formed on the surface of the balloon and it is destined to abut the receiving blood vessel wall as any other of the embodiments of the anvil of this invention does. This inflatable balloon is preferably attached to a multilumen catheter with expansion/contraction lumen 181 for inflating and deflating the balloon, positioning shaft 182 for housing the balloon insertion guide wire, and piercing shaft 183 for housing the piercing wire. Piercing shaft 183 is curved within the balloon towards and through the anvil formed on the balloon surface so that it provides a passage that directs the piercing wire towards the intima of the receiving blood vessel.

Like any other embodiment of the anvil of this invention, this balloon anvil can be designed so that the blood flow through the receiving blood vessel will preferably not be interrupted during the anastomosis. However, the design can be such that the blood flow is interrupted when this feature is desired. In a preferred embodiment, the balloon anvil shown in FIG. 7B is designed so that it completely occludes the blood flow within receiving blood vessel 99. With this design, the wall of receiving blood vessel 99 is abutted by the anvil when the balloon anvil is inflated even if the balloon anvil is not attached to the piercing wire.

The term "anvil" in the context of this invention is meant to encompass balloon anvils. The intraluminally directed anvil apparatus of this invention comprises a piercing wire, a conduit for housing this piercing wire, and an anvil. Consequently, a balloon anvil is understood as an anvil whose base is so modified as to be able to be expanded and contracted by, for example, inflation and deflation. The terms "balloon anvil" will still be used when referring to a specific embodiment such as the one shown in FIG. 7B.

The herein disclosed exemplary embodiments of intraluminally directed anvil apparatus of this invention are introduced into the receiving blood vessel and subsequently positioned at the anastomosis site according to different techniques. Typically, a catheter is introduced into the receiving blood vessel with the aid of a guide wire, which is removed once the catheter is properly positioned. It is within and along this catheter that a piercing wire with an anvil attached thereto, as shown in the embodiments depicted in FIGS. 1, 17A, and 17B, is introduced and placed at the anastomosis site. This procedure can also be used to properly place a balloon anvil as shown in FIG. 7B. In this case, positioning lumen 182 can be omitted or it can be used in conjunction with the guide wire. With or without retracting the guide wire, a piercing wire is introduced within and along piercing shaft 183 of the embodiment shown in FIG. 7B to pierce the wall of the receiving blood vessel at the anastomosis site. Alternatively, a deflated balloon anvil such as the embodiment shown in FIG. 7B can optionally be directly introduced into the receiving blood vessel along a guide wire that is housed in positioning lumen 182 without resorting to the passage of the balloon anvil within and along any other additional foreign tubular structure such as tubular shaft 110 of catheter 100. With the balloon anvil so positioned and inflated at the anastomosis site, the receiving blood vessel is then pierced with a piercing wire.

Anastomosis Device

In an embodiment of this invention, the length of wire 150 that extends outside the receiving blood vessel signals the chosen anastomosis site. This wire is used for cooperatively performing the anastomosis of a graft vessel with anastomosis device 200.

Another example of an anastomosis device is shown in FIGS. 8–14 as a peripheral device whose primary components comprise centering core 207, cutter 213, staple pushing device 219, activation sheath 233, staples 308, and two rings: staple guide ring 300 and anastomosis ring 350.

Figure 8:
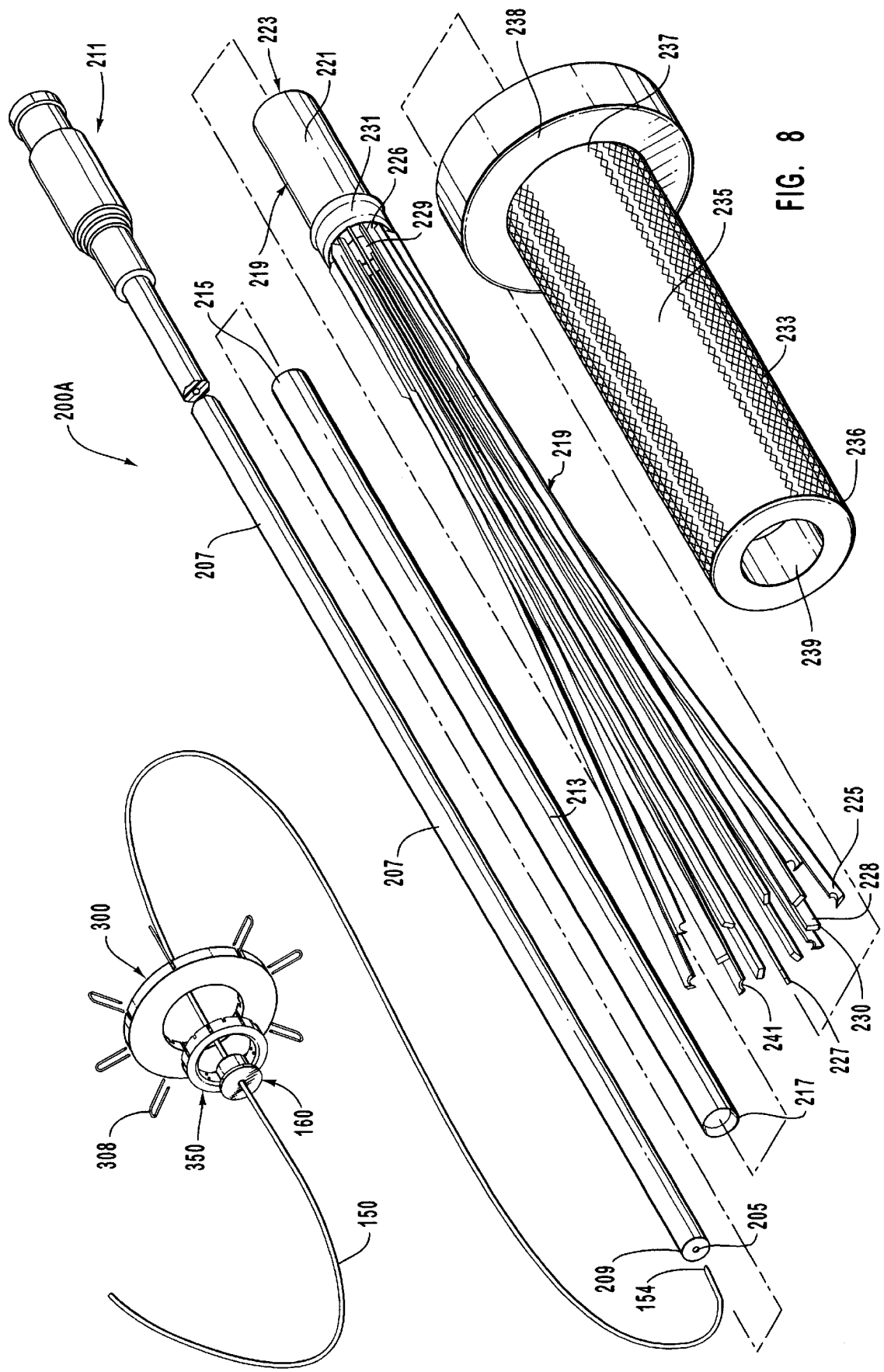
FIG. 8 shows an exploded view of an embodiment of the peripheral device of this invention.

Distal end 154 of wire 150 is introduced in the embodiment shown in FIG. 8 through anastomosis ring 350, staple guide ring 300 and through conduit 205 that extends coaxially within centering core 207 from its distal coupling end 209 to its proximal control end 211. The length of wire 150 that extends outside the receiving blood vessel is sufficient to allow distal end 154 to sufficiently project beyond proximal control end 211 for an operator to be able to hold and pull wire 150 from the region near distal end 154.

In one embodiment of the anastomosis device of this invention, proximal control end 211 comprises a "flow switch" 212 as exemplarily shown in FIGS. 11 and 12. A flow switch is a device that provides a releasable locking mechanism. Flow switches are well known commercially available devices. One example of such device is the flow switch that is marketed under the name FloSwitch by Boston Scientific Corporation. Other devices that provide a locking mechanism can be used instead of flow switch 212.

As shown in FIG. 8, centering core 207 is coaxially aligned within hollow cutter 213, whose length from proximal end 215 to distal cutting end 217 is less than the length of centering core 207 from its proximal control end 211 to its distal coupling end 209. Distal cutting end 217 is provided in this exemplary embodiment of the invention with a sharp cutting edge along the entire perimeter of the generally cylindrical cutter 213 at cutting end 217. Furthermore, distal cutting end 217 is made of metals or alloys that are suitable for providing such sharp cutting edge and/or distal cutting end 217 can be coated with a material or materials that prevent the tissue being cut from adhering onto it. An example of such material is teflon.

Centering core 207 is shown in FIG. 8 as a solid core with conduit 205 extending coaxially therethrough. In other embodiments of this invention, centering core can be embodied by an axially extending tube, guide or any other similar passage that provides a housing for extending the piercing wire therethrough.

In turn, the embodiment of this invention shown in FIG. 8 shows cutter 213 coaxially disposed within the staple engaging device 219. For example, staple engaging device 219 comprises a hollow cylindrical portion 221 at its proximal end 223. This hollow cylindrical portion 221 facilitates the coaxial fitting of staple engaging device 219 and it provides support in this particular embodiment to staple pushing arms 225 and to retention arms 228. Both staple pushing arms 225 and retention arms 228 extend from their respective proximal ends 226 and 229 to their respective distal pushing ends 227 and retention ends 230.

Figure 9A:
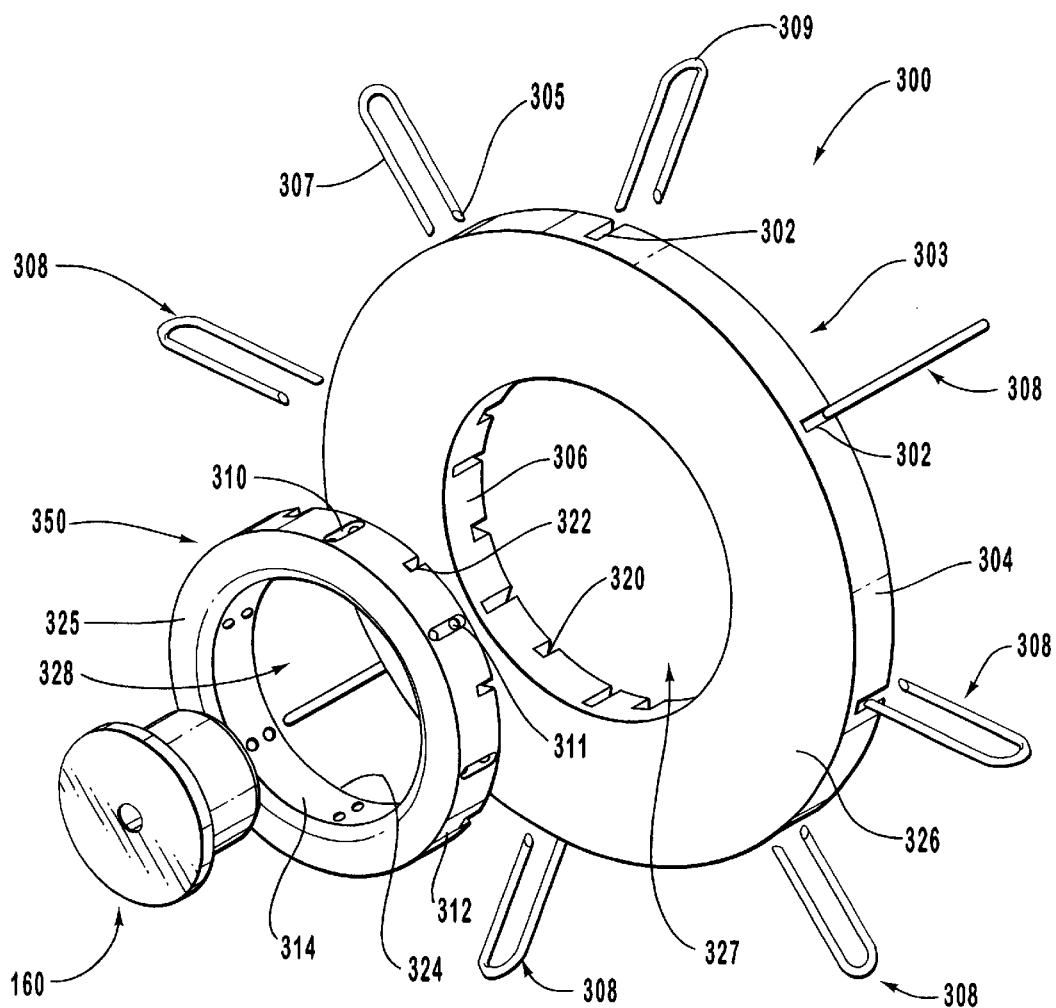
FIG. 9A shows an exploded view of an embodiment of the staples, anvil, anastomosis ring and staple guide ring of the embodiment of the peripheral device shown in FIG. 8.
Figure 9B:
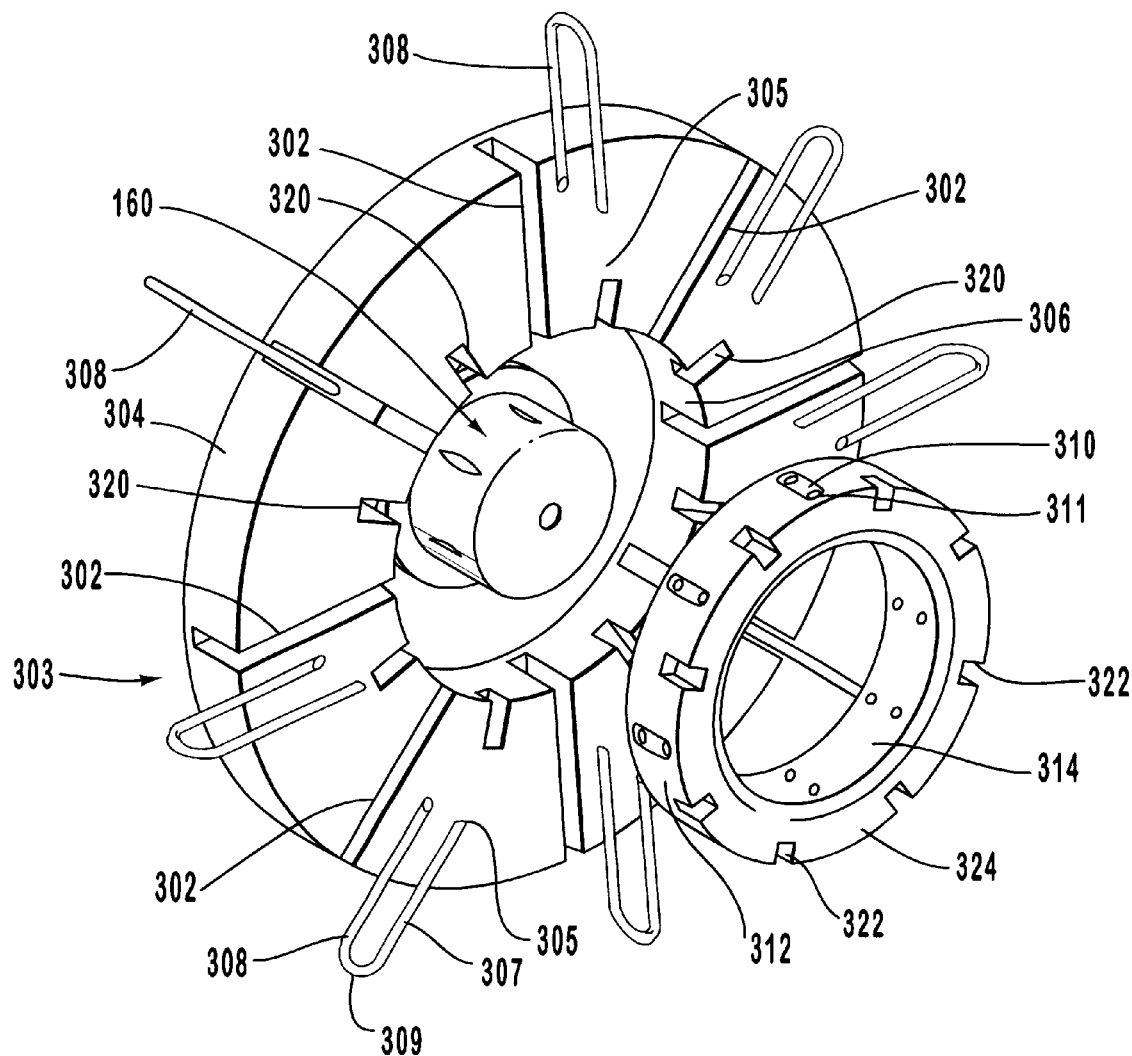
FIG. 9B shows another exploded view of the embodiment shown in FIG. 9A, when the perspective view is offered from the opposite side to that shown in FIG. 9A.
Figure 9C:
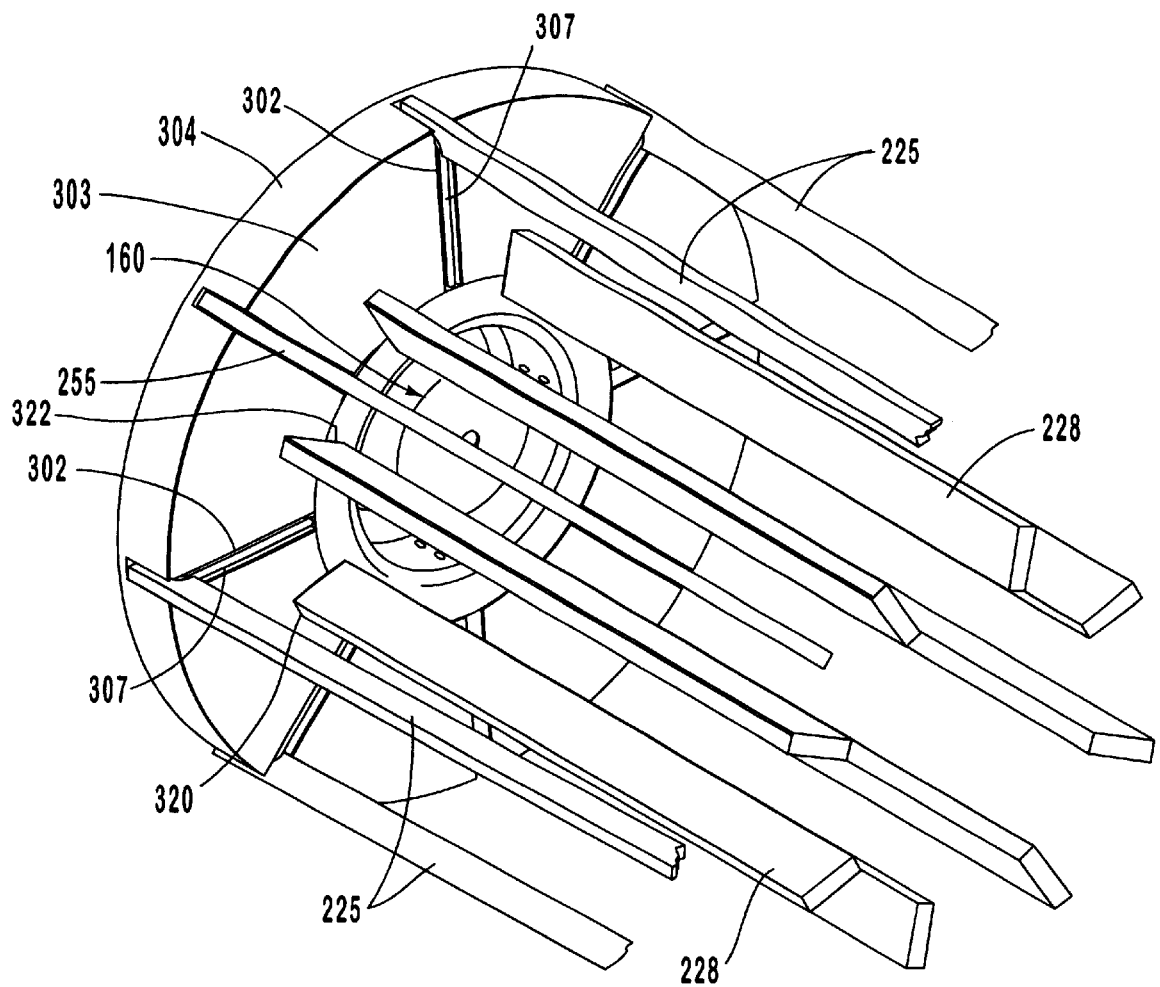

Although eight pushing arms and eight retention arms are shown in the exemplary embodiment depicted in FIGS. 8 and 9C and consequently the numbers of troughs 310 and notches 322 in anastomosis ring 350 and the numbers of staple grooves 302 and notches 320 in staple guide ring 300 are also eight, other embodiments of the anastomosis device of this invention may rely on more or less than eight of any of these corresponding elements. Reliance on less than eight staples with their corresponding troughs 310 and staple grooves 302 may be adequate when the anastomosed structures are joined by the combined effect of a mechanical device such as staples or clips and radiation welding, gluing or soldering. Reliance on more than eight staples with their corresponding troughs 310 and staple grooves 302 may be suitable for the larger anastomosed structures whose joining is performed with staples only.

Each retention arm 228 is generally disposed longitudinally from its proximal end 229 to its retention end 230 approximately parallel to the longitudinal axis of centering core 207 and cutter 213. In contrast, each staple pushing arm 225 is tension loaded so that, absent a constraint, the locus of each distal pushing end 227 will be part of an approximately circular perimeter whose diameter is greater than the diameter of the approximately circular perimeter that is defined by the locus of each retention end 230. Proximal ends 226 and 229 of staple pushing arms 225 and retention arms 228 are respectively attached to affixing end 231 of hollow cylindrical portion 221. Proximal ends 226 and 229 are preferably integrally attached to affixing end 231, but they can also be affixed to affixing end 231 by welding or with the aid of a fastener. Alternatively, proximal ends 226 and 229 can be integrally attached to a mount that threadably engages preferably the inner surface of hollow cylindrical portion 221 at affixing end 231. In a preferred configuration of the embodiment of this invention shown in FIG. 8, the distance from proximal end 223 of the hollow cylindrical portion 221 to any distal pushing end 227 is such that staple engaging device 219 is slightly shorter than cutter 213.

Although in the preferred embodiment shown in FIG. 8 staple pushing arms 225 and retention arms 228 are attached to hollow cylindrical portion 221, retention arms 228 could in other embodiments of this invention be attached by their proximal ends to a hollow cylindrical portion. Similarly, pushing arms 225 could be attached by their proximal ends to another generally co-axial and independent cylindrical portion.

Other exemplary embodiments of the anastomosis device of this invention do not rely on retention arms 228. These embodiments are otherwise similar to those herein described.

Each distal pushing end 227 preferably has a feature that aids in the effective driving by distal pushing end 227 of a staple or similar fastening device. This feature can be an indentation such as indentation 241 shown in FIG. 8, a series of indentations, an arcuate or hooked feature or any other feature that is suitable for this purpose and whose design is part of the ordinary skill in the art.

The embodiment shown in FIG. 8 also comprises activation sheath 233 that is coaxially disposed outside and around staple engaging device 219. Activation sheath 233 is shorter than any staple pushing arm 225 or retention arm 228. In a preferred embodiment of activation sheath 233, sleeve 235 extends from guiding distal end 236 to handling proximal end 237, which in turn extends outwardly as flange 238.

In the embodiment of activation sheath 233 shown in FIG. 8, flange 238 extends along the entire perimeter of handling proximal end 237 that is preferably and generally shaped like a circumference. The purpose of flange 238 is to aid in the handling of activation sheath 233, and in particular to aid in the sliding back and forth of activation sheath 233. Consequently, it is understood that flange 238 can be shaped in any of a plurality of shapes that are not shown in FIG. 8. For example, flange 238 can be embodied by a pair of approximately opposed flat flanges, handles, or by a pair of approximately opposed rings. These features are commonly found in syringes at or near the end through which the syringe piston is inserted and no further discussion of such features or their equivalents is provided because they and their forms of attachment to sleeve 235 are within the ordinary skill in the art. Instead of flange 238, a groove along the perimeter of proximal end 237 can provide in other embodiments of activation sheath 233 the necessary grip for pushing or pulling activation sheath 233. Furthermore, an activation sheath 233 with a smooth outer surface of sleeve 235 or with rugosities in outer surface of sleeve 235 as shown in FIG. 8 can still be part of an embodiment of activation sheath 233 with no flange 238.

The forward motion of activation sheath 233 causes distal pushing end 227 of each staple engaging device 219 to move radially inwards. This is predominantly achieved by the slidable engagement of inner surface 239 of guiding distal end 236 with each staple pushing arm 225. Although not shown in FIG. 8, indentations or grooves in inner surface 239 facilitate the slidable engagement of inner surface 239 with each staple pushing arm 225.

The exemplary embodiment shown in FIGS. 8, 9A–9C also comprises staple guide ring 300 and anastomosis ring 350. A plurality of staple grooves 302 are disposed in retention side 303, preferably equally spaced and radially extending from outer side wall 304 to inner side wall 306 of staple guide ring 300. In a preferred embodiment, a staple 308 slides within each staple groove 302 upon being driven radially inwards from outer side wall 304 to inner side wall 306 by each distal pushing end 227.

A plurality of troughs 310 are preferably disposed in anastomosis ring 350, each corresponding with a staple groove 302. Each trough 310 is perforated by preferably two staple prong passages 311 extending radially from outer side wall 312 to inner side wall 314.

Anastomosis ring 350 is so dimensioned that it concentrically fits within the space limited by inner side wall 306 of staple guide ring 300. When anastomosis ring 350 and staple guide ring 300 are properly held in a concentric configuration, each staple 308 can radially slide upon being driven by distal pushing end 227 acting on driving portion 309. Each staple 308 thereby slides along each staple groove 302 so that each staple prong 307 moves radially inwards along a corresponding staple prong passage 311. When staple 308 is fully driven into anastomosis ring 350, driving portion 309 remains within trough 310 and each puncturing end 305 inwardly protrudes through each corresponding staple prong passage opening 311 into the space defined by inner side wall 314. A deflecting surface such as any of surfaces 164–167 of an anvil such as any of the embodiments of an anvil shown in FIGS. 3–7 will cause each staple prong 307 to bend according to the shape imposed by the deflecting pattern which in turn is determined by the geometric features of the deflecting surface. A few examples of such geometric features are shown in FIGS. 3–7, but no additional embodiments of such features are offered here because the choice of the geometric features of a deflecting surface to achieve a specific staple bending pattern is within the ordinary skill in the art. A plurality of notches 320 are preferably equally spaced along the inner perimeter of staple guide ring 300.

Anastomosis ring 350 can be shaped in any one of a variety of equivalent configurations that can be designed with the aid of ordinary skill in the art consistently with the purposes of the anastomosis ring of this invention. These purposes include providing support to the structures being anastomosed, providing support to the staples being driven through the vessels, causing the anastomosed structures to conform around the anvil of this invention if an anvil is used, and forcing the surfaces of the graft vessel and the receiving blood vessel against each other. Anastomosis ring 350 is preferably made of titanium, but it can also be made of any other biocompatible material that is resilient enough to perform according to the purposes of the anastomosis ring of this invention. In particular, anastomosis ring 350 can be made of the same materials of which coupling anastomosis devices are made. In other embodiments of this invention, the anastomosis ring is a removable ring that can be taken away from the anastomosed structures once they have healed into a leak-proof-joint.

Staple guide ring 300 and anastomosis ring 350 are preferably held with respect to each other in a concentric and fixed position. This is preferably achieved in the embodiment shown in FIGS. 8, 9A–9C with the aid of a plurality of notches 320 and 322 which are best viewed in FIG. 9B. Notches 320 are disposed in inner side wall 306 of staple guide ring 300, preferably equally spaced on retention side 303. Notches 322 are disposed in inner side wall 314 of anastomosis ring 350, preferably equally spaced on retention side 324 and corresponding with respective notches 320 in staple guide ring 300. Each pair of corresponding notches 320 and 322 so disposed defines a retention slot that receives retention end 230 of retention arm 228. When each retention end 230 is so engaged with each corresponding retention slot, staple guide ring 300 and anastomosis ring 350 are concentrically fixed with respect to each other to permit the sliding of staples 308 along staple grooves 302 into troughs 310 and through staple prong passages 311.

Staple guide ring 300 and anastomosis ring 350 as shown in FIGS. 8 and 9A–9C are mating structures with outer side wall 312 of anastomosis ring 350 destined to be in contact engagement with inner side wall 306 of staple guide ring 300. In other embodiments of the staple guide ring and anastomosis ring of this invention, these two rings can be aligned with respect to each other with the aid of mating keys on one of the rings and slots on the other ring. In one configuration, the key or keys in these keyed rings are located on inner side wall 306 of staple guide ring 300 and the mating slots are located on outer side wall 312 of anastomosis ring 350. In another configuration, the key or keys are located on outer side wall 312 and the mating slots are located in inner side wall 306. One or a plurality of keys can be used for aligning anastomosis ring 350 and staple guide ring 300, and these keys can be shaped in the form of protuberances such as lugs, corrugations or other features that can be mated with complementary features such as slots or indentations.

Other embodiments of anastomosis device 200 can operate with no reliance on anastomosis ring 350. Instead, staples 308 are delivered directly from staple guide ring 300 that more tightly fits around graft vessel 98 near its partially everted end 97. With this embodiment, staples 308 are preferably inserted through staple prong passages that allow the driving portion of each staple to reach or almost reach inner sidewall 314 of anastomosis ring 350. Still in other embodiments of this invention, the staples are preloaded in an anastomosis ring that is hereinafter referred to as "preloaded anastomosis ring", in which case the anastomosis can be performed with no reliance on staple guide ring 300.

In other embodiments of anastomosis device 300, one of a variety of biocompatible anastomosis rings that are eventually dissolved is used as the anastomosis ring. For example, one of such dissolvable materials is marketed by Boston Scientific Corporation under the name TempTip. The dissolvable rings manufactured according to the invention preferably comprise a bioabsorbable material, which can be absorbed over time and replaced with living tissue. An example of a preferred bioabsorbable material that could be used to manufacture the bioabsorvable rings of the present invention is a poly-l-lactic acid polymer, also known as "PLLA". Other bioabsorbable materials known in the art are described in detail in U.S. Pat. No. 4,643,734, which is hereby incorporated by reference in its entirety.

Although the general configuration of staple guide ring 300 and that of anastomosis ring 350 shown in FIG. 9 correspond to rings with generally circular features, in which case the rings are referred to as "circumferential rings", these rings and their lumens 327 and 328, respectively, can be shaped in other curved shapes, such as ellipsoidal, ovoidal or with a combination of arcuate features. These rings are hereinbelow referred to as "non-circumferential rings". Furthermore, staple grooves 302, troughs 310, and staple prongs passages 311 as shown in FIG. 9 are arranged so that the stapled sites generally define a plane that is orthogonal to the longitudinal axis of centering core 207, and then rings 300 and 350 are termed "orthogonal rings". However, these elements can be arranged in the embodiments of this Example so that the stapled sites generally define a plane that is not orthogonal to the longitudinal axis of centering core 207. These configurations (not shown in FIG. 9) may be particularly useful in the practice of bevelled anastomoses. Rings with these configurations are hereinbelow referred to as "non-orthogonal rings".

A function performed by the embodiments of the staple guide ring or the anastomosis ring of this invention is to properly orient the staples according to a predetermined configuration.

Figure 13:
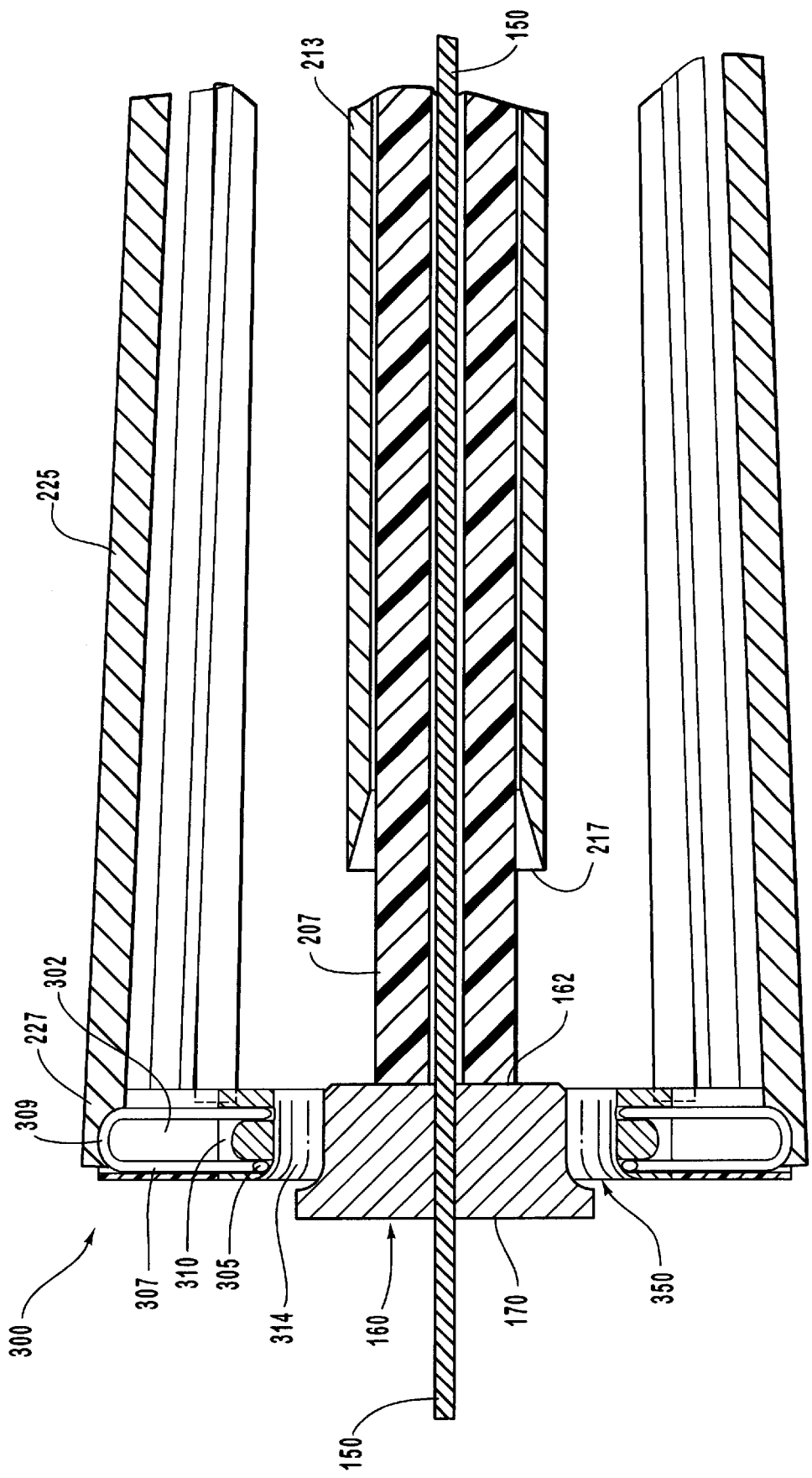
FIG. 13 is a magnified view of the region indicated by arrow 13 in FIG. 12.
Figure 14:
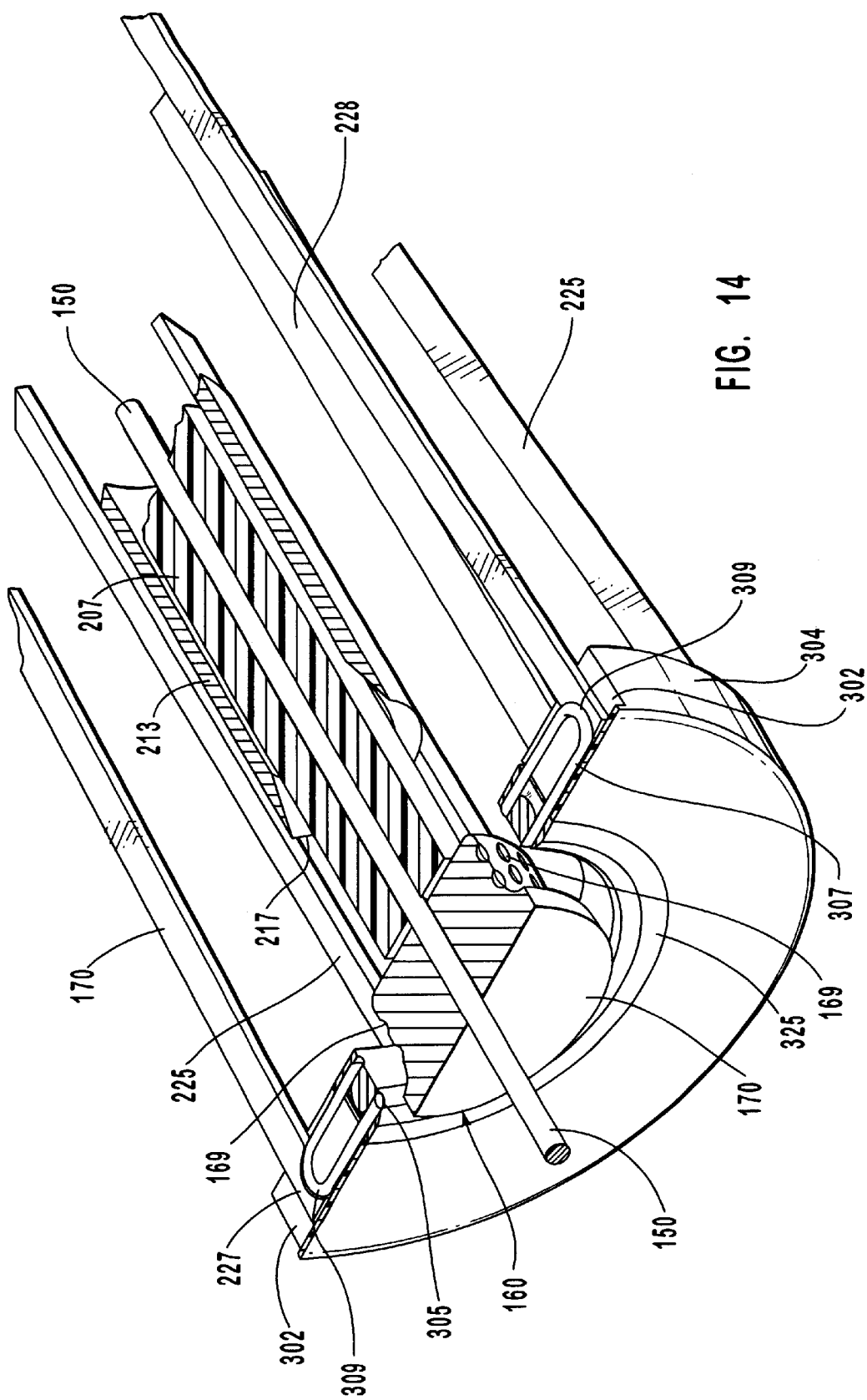
FIG. 14 is a cut away perspective view of the region shown in FIG. 13.

FIG. 10 shows a perspective view of the assembled embodiment whose components are shown in FIGS. 8 and 9. A side view of the same embodiment is shown in FIG. 11, where wire 150 is inserted through the full length of centering core 207 and anvil 160 is inserted into anastomosis ring 350 which in turn is concentrically placed within staple guide ring 300. FIG. 12 shows a cross section along plane 12–12' as indicated in FIG. 10 of the embodiment whose side view is shown in FIG. 11. FIG. 13 shows an enlarged view of region 13–13' as indicated in FIG. 12 and FIG. 14 shows a perspective view of the area whose cross section is shown in FIG. 13. In addition, anvil 160 in FIG. 14 shows a series of depressions 169 for deflecting a pointed end.

Figure 15A:
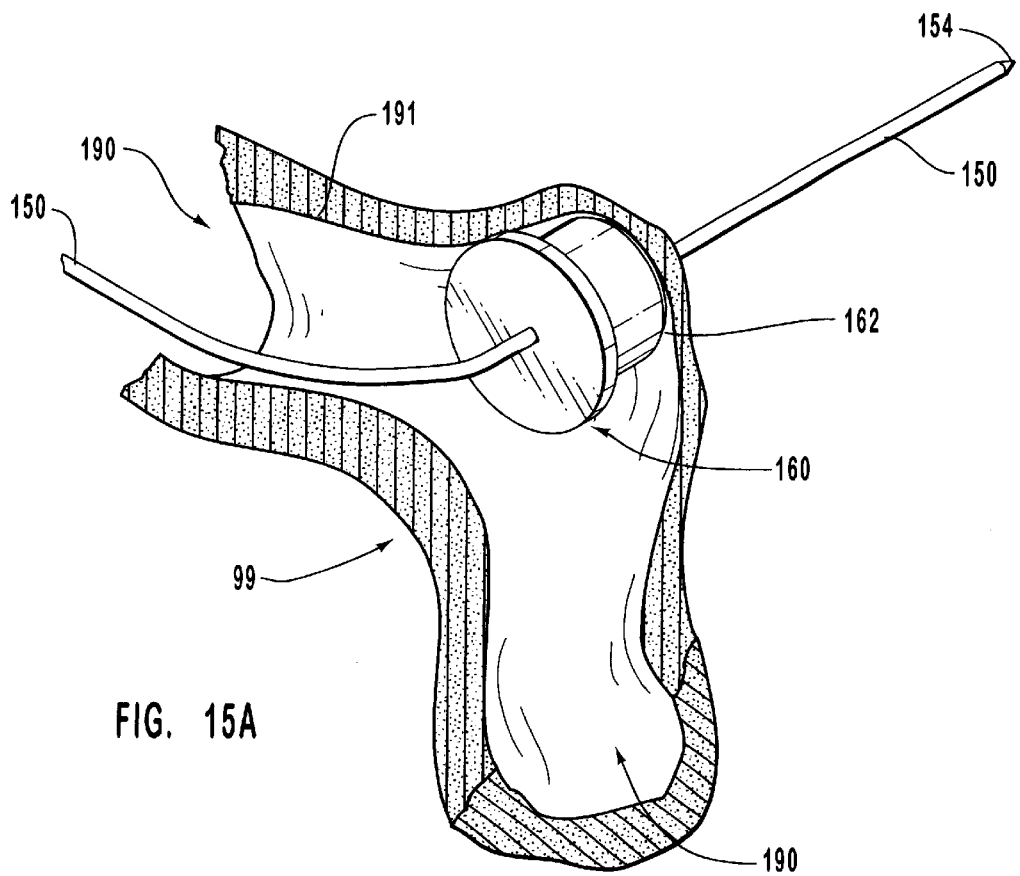
FIG. 15A shows an embodiment of the anvil of this invention abutting the receiving blood vessel from the receiving blood vessel's intraluminal space.
Figure 15B:
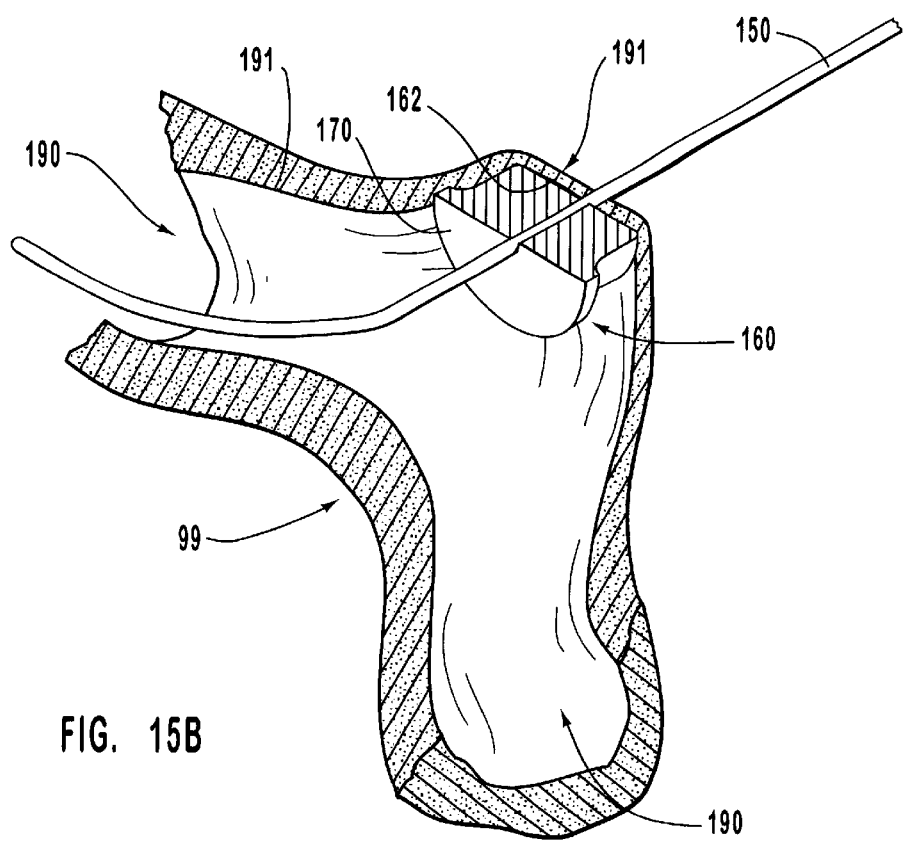
FIG. 15B shows a cross sectional view of an embodiment of the anvil of this invention abutting the receiving blood vessel at the contact region of the receiving surface of the anvil with the intima of the receiving blood vessel.

FIGS. 15A and 15B show an embodiment of the anvil of this invention abutting the wall of receiving blood vessel 99 from intraluminal space 190. FIG. 15A shows distal end 154 of wire 150 having perforated the wall of receiving blood vessel 99 while surface 162 of anvil 160 contacts intima 191 of receiving blood vessel 99. FIG. 15B shows a cross section of anvil 160 effectively abutting the wall of receiving blood vessel 99.

Figure 15C:
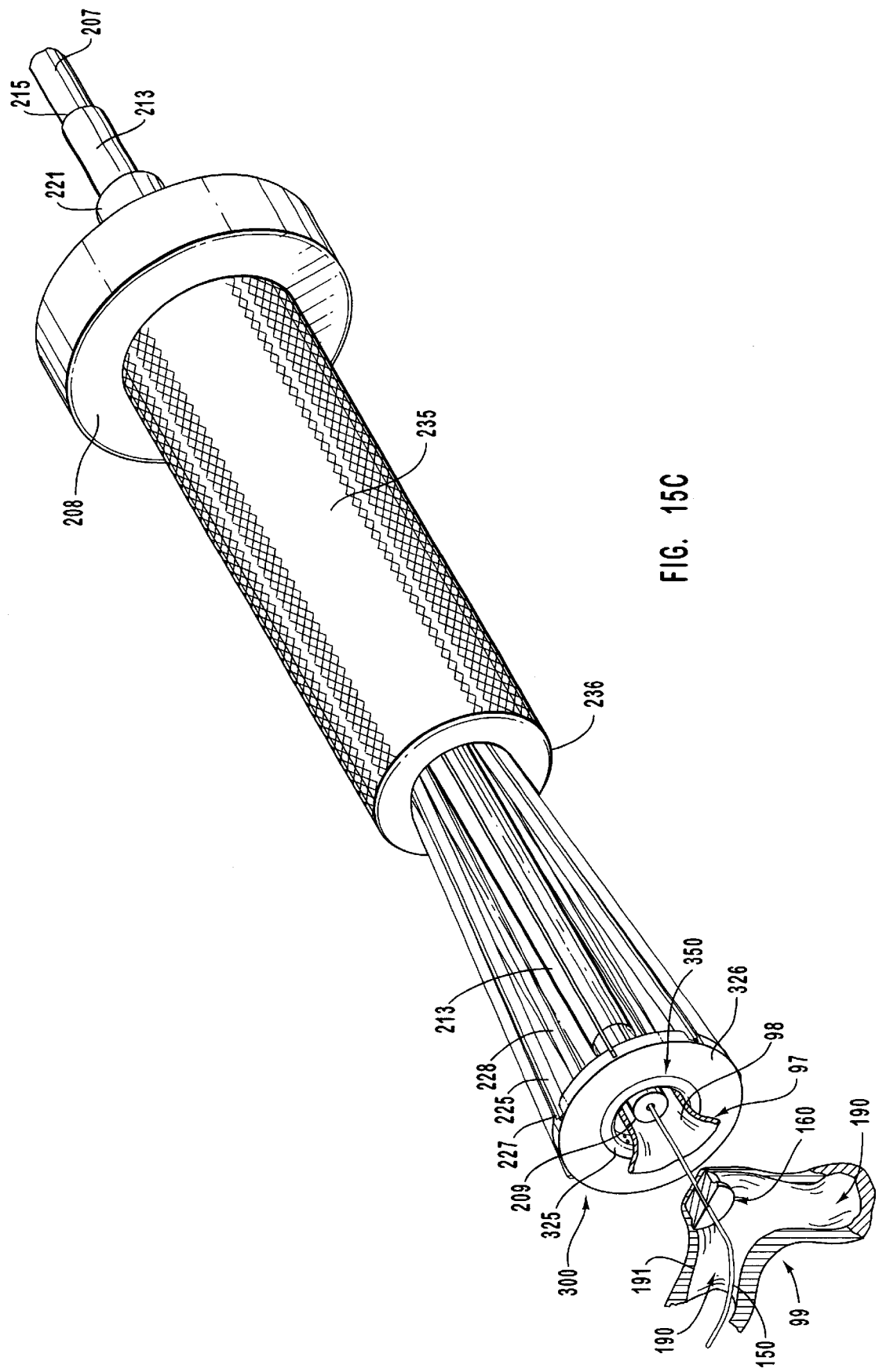
FIG. 15C is a partial perspective view of the embodiment of the peripheral device shown in FIG. 7 showing part of the graft vessel in the peripheral device, the receiving blood vessel abutted by the anvil, and the wire piercing the receiving blood vessel and extending longitudinally within and along the peripheral device.

FIG. 15C shows a perspective view of the embodiment whose components are shown in FIGS. 8 and 9 with a perspective and cut-away view of receiving vessel 99 and graft vessel 98 with its partially everted end 97 over bottom side 325 of anastomosis ring 350 and bottom side 326 of staple guide ring 300.

In the context of this invention, graft vessel 98 can be an autologous blood vessel or a synthetic graft made of biomaterials that have been named in the foregoing discussion of devices and techniques under the general heading Relevant Technology in the Background section of this Specification.

An anastomosis with embodiment 200A shown in FIGS. 8, 10–12 with graft vessel 98 disposed as indicated in FIG. 15C is preferably performed as follows. Embodiment 200A is approached to the abutted side wall of receiving blood vessel 99 by holding the portion of wire 150 that extends beyond proximal control end 211. The embodiment shown in FIGS. 11–12 is slid along wire 150 until the abutted portion of receiving blood vessel 99 is within graft vessel 98 as indicated in the perspective cut-away view shown in FIG. 15D.

During the practice of an end-to-side anastomosis according to this invention with anastomosis device 200A, graft vessel 98 is generally coaxially disposed outside and around cutter 217 so that it is generally coaxially located between cutter 213 and the set of longitudinally extending retention arms 228. In addition, graft vessel 98 is partially disposed through anastomosis ring 350 so that the graft vessel's anastomosis end 97 is partially everted on bottom side 325 of anastomosis ring 350 and on bottom side 326 of staple guide ring 300. Accordingly, the anastomosis ring 350 maintains an end of graft vessel 98 in a desired position for anastomosis. With graft vessel 98 so configured, FIG. 15D shows the anvil of this invention abutting the wall of receiving vessel 99 into intraluminal space 96 of graft vessel 98, near its partially everted end 97 which in turn is surrounded by inner side wall 314 of anastomosis ring 350. Consequently, the outer wall of receiving blood vessel 99 and the inner wall of graft vessel 98 are in contact with each other while they are held between inner side wall 314 of anastomosis ring 350 and an embodiment of the anvil's surface such as any of surfaces 164–167.

Figure 15E:
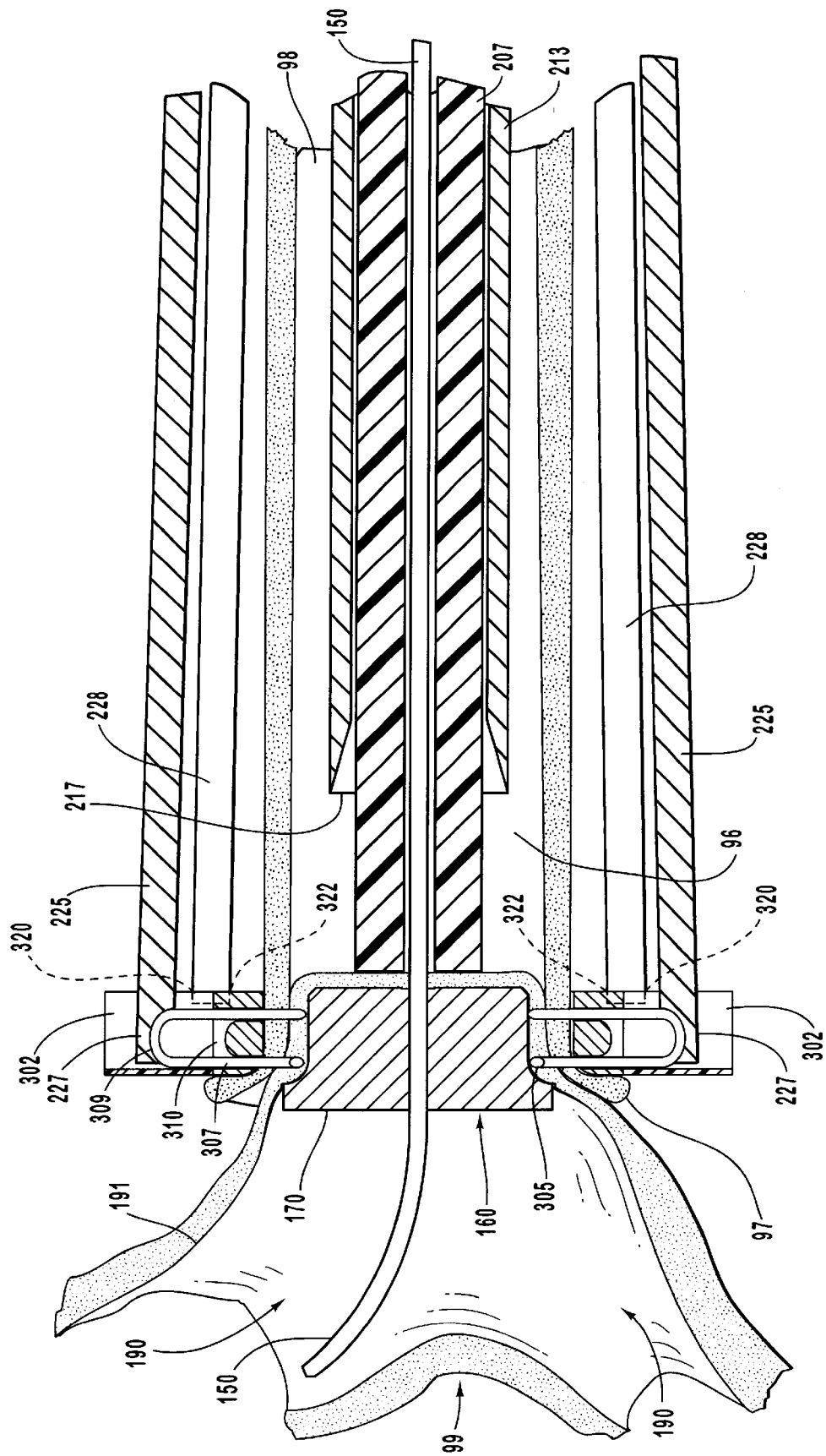
FIG. 15E is a longitudinal cross sectional view of the embodiment shown in FIG. 15D at a stage when the graft vessel is being attached to the receiving blood vessel.
Figure 15G:
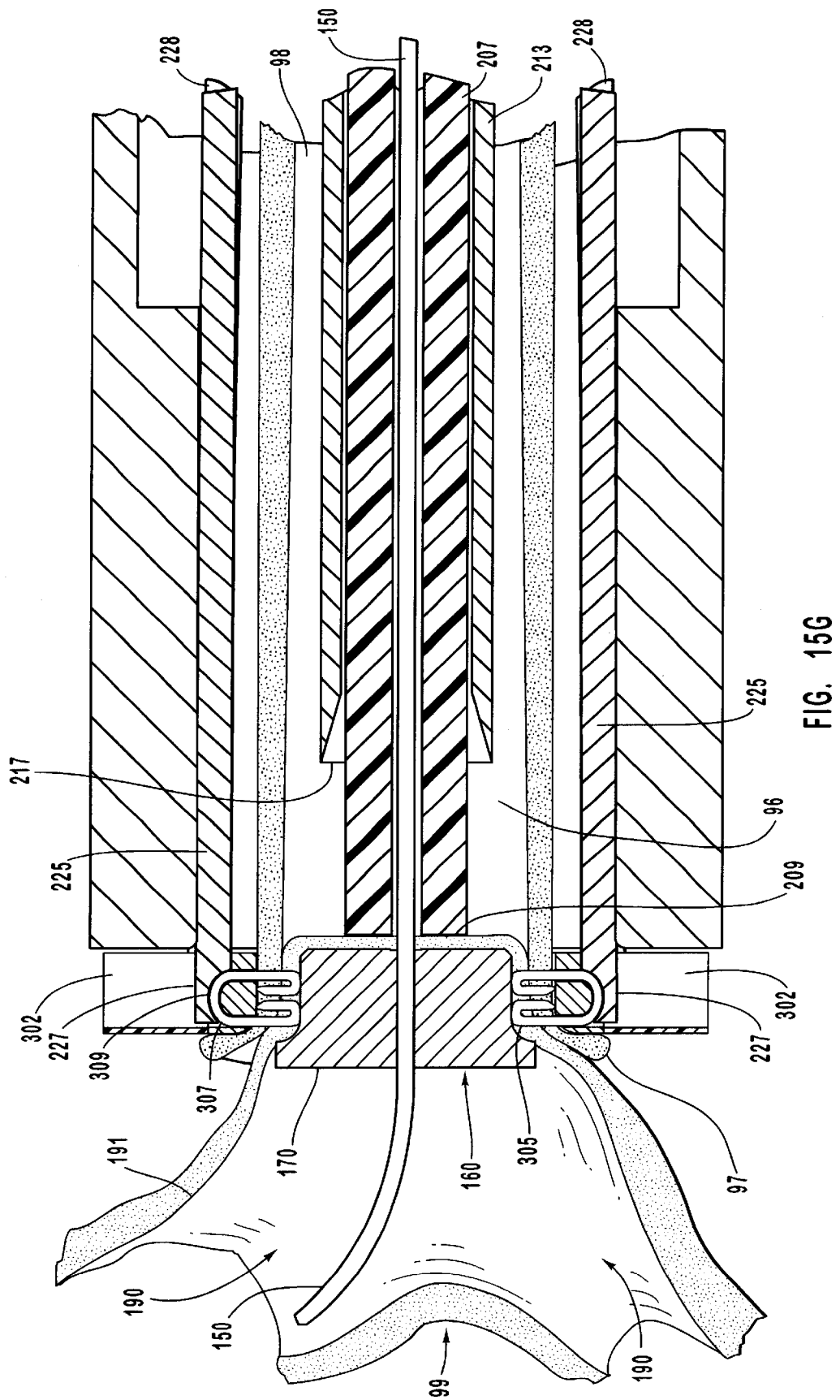
FIG. 15G is a longitudinal cross sectional view of the embodiment shown in FIG. 15F with the graft vessel attached to the receiving blood vessel.

The stapling action with the exemplary embodiment 200A is achieved by sliding activation sheath 233 forward from proximal end 233 of staple engaging device 219 towards distal pushing ends 227 of staple pushing arms 225. This motion causes distal pushing ends 227 that are engaged with corresponding staple grooves 302 to move radially inwards from outer side wall 304 towards inner side wall 306, thus forcing staples 308 to slide within anastomosis ring 350 as described in the foregoing discussion, pierce through graft vessel 98 and receiving blood vessel 99, and staple together anastomosis ring 350, receiving blood vessel 99 and graft vessel 98 at the anastomosis site. This action is illustrated in FIG. 15E by showing, within staple grooves 302, distal pushing ends 227 in contact with driving portions 309 of corresponding staples 308 that are inserted into corresponding troughs 310 and staple prong passages 311 of anastomosis ring 350. As shown in FIGS. 15E, 15F, and 15G, puncturing ends 305 pierce graft vessel 98 and receiving blood vessel 99 to be subsequently bent upon deflection against anvil 160.

Figure 15H:
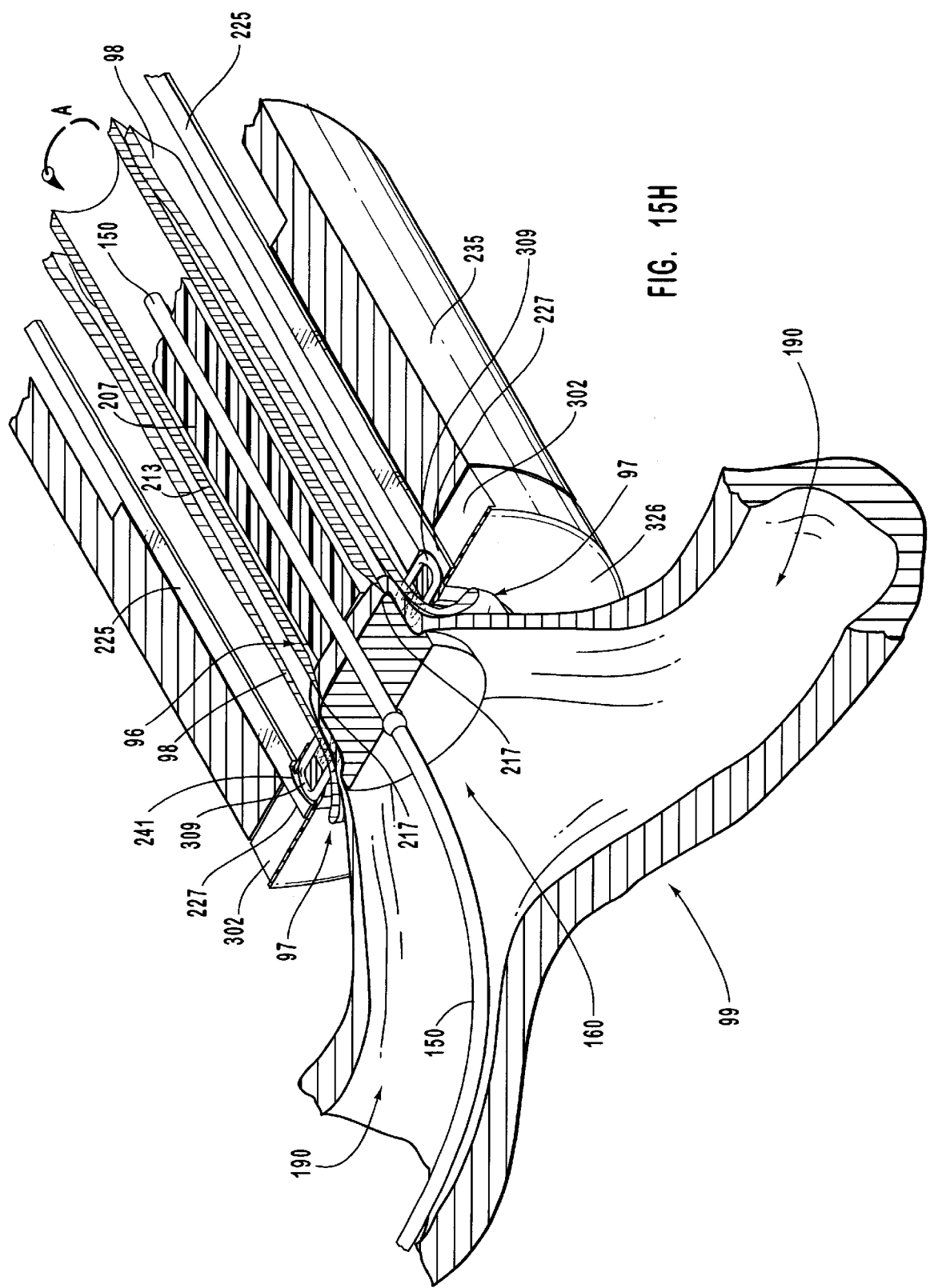
FIG. 15H is a perspective view like the view shown in FIG. 15F showing the opening of the anastomosis fenestra according to one embodiment of this invention.

The operation of cutting an opening into the abutted portion of receiving blood vessel 99 can be performed according to the methods of this invention prior to or after the attachment of graft vessel 98 to receiving blood vessel 99. FIG. 15H illustrates the operation of cutting this opening after anastomosis ring 350, receiving blood vessel 99 and graft vessel 98 have been stapled as shown in FIGS. 15E–15G. In this particular embodiment, cutting is achieved by coaxially inserting cutter 213 until distal cutting end 217 is in contact with receiving blood vessel 99. As indicated by arrow A in FIG. 15H, cutter 213 is then preferably turned about its longitudinal axis or pushed with sufficient force from its proximal end 215 so that distal cutting end 217 cuts through the wall of receiving blood vessel 99 until it is stopped by receiving surface 162 of anvil 160. During this operation, anvil 160 is not significantly displaced backwards into the intraluminal space of receiving blood vessel 99 because a portion of wire 150 extending beyond proximal control end 211 is held so as to effectively counteract any pushing caused by cutter 213.

Figure 15I:
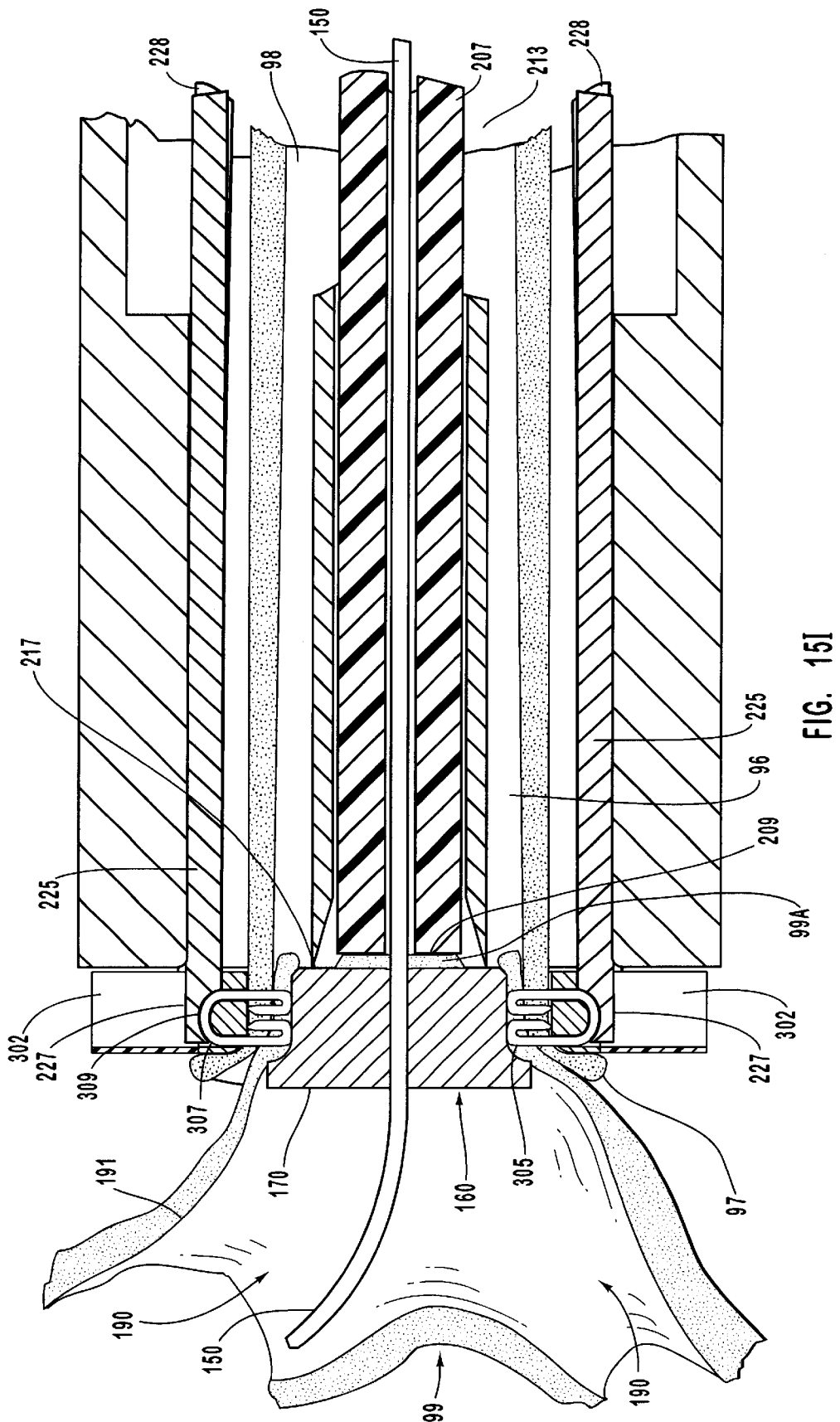
FIG. 15I is a longitudinal cross sectional view of the embodiment shown in FIG. 15H showing the anastomosis fenestra open in the receiving blood vessel.
Figure 15J:
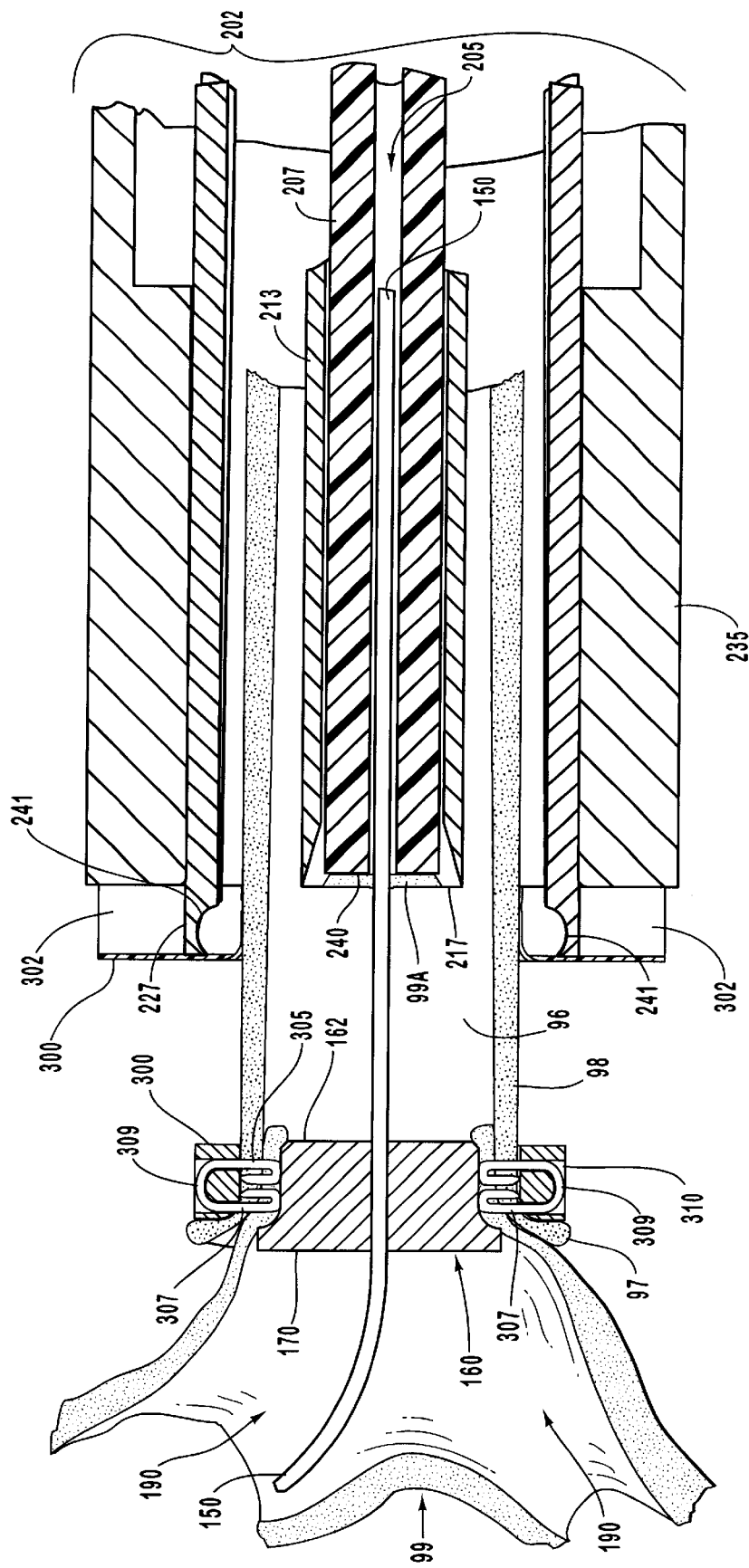
FIG. 15J is a longitudinal cross sectional view like the one shown in FIG. 15I showing the anastomosed structures and an embodiment of the peripheral device of this invention being pulled away from the anastomosis site.

After anastomosis ring 350 is stapled at the anastomosis site as shown in FIGS. 15H and 15I, centering core 207, cutter 213, and staple device 202 with staple engaging device 219 and activation sheath 233 are pulled backwards slidably along wire 150 and away from the anastomosis site as shown in FIG. 15J. This operation also leads to the extraction of staple guide ring 300 that is engaged at notches 320 with corresponding retention ends 230 of retention arms 228. The portion 99A of the abutted wall of receiving blood vessel 99 that is cut upon opening of the anastomosis fenestra is preferably extracted when centering core 207, cutter 213, staple engaging device 219 and activation sheath 233 are pulled backwards. This can be achieved by applying suction at proximal control end 211 to induce in conduit 205 the necessary rarefaction to cause cut out fragment 99A of the wall of receiving blood vessel 99 to attach itself to distal coupling end 209 and thus be extracted upon extraction of centering core 207. In addition, or alternatively, surface 240 of distal coupling end 209 can be provided with a series of axially extending hooked sharp features (not shown in FIG. 15J) that can attach to and facilitate the extraction of fragment 99A upon removal of centering core 207.

Although not shown in FIGS. 15D–15I, distal coupling end 209 of centering core 207 is preferably kept in contact engagement with receiving blood vessel 99 and in a fixed position with respect to wire 150 with the aid of a locking mechanism such as a flow switch that is preferably located at proximal control end 211. Accordingly, centering core 207 is preferably fixed prior to the joining of the structures to be anastomosed and prior to the opening of the anastomosis fenestra. Because the locking mechanism that fixes centering core 207 can be released and re-locked at will several times, one or a plurality of devices with a conduit that can house wire 150 can be approached to the anastomosis site.

The joining of the structures to be anastomosed is exemplarily shown in FIGS. 15D–15J as an operation that precedes the opening of the anastomosis fenestra. However, the structures to be anastomosed can be joined after the anastomosis fenestra is opened in the receiving blood vessel. In addition, FIGS. 15D–15J exemplarily show that the structures to be anastomosed are joined by stapling and that the anastomosis fenestra is opened with a mechanical device such as a cutter. As it will be further disclosed hereinbelow, other procedures can be used in the context of this invention for joining the structures to be anastomosed and for opening the anastomosis fenestra.

Figure 15K:
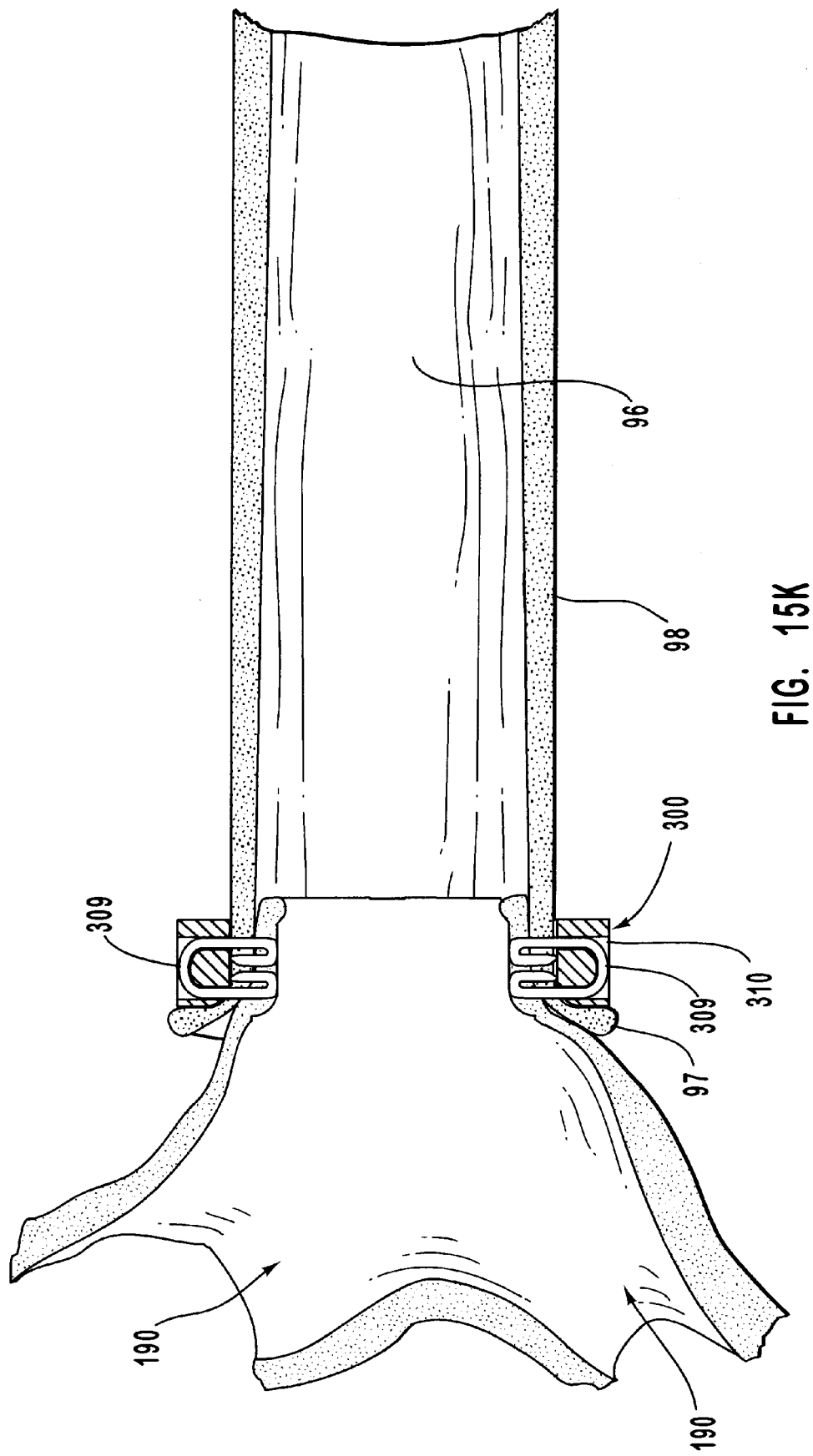
FIG. 15K is a longitudinal cross sectional view like the one shown in FIG. 15J showing the anastomosed structures according to one of the embodiments of this invention.
Figure 15L:
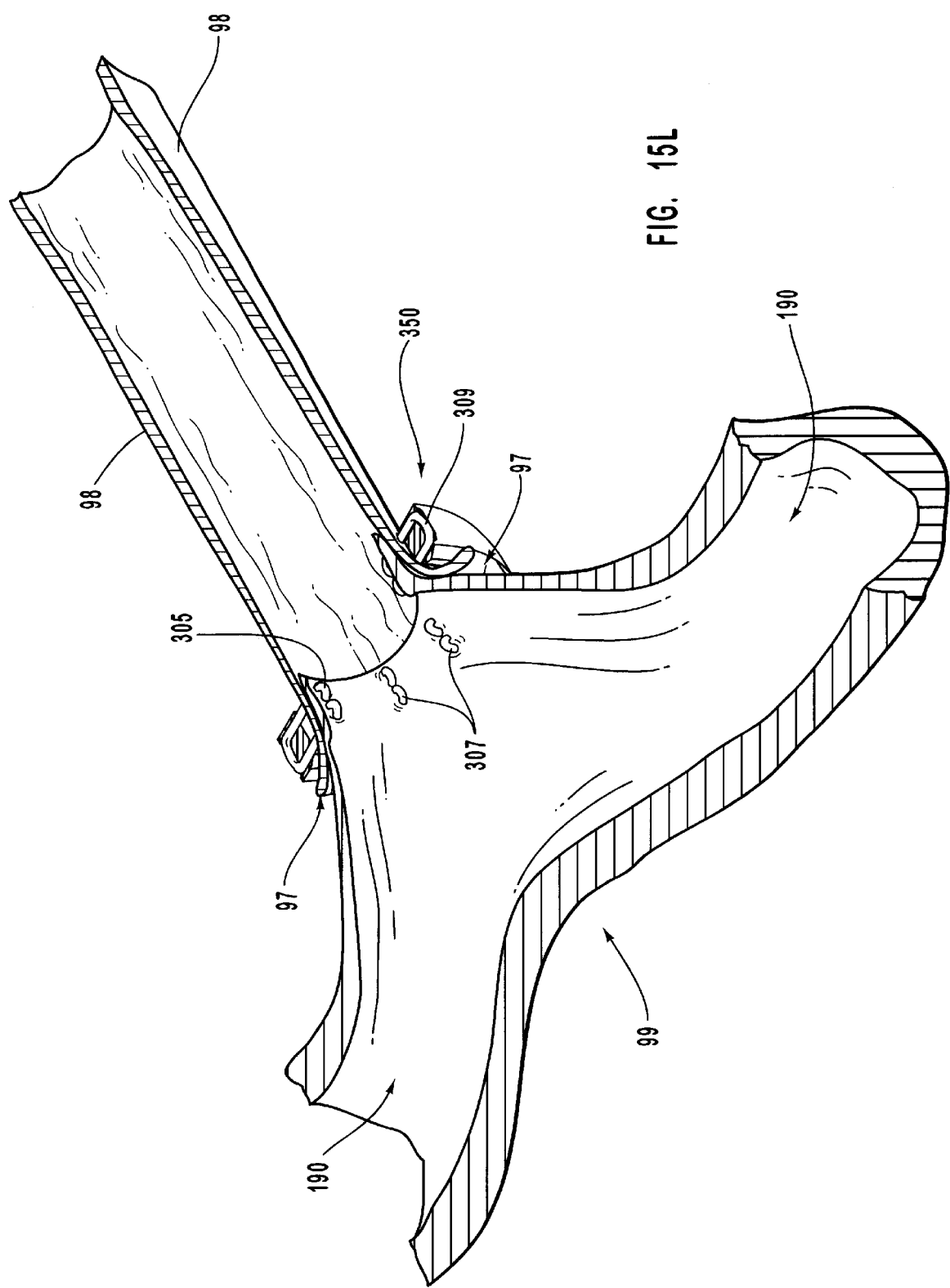
FIG. 15L shows a perspective cut away view of the anastomosed structures shown in FIG. 15K.

FIGS. 15K and 15L show graft vessel 98 anastomosed to receiving blood vessel 99 according to the procedure disclosed in the foregoing discussion of FIGS. 15A–15J. As shown in FIGS. 15K and 15L, anastomosis ring 350 is stapled outside and around the anastomosis site and provides support to the anastomosed structures and to staples 308 used in this particular anastomosis procedure.

Hooked or prebent staples used in these embodiments have features such as those illustrated in FIGS. 16A–16E and combinations of these or similar features that are not explicitly shown in FIGS. 16A–16E but that are within the ordinary skill in the art may be particularly useful with embodiments of anastomosis device 200 that do not rely on anastomosis ring 350. These types of staples generally have prongs 330 that are shorter than prongs 307 of the corresponding staples 308. Hooked staples also have at least one hooked puncturing end 331 instead of merely penetrating puncturing ends 305. Some embodiments of this type of staples have a pre-bent prong such as prong 332. Hooked puncturing ends and/or pre-bent prongs fasten and hold instead of merely penetrating the structures through which they are inserted. Accordingly, the hooked or pre-bent staples require upon insertion no bending of their prongs for holding the vessels being anastomosed together.

Hooked or prebent staples such as those exemplarily depicted in FIGS. 16A–16E may be particularly useful when the presence in the intraluminal space of the anastomosed structures of the terminal portions of prongs 307 and the sharp puncturing ends 305 is not acceptable. In addition, these embodiments would also be preferred when it is desirable to minimize or avoid damage to the intima of the receiving blood vessel, which may result through the use of staples with puncturing ends 305. The practice of this invention with these described embodiments requires the careful determination of the thickness of the graft vessel wall and of the receiving blood vessel wall combined and the subsequent use of hooked staples with the appropriate prong length, so that the intima of the receiving blood vessel is not pierced by the hooked staples.

Other exemplary embodiments of anastomosis device 200 of this invention employ hooked staples that do not pierce the intima of the receiving blood vessel. In addition, these embodiments use anastomosis ring 350 to provide additional support to the anastomosed vessels at the anastomosis site.

These embodiments would be preferred when the anastomosis requires the support of a structure such as anastomosis ring 350. To avoid the piercing of the intima of the receiving blood vessel, the practice of this invention with these embodiments involves the careful determination or estimation of the combined thickness of three structures: that of the graft vessel wall, that of the receiving blood vessel wall, and that of the support structure, such as the distance between outer side wall 312 and inner side wall 314 of anastomosis ring 350.

Other exemplary embodiments of anastomosis device 200 of this invention employ staples or clips that hold and support without the need of being bent upon insertion. Whether the staples are hooked or not, these embodiments of staples predominantly rely on the clipping effect of prongs that spontaneously tend to restore an equilibrium position from which they have previously been distorted, and they are referred to as "memory staples" and "memory clips", respectively.

Figure 16A:
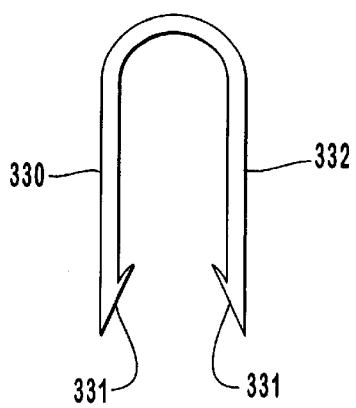
FIGS. 16A–16H show a variety of embodiments of the staples and clips of this invention.
Figure 16D:
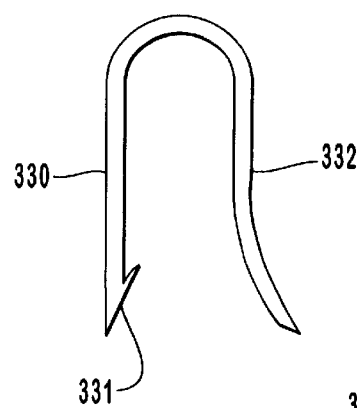
Figure 16G:
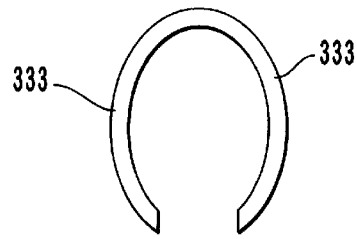
Figure 16B:
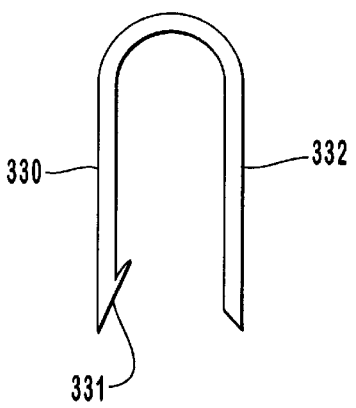
Figure 16E:
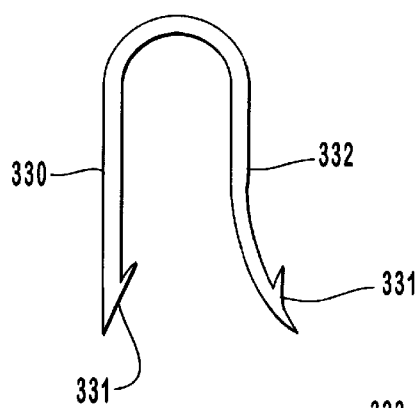
Figure 16H:
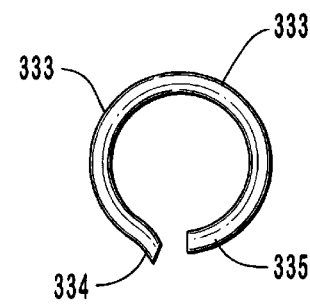
Figure 16C:
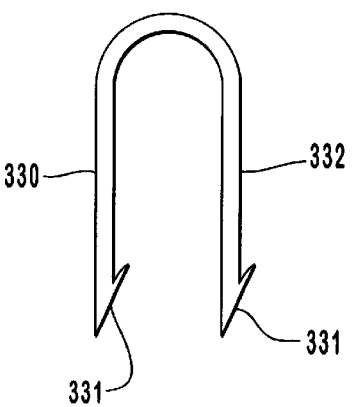
Figure 16F:
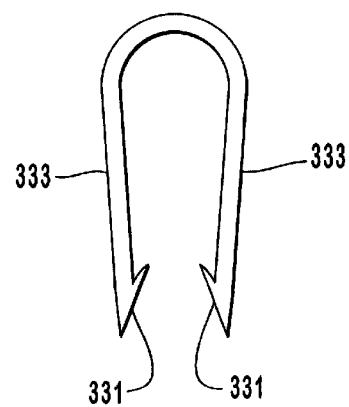

Operationally, these embodiments of staples and clips use a device like that illustrated in FIGS. 8–14, but staples 308 are replaced by staples with prongs that are curved inwards, such as the staples that are shown for example in FIGS. 16F and 16G. These staples are representative of a class of staples whose prongs 333 have been pre-bent towards each other. In addition to the shapes shown in FIGS. 16F and 16G, staples in this class can have one hooked end or two hooked ends, and prongs 333 can be mostly rectilinear such as those of the staple shown in FIG. 16F or mostly curved such as those of the staple or clip shown in FIG. 16G. It is understood that curved portions can have different curvature degrees in addition to those shown in FIGS. 16F and 16G.

When pre-bent staples slide down staple grooves 302 and their prongs slide down staple prong passages in the anastomosis ring, the pre-bent prongs are slightly distorted so that the space between their ends is widened with respect to the equilibrium separation. To avoid irreversible distortion of the staple's shape, this widening is within the elastic compliance of the material used to manufacture the staples of this embodiment. Staple prong passages in the anastomosis ring of this embodiment are so disposed that the prongs of the staples penetrate the graft blood vessel and part of the receiving blood vessel while the space between the ends of the prongs is widened, but the staples are eventually left essentially free to restore or revert to their undistorted shape. This restoration leads effectively to the clipping of the anastomosed vessels without damaging the intima of the receiving blood vessel. Anastomosis ring 350 and in particular staple prong passages 311 are, in these embodiments, appropriately modified for elastically distorting the width of the staples and for allowing them to essentially restore to their initial shape.

Staples and clips used in the context of this invention are preferably made of titanium, titanium alloys or other biocompatible material. In one embodiment of this invention, the anvil is made of tempered stainless steel, although it can be made of other materials that are appropriately selected for resisting the abrasive action of staples. Selection of the appropriate materials can be made by considering the relative hardness of the material that is to be used for the staples or clips and that of the material to be used for the anvil. For example, known scales of relative hardness, such as the Rockwell B scale, provide useful information for this purpose.

Figure 17C:
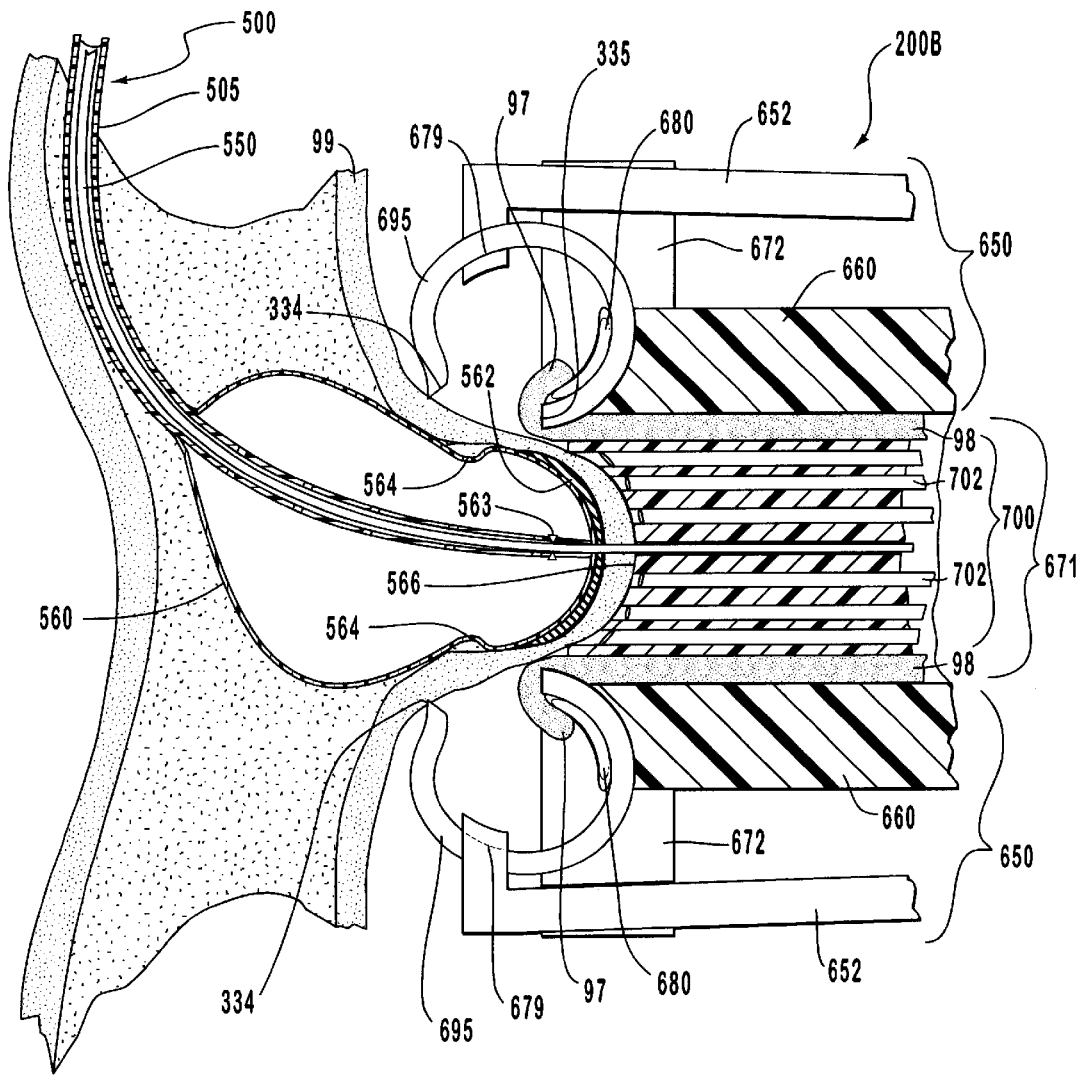
FIG. 17C shows a cross sectional view of the embodiment of the intraluminally directed anvil apparatus shown in FIGS. 17A–17B while being operated in conjunction with a spring clip anastomosis device.

Another example of an anastomosis device is shown in FIGS. 17C–17K as a peripheral device 200B hereinafter referred to as a "spring clip anastomosis device" whose primary components comprise laser device 700, and clipping device 650, which in turn includes holding arms 652, sleeve 660, guiding element 670, and memory clips 695. FIG. 17C shows the general disposition of catheter 500 with positioning wire 550 and balloon anvil 560 and spring clip anastomosis device 200B at the anastomosis site.

Figure 17D:
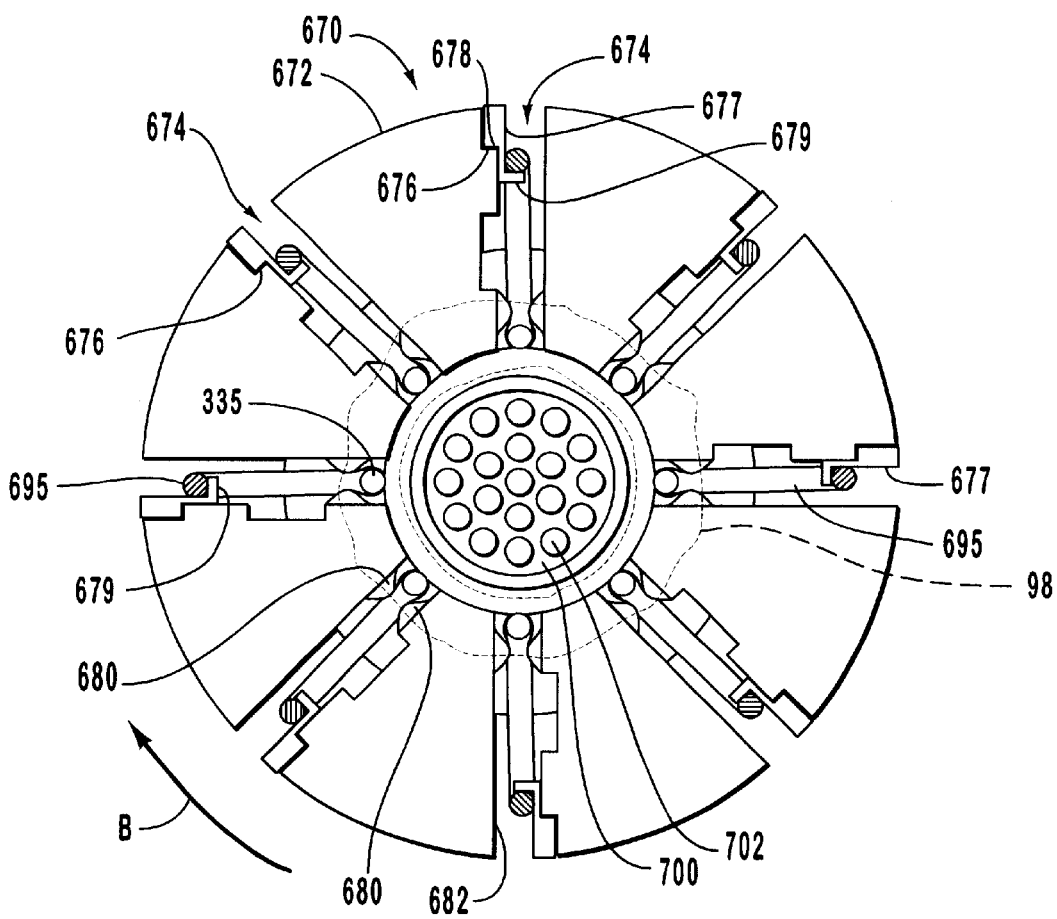
FIG. 17D shows a front view along the logitudinal axis of an embodiment of a spring clip anastomosis device like that shown in FIG. 17C.
Figure 17E:
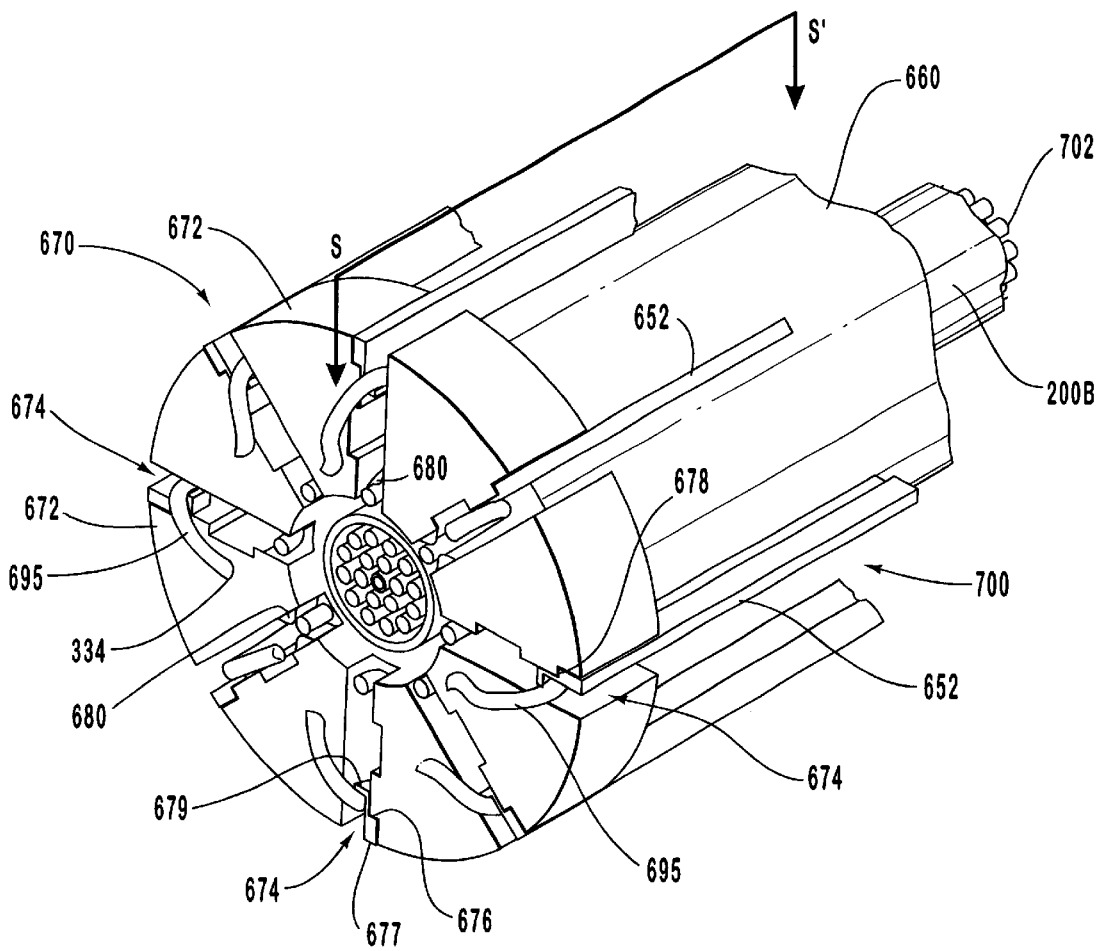
FIG. 17E shows a perspective view of the embodiment depicted in FIG. 17D. Plane S–S' represents the plane along which the cross sectional views shown in FIGS. 17C, 17F–17I are taken.
Figure 17F:
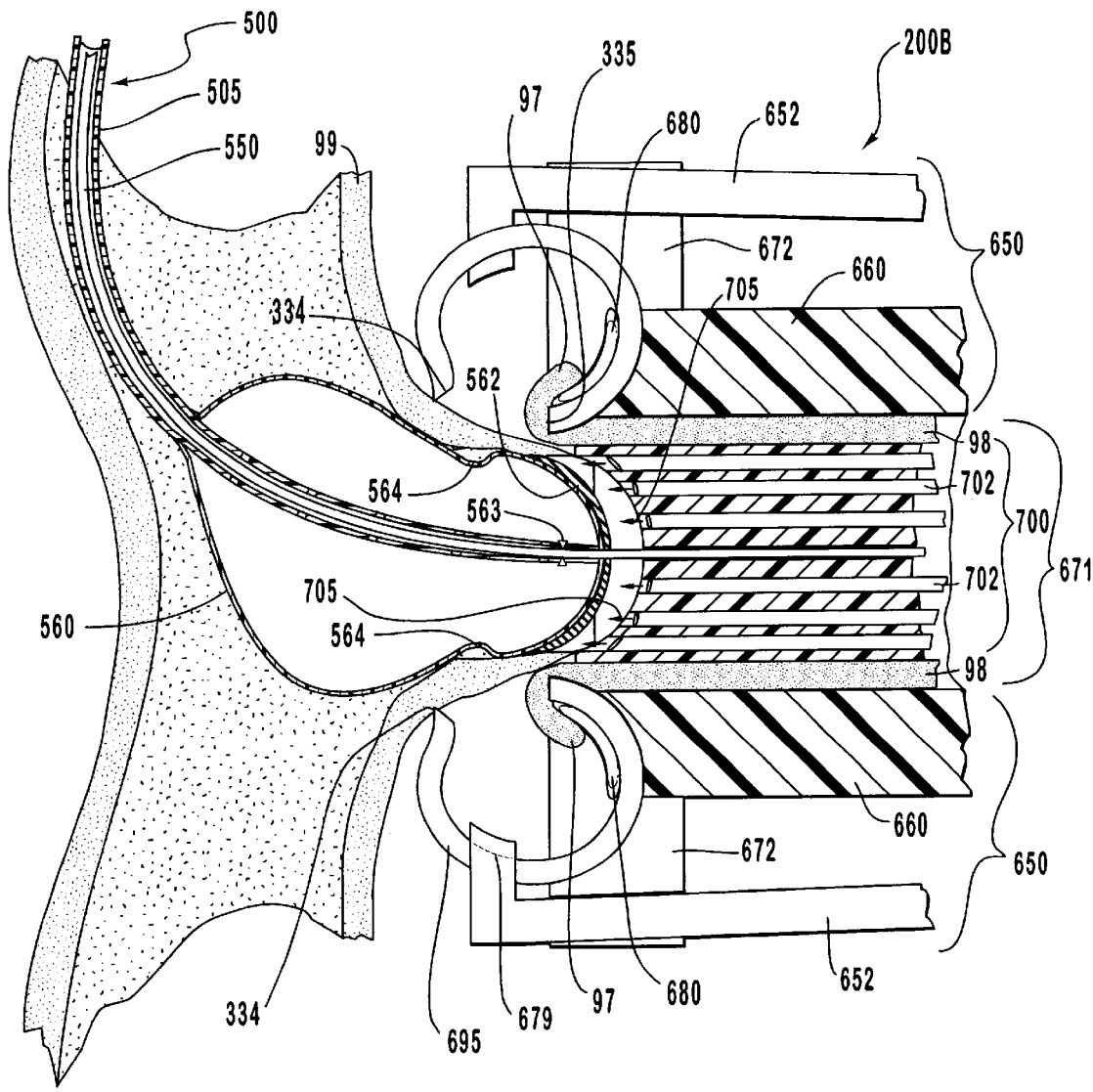
FIG. 17F is a cross sectional view analogous to that shown in FIG. 17C while the anastomosis fenestra is being opened with a laser device, where the cross section is taken along the plane S–S' shown in FIG. 17E.

As shown in FIGS. 17D–17E, guiding element 670 comprises at its anastomosis end a series of sectors 672 which are radially disposed around the periphery of longitudinally extending central lumen 671; sectors 672 are separated by slots 674 that are also radially arranged around the periphery of longitudinally extending central lumen 671. Preferably the number of sectors and corresponding slots is eight as shown in FIG. 17D–17E, but other embodiments can have less than or more than eight sectors and corresponding slots.

A ledge 676 in each sector 672 provides support for a holding arm 652 whose holding end 677 is preferably so shaped as to provide a mating feature 678 with corresponding ledge 676. This mating feature 678 can be shaped like a ledge that is complementary to ledge 676 as shown in FIGS. 17D–17E, or as a tooth, lip, flange or any other protuberance that can provide detachable contact engagement with ledge 676. Analogously, ledge 678 can have contact engagement with a feature such as a tooth, lip, or flange in sector 672 that is equivalent to ledge 676 and provides detachable contact engagement with ledge 678.

Holding end 677 extends generally radially towards the anastomosis site along and within slot 674 to form holding lug 679. Each sector 672 is provided with at least one protuberance 680 or an equivalent feature thereof that is located on the same side 682 as the ledge 676. Two of such protuberances are shown in each slot 674 in FIG. 17D. Protuberance 680 can be shaped as a flange, lip, elongated lug, handle, or any similar protruding feature. With holding end 677 of holding arm 652 in contact engagement with sector 672 at ledge 676, lug 679 and protuberances 680 preferably hold memory clip 695 in a distended position as shown in FIGS. 17D–17E. In another embodiment, memory clip 695 can be provided with a notch or a similar feature for detachable contact engagement with lug 679 or any equivalent feature to lug 679 at holding end 677. An embodiment of memory clip 695 is shown in FIG. 16H, with memory prongs 333, and preferably partially penetrating end 334 and pinching end 335.

Holding arm 652 is spring loaded, so that upon turning holding arms 652 as shown by arrow B (or by turning guiding element 670 in the sense opposite to that shown by arrow B) in FIG. 17D, holding end 677 falls off ledge 676, thereby disengaging arm 652 from sector 672 and releasing the prong that ends at partially penetrating end 695 of memory clip 334. When this operation takes place, each one of the memory clips placed in slots 674 is simultaneously released in the same manner.

Subsequent to, prior to, or simultaneously with the release of memory clip 695, optical fibers 702 deliver radiation that opens the anastomosis fenestra in receiving blood vessel 99, as shown in FIG. 17E by arrows 705. In the particular embodiment shown in FIG. 17E, the opening of the anastomosis fenestra is being performed prior to the release of memory clips 695.

Figure 20:
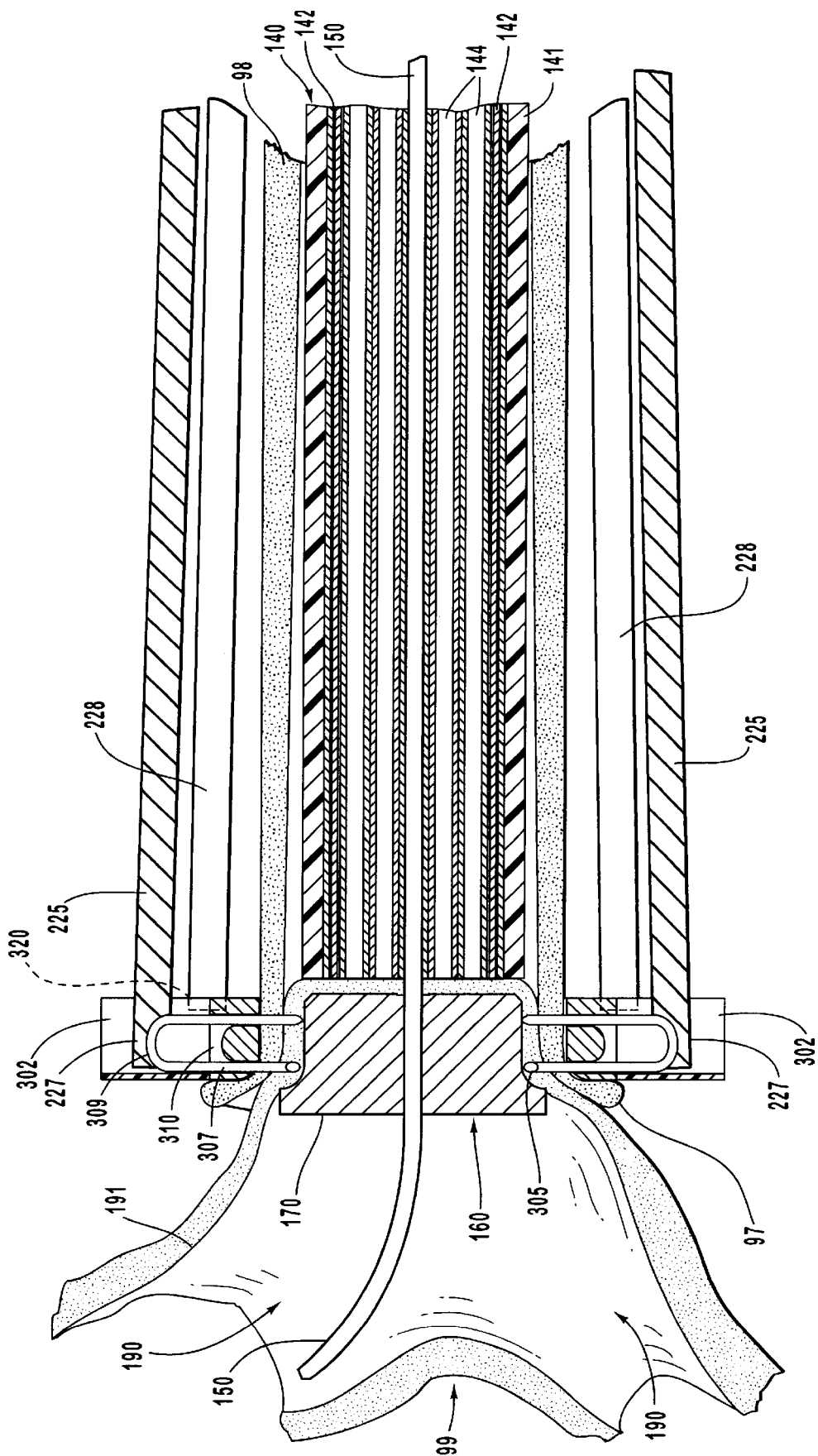
FIG. 20 shows a longitudinal cross sectional view in which the cutter and centering core shown in FIG. 8 have been replaced by a laser device .

Embodiments of laser device 700 generally have a configuration similar to that of laser device 400 as shown in FIG. 20. The embodiment of laser device 400 as shown in particular in FIGS. 17C–17J extends coaxially along and within sleeve 660 and it comprises a plurality of lumens for optical fibers 702, for piercing wire 554, and optionally for a connection (not shown) to a vacuum pump or vacuum line. The space between sleeve 660 and laser device 700 defines longitudinally extending lumen with an annular cross-section that is configured for receiving graft vessel 98 as shown in FIGS. 17C–17H.

Figure 17G:
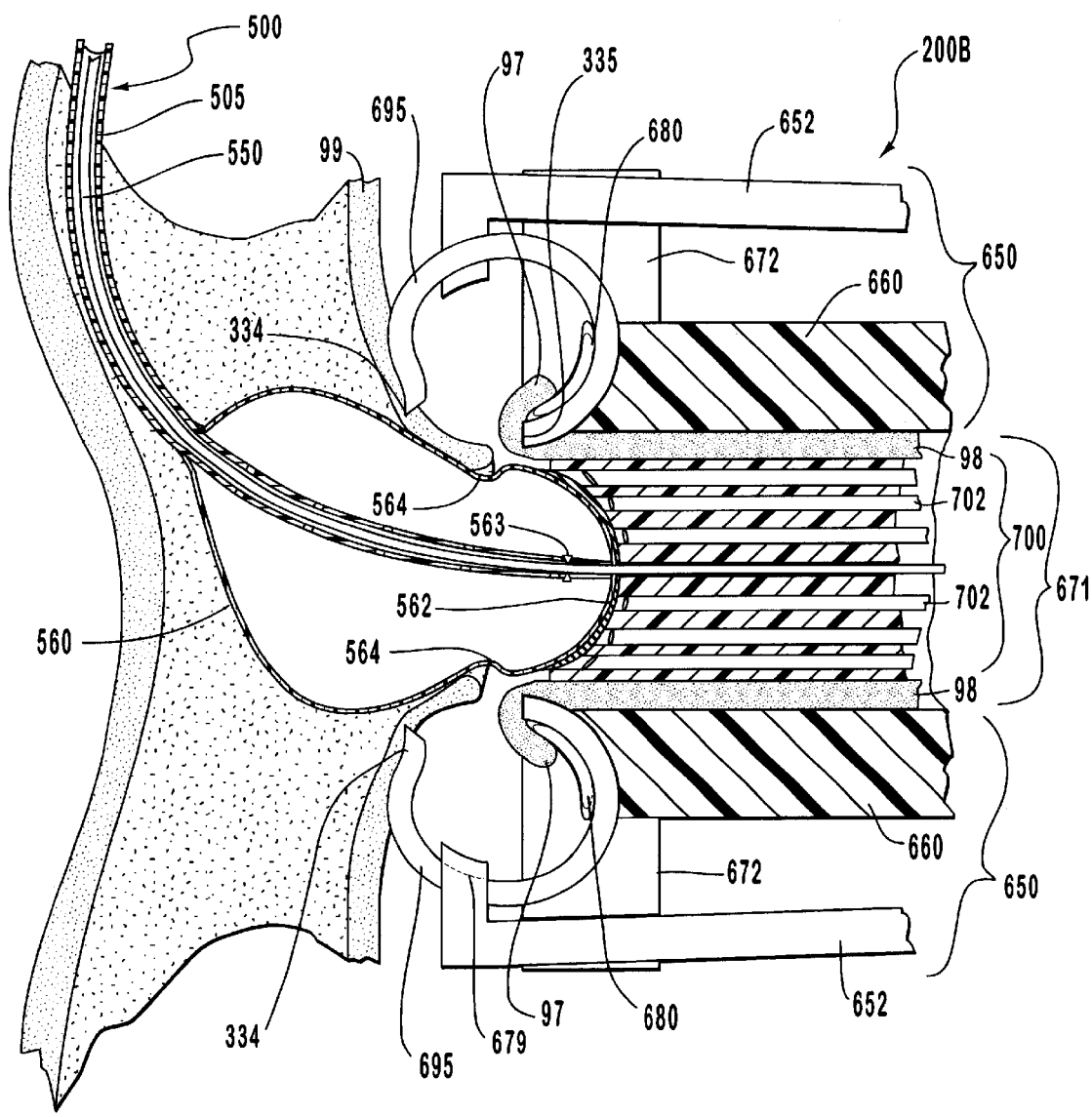
FIG. 17G is a cross sectional view analogous that shown in FIG. 17F with an anastomosis fenestra in the receiving blood vessel.
Figure 17H:
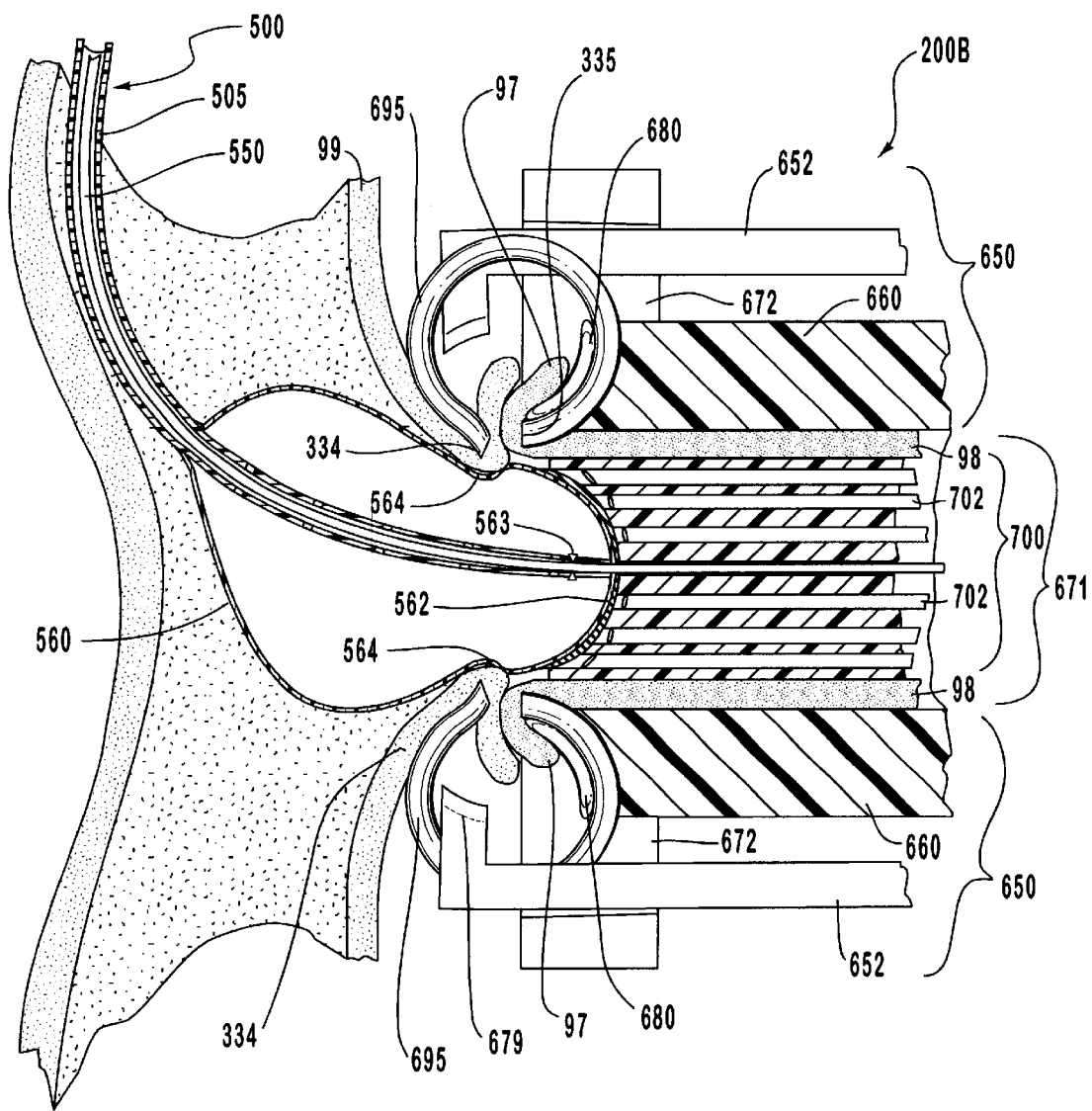
FIG. 17H is a cross sectional view analogous that shown in FIG. 17G with the spring clips holding together the receiving blood vessel and the graft vessel.
Figure 17I:
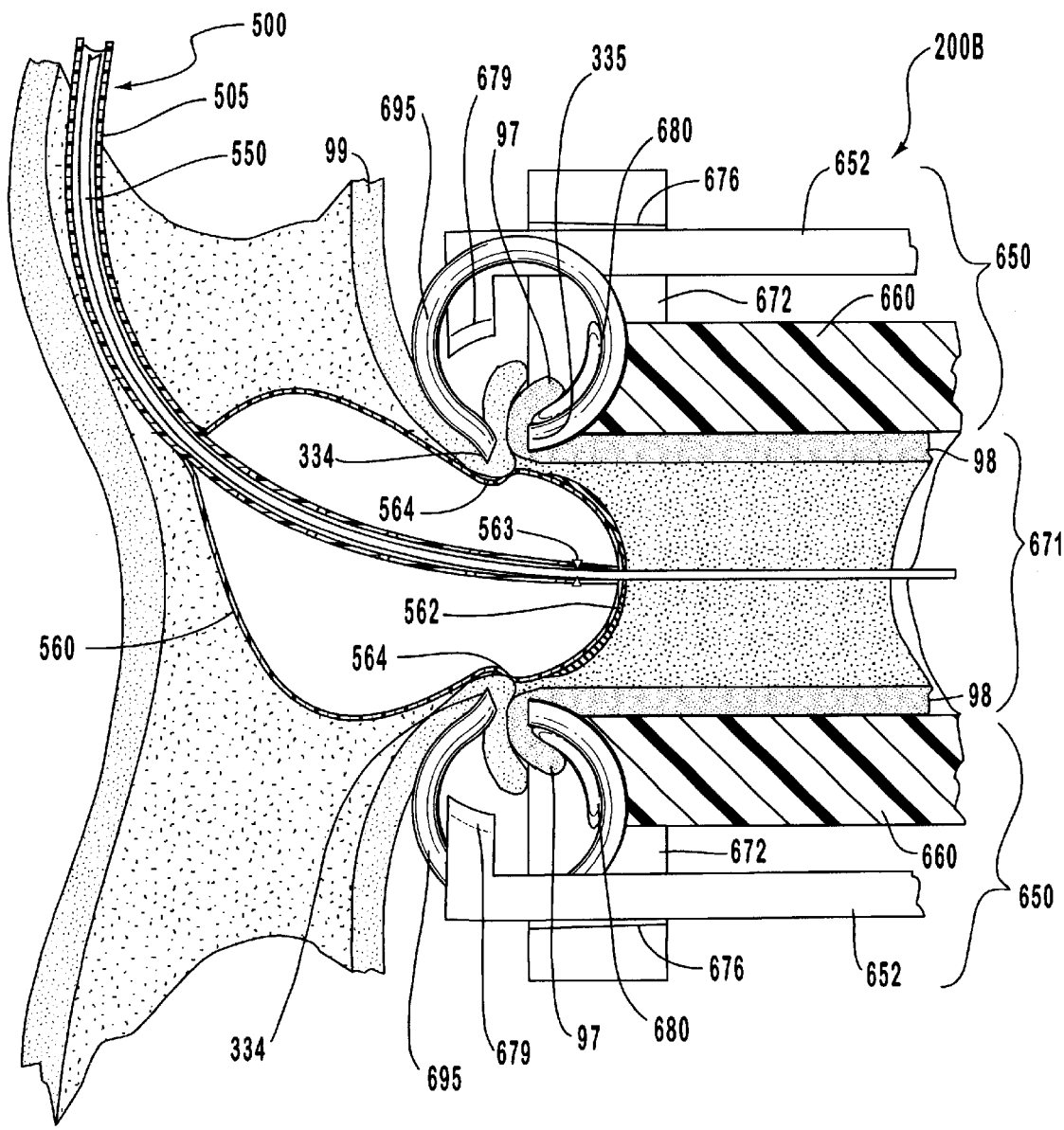
FIG. 17I is a cross sectional view analogous to that shown in FIG. 17H after the laser device has been removed from the anastomosis site.

The end of graft vessel 98 that is to be anastomosed is held in place in spring clip anastomosis device 200B by pinching ends 335 of memory clips 695 and protuberances 680 as shown in FIGS. 17C–17H. Upon rotation of holding arms 652 as indicated by arrow B in FIG. 17D (or upon rotation of guiding element 670 in the sense opposite to that indicated by arrow B), the removal of protuberances 680 from the space between memory clips 695 and partially everted end 97 of graft vessel 98 allows memory clips 695 to pinch or clip graft vessel 98 as memory clips 695 are restored to their equilibrium configurations. In the embodiment shown in FIGS. 17D–17E, each memory clip 695 slides past each corresponding pair of protuberances 680. In an embodiment with only one protuberance 680 in each slot 674 (not shown in FIGS. 17D–17E), each memory clip 695 slides past the corresponding protuberance 680. This change from the distended configuration of memory clip 695 shown in FIGS. 17C–17F to its restored equilibrium configuration is illustrated in FIGS. 17G-17I, which show holding arms 652 at different stages of their movement towards the anastomosis site while memory clips 695 bring in tight contact engagement the intima of receiving blood vessel 99 and the inner surface of graft vessel 98. This tight contact engagement is achieved in this particular embodiment by the restoring force of memory clip 695, and by the holding provided by partially penetrating end 334 and pinching end 335 of memory clip 695.

FIGS. 17C–17D, 17F–17I do not show the remaining features of sleeve 660 and holding arms 652 because these features are analogous to corresponding features of the embodiment shown in FIGS. 8, 10–12, and 15C. In addition, some of these features are partially shown in FIG. 17E.

Figure 17J:
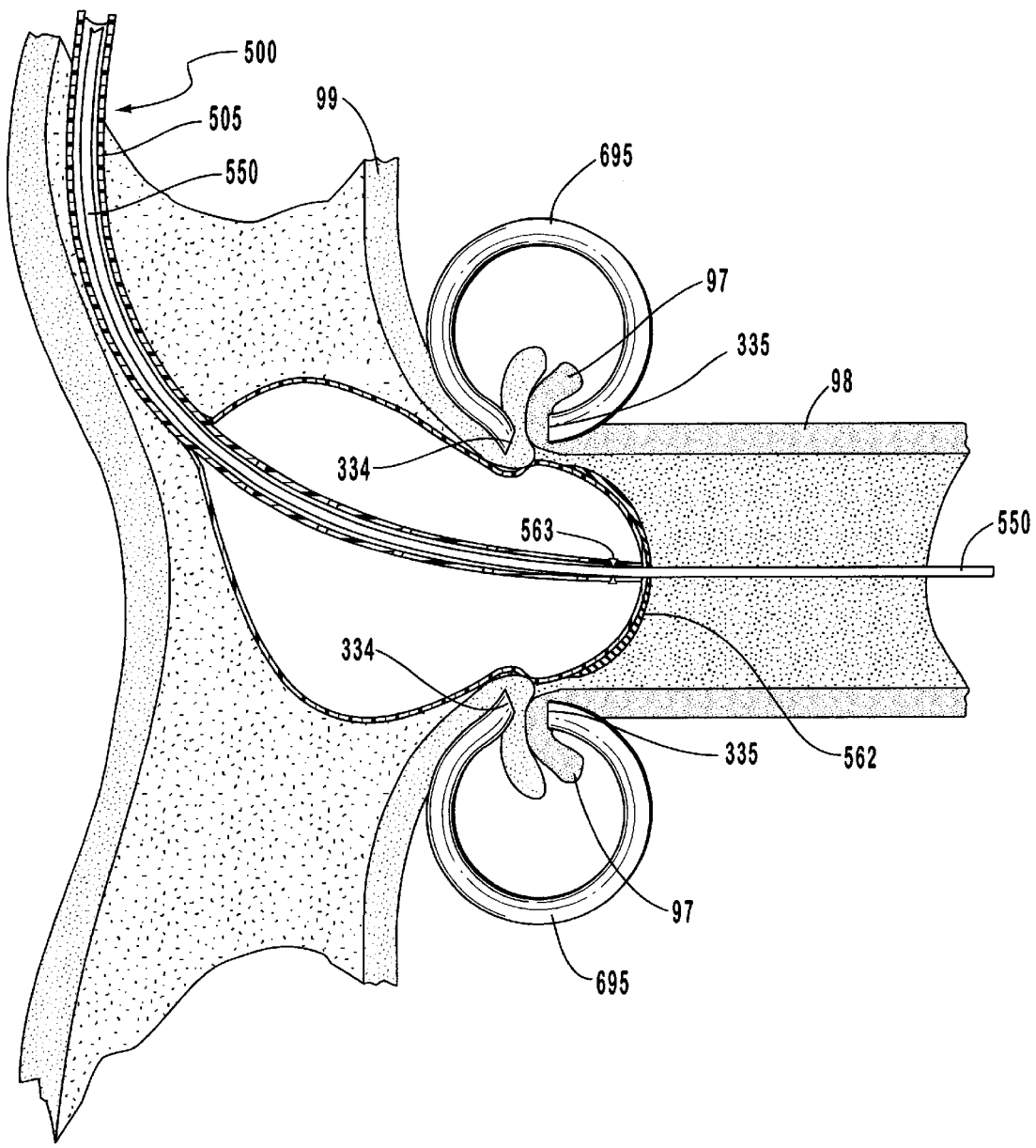
FIG. 17J is a cross sectional view analogous to that shown in FIG. 17I after the entire spring clip anastomosis device has been removed from the anastomosis site.
Figure 17K:
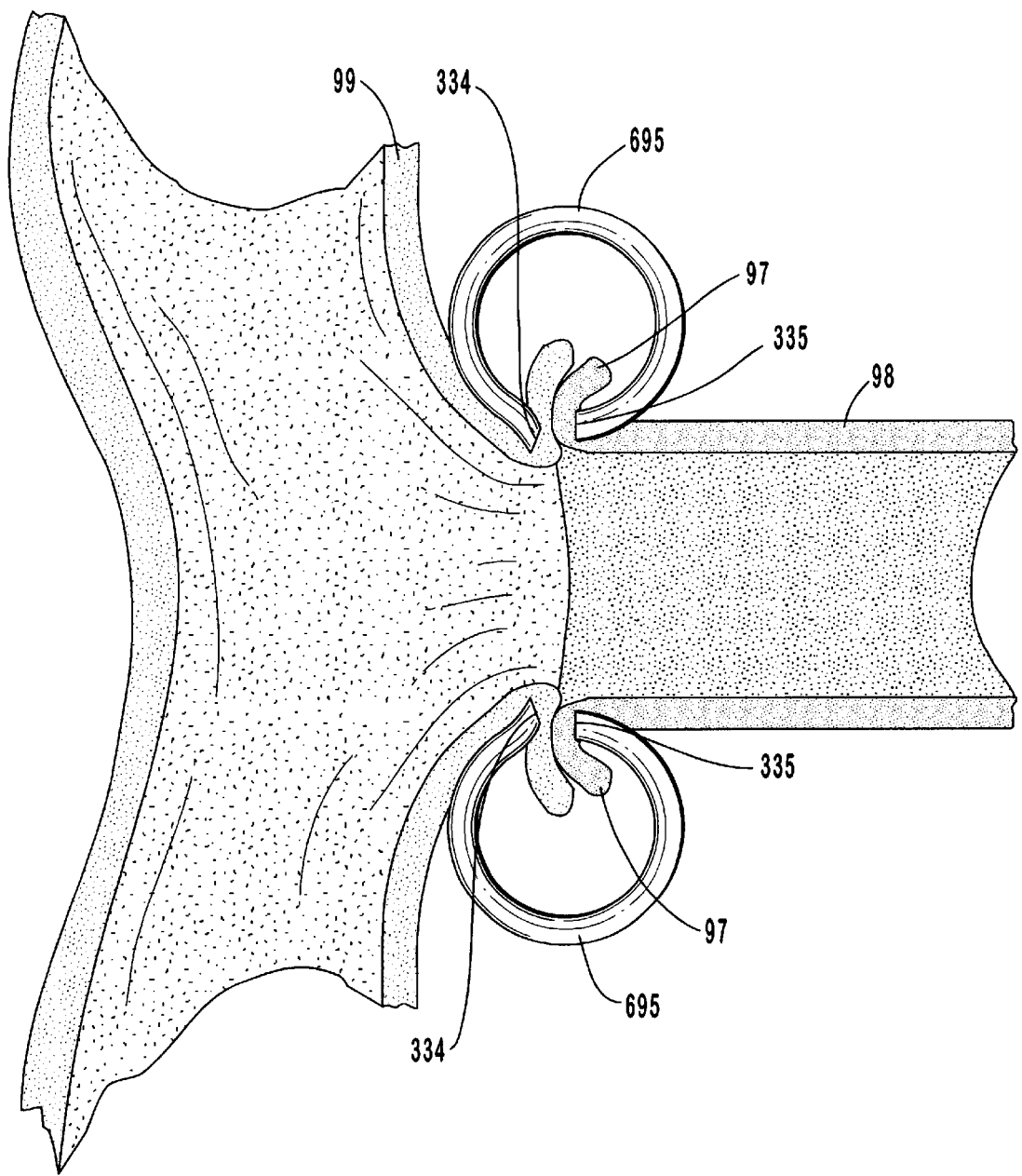
FIG. 17K is a cross sectional view of two structures that have been anastomosed with the intraluminally directed anvil apparatus and the spring clip device of this invention.

After memory clips 695 have been released and they effectively clip the anastomosed structures in tight contact engagement as shown in FIG. 17I, spring clip anastomosis device 200B is pulled away from the anastomosis area which is left as shown in FIG. 17J. The end of graft vessel 98 opposite to end 97 is then further joined, for example, in a subsequent anastomosis, or it is treated according to the practice of the procedure being performed. Once graft vessel 98 is in the desired final configuration, balloon anvil 560 is deflated and extracted together with catheter apparatus 500, leaving eventually the anastomosis site as shown in FIG. 17K. Piercing wire 554 can be extracted at any convenient time after the anastomosis fenestra has been opened and graft vessel 98 has been joined to receiving blood vessel 99 with memory clips 695.

Signaling of the appropriate anastomosis site and the anastomosis itself with the embodiments of this invention can be performed without interruption of blood flow within receiving blood vessel 99. In addition, the methods, systems and apparatuses of this invention do not require a 180° eversion of the end of the graft vessel being anastomosed, but at most partial eversion is only needed.

EXAMPLES OF THE PREFERRED EMBODIMENTS

Several examples of the present invention are presented as merely illustrative of some embodiments of the present invention. These examples are not to be construed as limiting the spirit and scope of the invention as these hypothetical examples were produced in furtherance of reducing the present invention to practice.

Example 1

In common hemodialysis practice, an artery is shunted to a vein with a vessel that channels the blood flow from the artery to the vein. This vessel is anastomosed at one end to the artery and at the other end to the vein, and it is used in hemodialysis for extracting and subsequently injecting the blood that is dialyzed. Embodiment 200A is used for anastomosing the ends of the vessel that provides the artery-to-vein shunt.

More particularly, only one end or both ends of the graft vessel can be anastomosed with embodiment 200A. When the graft vessel is anastomosed at both of its ends with embodiment 200A, an end of a graft vessel is anastomosed to the receiving blood vessel while the other end is left open, and another graft is similarly anastomosed at a different site of the receiving blood vessel. The open ends are then joined with a sleeve according to standard practice.

Example 2

Embodiment 200B is also used for anastomosing structures to facilitate hemodialysis in similar fashion as disclosed in Example 1 regarding embodiment 200A. Embodiment 200B, however, relies on clips that do not penetrate the walls of the anastomosed structures and consequently are not exposed to the blood flow, a feature that should minimize the risk of clot formation.

Example 3

To describe this exemplary embodiment of anastomosis device 200 of this invention, reference is made to FIGS. 8–14. In this embodiment, staple engaging device 219, activation sheath 233, staple guide ring 300 with staples 308, and anastomosis ring 350 in the embodiments shown in FIGS. 8–14 are replaced by hand suturing or by a suturing device such as the suturing device disclosed for example in U.S. Pat. No. 5,860,992 which has been herein incorporated by reference in its entirety. The anvil of this invention, such as anvil 160, provides an abrasion resistant surface that deflects the sharp end of a suturing needle.

Suturing is a technique that has been practiced for a long time, and its features and characteristics are fairly well known. When compared to one of the anastomosis devices herein disclosed, however, suturing sometimes requires a more invasive procedure, it requires comparatively more intensive and specialized training, and it does not provide for the standardization that would enable a broader group of practitioners to utilize it.

Example 4

To describe this exemplary embodiment of anastomosis device 200 of this invention, reference is made to FIGS. 8–14, 15A–15H and 18. In this embodiment, graft vessel 98 is joined to receiving blood vessel 99 with the aid of laser welding. Laser radiation such as radiation from a Nd-YAG laser is preferably delivered circumferentially for heating at sub-porization temperatures to smooth, seal, or weld the structures to the anastomosed.

It is known that a correlation exists between thermal weld strength and adventitial tissue temperature. Moreover, an incremental ramped laser dosimetry has been developed to maintain tissue temperatures within an appropriate range. See, for example, *Cardiovascular Applications of laser Technology*, p. 11.

When the anastomosis fenestra is opened with the relevant components of an embodiment as shown in FIGS. 8–14 and 15A–15H, with any of their equivalents or with an embodiment according to any of the relevant Examples herein discussed, laser welding with one of the embodiments of this Example can be used in addition to or instead of the use of mechanical devices such as staples, clips, or sutures. Alternatively, welding with an embodiment according to this Example can be performed prior to the opening of the anastomosis fenestra.

For example, the welding of the edge of the anastomosis fenestra to the inner wall of graft vessel 98 can be used to supplement a significantly reduced number of mechanical devices such as staples, clips, or sutures. This welding could in fact be the only anastomosis joint when receiving blood vessel 99 and graft vessel 98 are such that welding provides the necessary seal for the anastomosis. An advantage of the embodiment according to this Example is that welding requires no eversion of the end of graft vessel 98 to be anastomosed. Additionally, laser welding provides a seal between the two vessels.

After the anastomosis fenestra has been opened in the wall of receiving vessel 99 by a mechanical device such as cutter 213, centering core 207 and cutter 213 are pulled away from the anastomosis site and a laser welding device is inserted in their place until the terminal end of this device is placed near the edge of the anastomosis fenestra. Welding can then proceed by administering the appropriate dosage of laser radiation.

Figure 18:
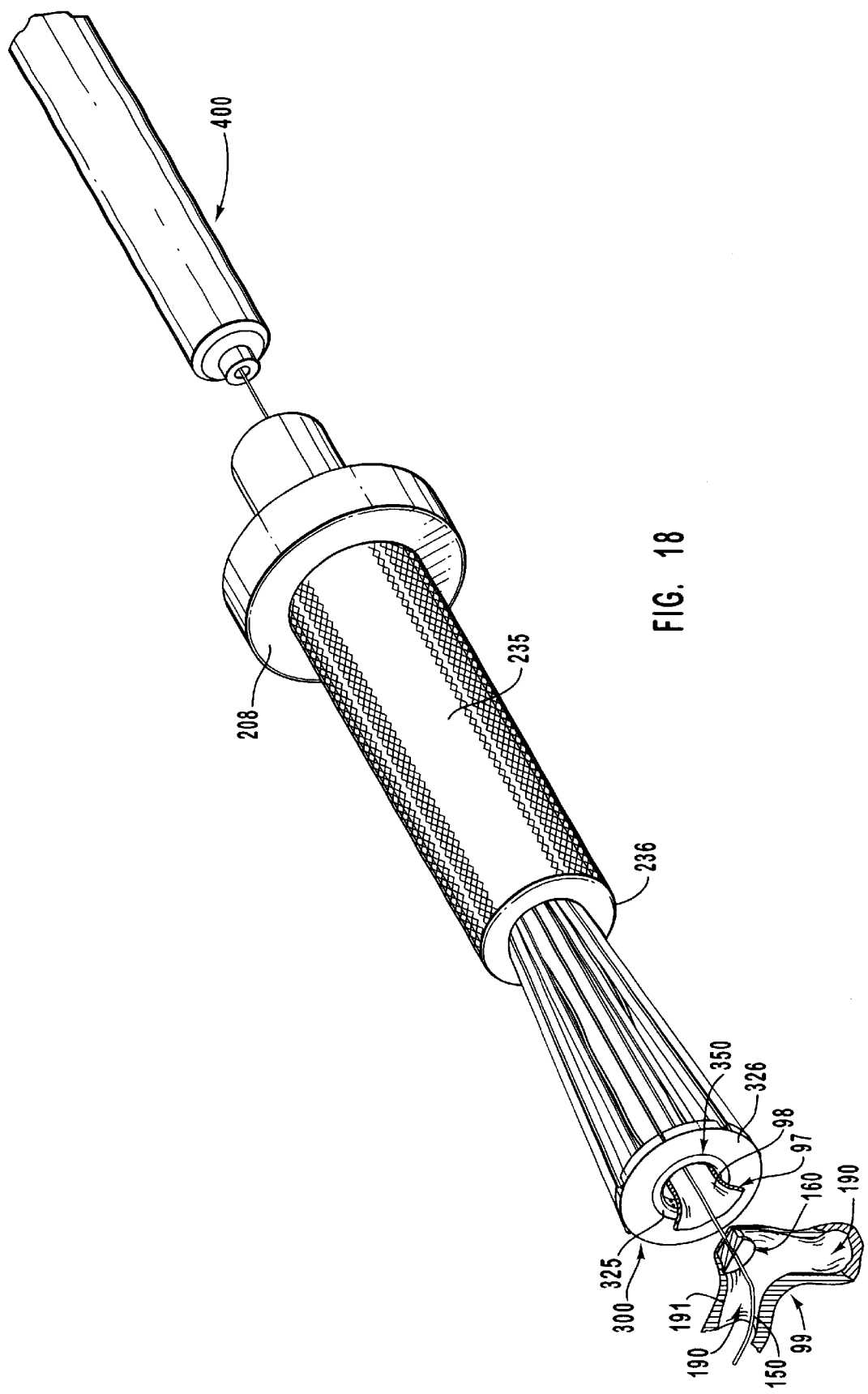
FIG. 18 is a perspective view of the embodiment shown in FIG. 8 where the cutter and centering core have been replaced by a laser device.
Figure 19:
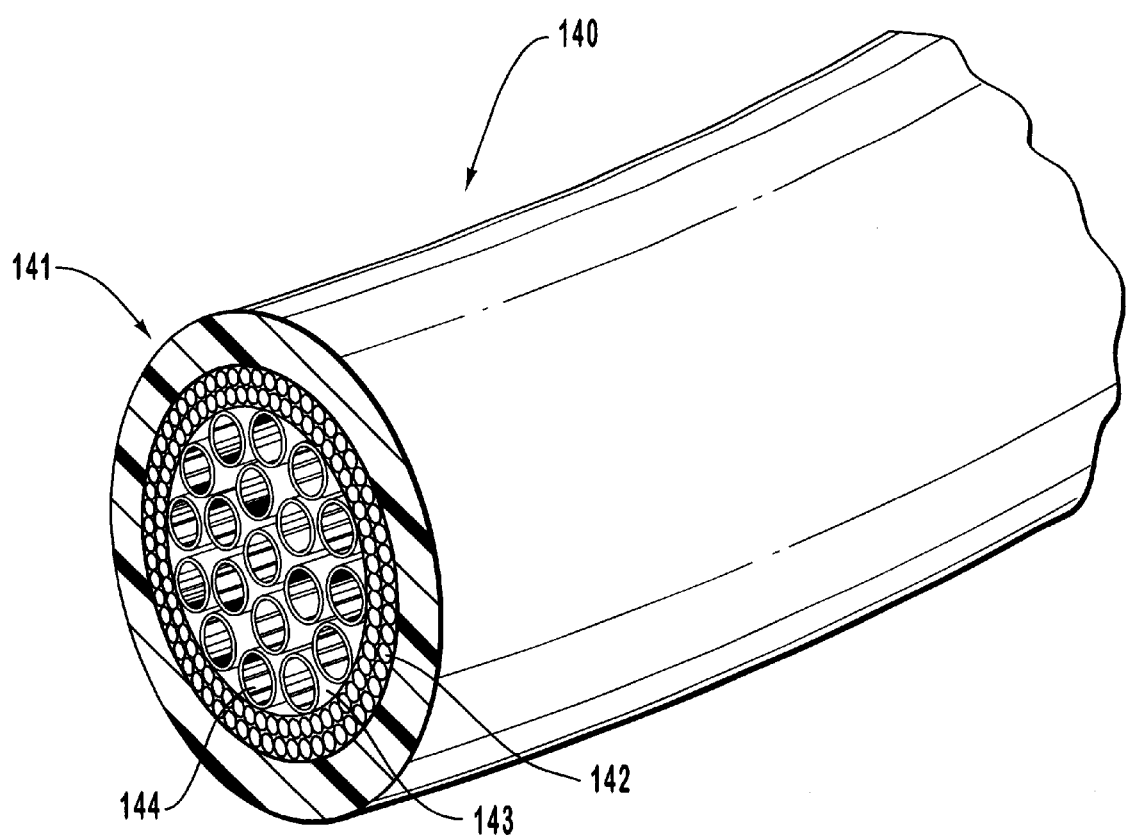
FIG. 19 shows a partial perspective view of the distal end of an exemplary embodiment of a laser device like that generically shown in FIG. 18.

As shown in FIGS. 18 and 19, an embodiment 400 of a laser device according to this Example is generally and preferably configured like a catheter or like an endoscope with one or a plurality of lumens. In this Example, laser device 400 represents a laser welding device. It is understood that the laser device is preferably provided with a central and axially extending conduit analogous to conduit 205 for accommodating a wire such as wire 150. This conduit is hereinafter referred to as centering lumen.

When an embodiment of a laser welding device according to this Example entirely performs the anastomosis sealing, graft vessel 98 can be held as shown in FIG. 18 by a ring or by a cylindrical structure in a manner analogous to the way anastomosis ring 350 and staple guide ring 300 hold it in the embodiment shown in FIG. 18. Alternatively, an embodiment according to this Example can be provided with a peripheral lumen of annular cross-section extending along the length of an embodiment of laser device 400 such as that shown in FIG. 18, with the distal end of such lumen appropriately designed for holding graft vessel 98. Additionally, welding with an embodiment according to this Example can take place before the anastomosis fenestra is open, in which case centering core 207 and cutter 213 or an equivalent cutting device can be inserted in place of and subsequently to the use of laser device 400, as in the exemplary embodiment shown in FIG. 18.

Instrument characteristics, radiation dosages, and techniques for implementing laser applications for clinical welding are disclosed in *Cardiovascular Applications of Laser Technology*, p. 11; R. D. Jenkins and J. R. Spears, *Laser Balloon Angioplasty*, Circulation, Vol. 81 (Suppl. IV) (1990) pp. 101–108; *Laser Tissue Welding*, pp. 381–415; *Surgical Properties and Applications of Sealed-Off $CO_2$ Lasers*, pp. 231–239; *980 nm High Power Diode Laser in Surgical Applications*, pp. 227–230; Robert T. V. Kung, Robert B. Stewart, David T. Zelt, Gilbert J. L'Italien and Glen M. LaMuraglia, *Absorption Characteristics at 1.9 $\mu m$: Effect on Vascular Welding*, Lasers in Surgery and Medicine, Vol. 13 (1993) pp. 12–17; *Comparison of Laser Welding and Sutures in Vascular Anastomosis*, pp. 34–40; *Low Temperature Laser-Welded Vascular Anastomosis*, pp. 241–247, and *Heat Induced Tissue Fusion for Microvascular Anastomosis*, pp. 198–208, which are hereby incorporated by reference in their entirety.

It is understood that any of the embodiments of the anastomosis device that are disclosed in the discussion of exemplary embodiments of this invention can further include additional probes extending along the same lumen that is used for delivering the radiation or along another lumen in a suitable probe, whether the radiation is used for sealing, opening the anastomosis fenestra or for any other purpose. These additional probes include an infrared thermometer or any other type of device that is used for measuring temperature, imaging probes for direct visualization of the anastomosis site, light carriers for illuminating the anastomosis site, fiberoptic biosensors including transducer sensors, all-fiber sensors, and spectrometric sensors, probes such as those used in endoscopic photodynamic therapy, and mechanical devices such as forceps, cutters or retrievers of biological material.

The transducer biosensors further include optic biosensors which change their own optical properties according to the physical or chemical parameter being tested, such as temperature, pressure, chemical characteristics including pH, $O_2$ concentration, $CO_2$ concentration, glucose concentration, immunological agent concentration, and properties related thereto. All-fiber biosensors use modified tips which are sensitive because of core doping or cladding, or because of having a chemically modified fiber end. Parameters tested with all-fiber biosensors include temperature and pH and these biosensors are also used for immunological assays. Spectroscopic biosensors typically rely on measurements of reflectance, fluorescence or absorption for measuring concentration of substances such as $O_2$, for drug dosimetry, for reflux monitoring, and for pharmacokinetic measurements.

Instrument characteristics and designs for these additional probes are known in the art. For example, probes of this type have been disclosed in Frank D. D'Amelio, Steven T. DeLisi, and Anthony Rega, *Fiber Optic Angioscopes, Proceedings of SPIE-The International Society for Optical Engineering*, Vol. 494 (1984), pp. 44–51, (this article will hereinafter be referred to as "Fiber Optic Angioscopes"); *Optical Fibers in Biomedical Sensing*, pp. 233–245; D. A. Russell, P. Nadeau, R. H. Pottier, G. Jori, and E. Reddi, *A Comparison of Laser and Arc-Lamp Spectroscopic Systems for In-Vivo Pharmacokinetic Measurements of Photosensitizers Used in Photodynamic Therapy, in Laser Systems for Photobiology and Photomedicine*, edited by A. N. Chester, S. Martellucci, and A. M. Scheggi, pp. 193–199, Plenum Press (1991), and P. Spinelli, M. Dal Fante, and A. Mancini, *Endoscopic Photodynamic Therapy. Clinical Aspects, in Laser Systems for Photobiology and Photomedicine*, edited by A. N. Chester, S. Martellucci, and A. M. Scheggi, pp. 149–155, Plenum Press (1991), which are hereby incorporated by reference in their entirety.

It is further understood that when laser radiation is discussed in the context of the disclosed exemplary embodiments of this invention, pulsed lasers are included among the possible laser radiation sources.

Example 5

To describe the exemplary embodiment of anastomosis device 200 of this invention, reference is made to Example 4. In this embodiment, graft vessel 98 is joined to receiving blood vessel 99 with the aid of non-laser welding radiation, such as radio frequency radiant energy. Other than the source of radiation, the characteristic features of embodiments of these Examples are analogous to the features and modifications introduced in the embodiment shown in FIGS. 8–14, as discussed Example 4.

For a more detailed description of known features of this technique, reference is made to K. Yamashita, S. Satake, H. Ohira, K. Ohtomo, *Radiofrequency Thermal Balloon Coronary Angioplasty: A New Device for Successful Percutaneous Transluminal Coronary Angioplasty, JACC*, Vol. 23(2) (1994) pp. 336–340; D. B. Fram, L. D. Gillam, T. A. Aretz, R. V. Tangco, J. F. Mitchell, J. T. Fisher, B. W. Sanzobrino, F. J. Kiernan, S. Nikulasson, A. Fieldman, and R. G. McKay, *Low Pressure Radiofrequency Balloon Angioplasty: Evaluation of Porcine Peripheral Arteries, J. Am. Coll. Cardiol.* Vol. 21(6) (1993) pp. 1512–1521, which are hereby incorporated by reference in their entirety.

Because this Example relies on radiation, its performance is expected to be comparable to that of the preceding Example. The use of radiation for welding as disclosed in this Example or in the preceding Example may lead to a simpler anastomosis device because the number of mechanical parts is reduced, but in general clinical devices that deliver radiation are currently more expensive than counterparts that perform comparable tasks by mechanical mechanisms.

Example 6

To describe this exemplary embodiment of anastomosis device 200 of this invention, reference is made to FIGS. 8–15, 15A–15H, 18, 19, and 20. In this embodiment, the anastomosis fenestra is opened in the wall of receiving blood vessel 99 with the aid of radiation, such as laser radiation. FIG. 19 shows distal end 140 of an exemplary embodiment according to this Example that can generally and schematically be represented by laser device 400 shown in FIG. 18. Tip 141 exposes the ends of optical fibers 142 and grid 143 with openings 144. Optical fibers 142 are such that they deliver the appropriate radiation for effectively ablating the perimeter of a generally circular region from the outside of receiving blood vessel 99, thus cutting open the anastomosis fenestra. Openings 144 provide the suitable rarefaction for retaining by suction the fragments and any product resulting from the ablation, burning, or vaporization caused by the irradiation of the wall of receiving blood vessel 99. To this effect, openings 144 are the ends of a plurality of conduits, or the screened end of a single conduit, to a vacuum pump or a vacuum line.

When the anastomosis fenestra is opened with the relevant components of an embodiment as shown in FIGS. 8–14 and 15A–15H, with any of their equivalents, or with an embodiment according to any of the relevant Examples herein discussed, tip 141 of an embodiment according to this Example is brought near the anastomosis site in a fashion similar to that described in the foregoing discussion regarding centering core 207 and cutter 213 as illustrated in FIG. 18. In an operational mode, an embodiment as shown in FIGS. 8–14 is used with an embodiment according to this Example replacing centering core 207 and cutter 213 as shown in the cross-sectional view of FIG. 20. An embodiment according to this Example preferably has the general configuration and overall features of the embodiment shown in FIG. 18 as discussed in the context of Example 5.

Although not shown in FIG. 19, an embodiment according to this Example is preferably provided with a centering lumen. This is the lumen that is longitudinally occupied by wire 150 in the cross-sectional view shown in FIG. 20.

Instrument characteristics, radiation dosages, and techniques for implementing laser applications for clinical cutting or ablating are disclosed in *Fiber Optic Angioscopes*, pp. 44–51; *Cardiovacular Applications of laser Technology*, pp. 1–27; *Laser Angioplasty*, pp. 771–787; *Surgical Properties and Applications of Sealed Off $CO_2$ Lasers*, pp. 231–239; *Laser Tissue Interactions*, pp. 45–47 and 216–221; *Excimer Laser Angioplasty in Human Artery Disease*, pp. 69–72; R. A. Kirschner, *The Nd-YAG Laser-*

*Applications in Surgery*, in *Laser Systems for Photobiology and Photomedicine*, edited by A. N. Chester, S. Martellucci, and A. M. Scheggi, pp. 53–56, Plenum Press (1991); and *Nonocclusive Excimer Laser-Assisted End-to-Side Anastomosis*, pp. S138–S142.

The cauterizing effects of radiation may offer an advantage over mechanical cutters. As indicated in the discussion of the preceding Example, however, a mechanical cutter is expected to be currently less costly than a device that relies on radiation.

Example 7

To describe this exemplary embodiment of the anastomosis device of this invention, reference is made to Examples 4–6 and FIG. 20. In this embodiment, graft vessel 98 is joined to receiving blood vessel 99 with the aid of welding such as laser welding or non-laser welding discussed in Examples 4 and 5, and the anastomosis fenestra is opened with the aid of radiation such as laser radiation, as discussed in Example 6. An embodiment according to this Example preferably has the general configuration and overall features of laser device 400 shown in FIG. 18 as discussed in the context of Example 4. In this case, laser device 400 is preferably a multilumen probe that comprises radiation guides for cutting and for welding as discussed in Examples 4–6.

Consistent with the discussion of the preceding Examples, the use of radiation for joining the anastomosis structures and for opening the anastomosis fenestra can lead to a considerable simplification of the anastomosis device because of the significant reduction in mechanical and moving parts, but anastomosis devices that rely on radiation for joining the anastomosis structures and for opening the anastmosis fenestra are likely to be more expensive than mechanical counterparts.

Example 8

Figure 21:
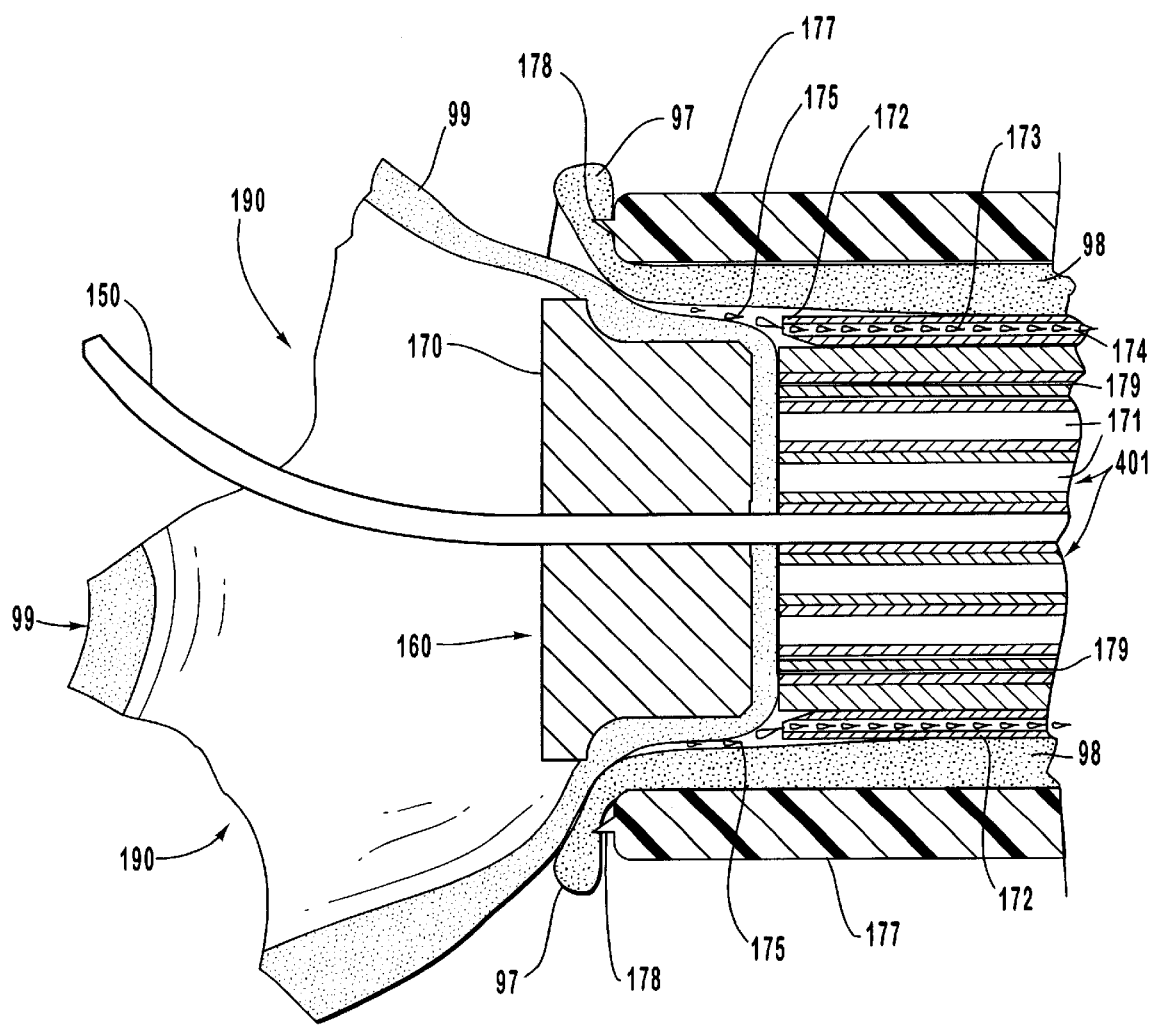
FIG. 21 shows a longitudinal cross sectional view analogous that shown in FIG. 20 with an applicator for a material such as solder or glue, and a different way of holding the end of the graft vessel to be anastomosed.

To describe this exemplary embodiment of the anastomosis device of this invention, reference is made to Examples 4 and 5 and FIG. 21. In this embodiment, a source of radiation such as a laser welding device as described in Example 4, is supplemented with a soldering material. A solder such as proteinaceous material is preferably applied to the site where receiving blood vessel 99 is to be joined to graft vessel 98 and then laser light is applied to seal the solder to the tissue surfaces. It has been reported that blood loss is reduced in human PTFE arteriovenous fistulae sealed with solder, *Laser Tissue Welding*, page 400.

Solders used in embodiments of this Example are preferably biological glues that are based on proteins. In one embodiment according to this Example, albumin is used as solder.

Solder can be applied to the anastomosis area with an applicator that is built into the laser welding device as shown in FIG. 21 or with an applicator that is separately handled. Whether built as part of a laser welding device or not, clinical solder applicators are devices which, like clinical glue applicators, are well known in the art.

In other embodiments of this Example, soldering is enhanced by photoenhancement. Photoenhanced laser soldering relies on a chromophore that is added to the solder to focus light absorption in the solder and thus avoid or reduce radiation damage to the anastomosed vessels. Indocyanine green is a preferred chromophore for enhancing vascular welding with near infrared diode laser.

An embodiment according to this Example preferably has the general configuration and overall features of laser device 400 shown in FIG. 18 as discussed in the context of Example 4 and it more specifically can be represented by laser device 401 shown in FIG. 20. In this case, laser device 400 can be supplemented with at least one lumen for a solder applicator. In particular, FIG. 21 shows a longitudinal cross section of an embodiment of the end of a laser device near the anastomosis site. In this exemplary embodiment, solder 173 is supplied through lumen 174 and it is directed by tip 172 to the contact region 175 between graft vessel 98 and receiving blood vessel 99. As more precisely described in other Examples, glue is delivered in one embodiment of this invention as solder 173 is delivered in the embodiment shown in FIG. 21. Device 179 can be one or a plurality of devices that radiation for cutting, sealing or soldering. Devices 171 represents a cross-sectional view of conduits 144 shown in FIG. 19 and discussed in Example 6, they represent in other embodiments of the invention the guides that deliver radiation for opening the anastomosis fenestra as discussed in Example 7, or, in still other embodiments, a combination of both.

FIG. 21 schematically illustrates an exemplary embodiment of a device that holds graft vessel 98 to be anastomosed. This is accomplished in the embodiment shown in FIG. 21 by tubular graft vessel holder 177 that has a feature or plurality of features that releasably hold graft vessel 98 near its end. In particular, this feature can be penetrating point 178, but it can be embodied by any other feature that detachably holds graft vessel 98.

Instrument characteristics, compositions, changes in tensile strengths, and techniques for implementing laser solder have been disclosed in *Laser Tissue Welding*, pp. 389–392, and in *Human Albumin Solder for Laser Tissue Welding*, pp. 577–580, publications which have been incorporated herein in their entirety by reference.

By combining the effects of radiation and that of solder, this Example illustrates a feature of the several mechanical, radiation-based and chemical devices discussed in the exemplary embodiments of this invention. This feature is the combination of several procedures in the practice of vascular anastomosis according to this invention. Consistently with this feature, a mechanical procedure that relies on staples, clips or suture can be combined with a radiation-based procedure or with a procedure that relies on chemical effects for joining anastomosed structures. The plurality of possible combinations used in opening the anastomosis fenestra and/or joining the anastomosed structures is not described in further detail because these combinations can be performed in light of this disclosure, preferred embodiments and illustrative Examples.

Example 9

To describe this exemplary embodiment of anastomosis device 200 of this invention, reference is made to Examples 6 and 7. Whether the anastomosis fenestra is opened with a mechanical device such as cutter 213 or with radiant energy such as with an embodiment according to Example 6, a biocompatible adhesive or glue can be used for sealing graft vessel 98 to receiving blood vessel 99. After or before the anastomosis fenestra is opened, glue is applied to the anastomosis area around the anastomosis fenestra with an applicator that is built into the device used for opening the anastomosis fenestra or with an applicator that is separately handled. Clinical glue applicators are devices that, whether designed to be handled separately or as a part of a mechanical or laser guide device, are well known in the art. In particular, glue can be delivered to the anastomosis area as solder is delivered and with applicators that are similar to those discussed in the context of Example 8. The exemplary embodiment of laser device 401 shown in FIG. 21 illustrates a possible embodiment according to this Example in which applicator 174 delivers glue rather than solder 173.

More specifically, the cross-sectional view of FIG. 21 schematically shows part of an embodiment according to this Example with a series of devices 171 for delivering radiation, an applicator 174 for delivering glue or solder 173, and graft vessel 98 held by penetrating point 178 within an annular lumen between graft vessel holder 177 and the anastomosis device of this Example. This annular lumen is an exemplary illustration of the annular lumen referred to in Example 4. Devices 171 for delivering radiation are preferably optical fibers for delivering laser radiation for opening the anastomosis fenestra. Applicator 174 for delivering glue or solder can comprise a cartridge (not shown) and an applicator mechanism (not shown) for releasing the glue or solder in a controlled manner. Partially everted end 97 of graft vessel 98 is preferably and temporarily held with the aid of attachment device 177 while the anastomosis is being performed. In a specific embodiment, the cartridge can be a suitably modified syringe similar to the preloaded syringes in which fibrin glue Tissucol is commercially available.

Instrument characteristics, compositions, and techniques for clinical sealing with glue have been disclosed in *Histoacryl Glue as a Hemostatic Agent*, p. 897; *Photopolymerizable Blood Vessel Glue*, pp. 901–907; *Telescoping and Glue Technique*, pp. 1401–1408; *Microvascular anastomosis With Minimal Suture and Fibrin Glue*, pp. 306–311; *Thrombogenic Effects of Fibrin Sealant on Microvascular Anastomoses*, pp. 415–419; and *Novel Vascular Sealing Device*, pp. 82–91.

The use of fibrin glue can have a dual purpose in the context of this invention because it can be used as an adhesive for sealing graft vessel 98 to receiving blood vessel 99 and alternatively, or in addition, it can be used for its properties as a laser shield to protect tissue from certain laser radiation. On the other hand, a number of glues that effectively join anastomosed structures do not offer the required degree of biocompatibility and can lead to tissue necrosis.

SUMMARY OF PREFERRED EMBODIMENTS

The elements of the embodiments of this invention disclosed hereinabove, equivalents thereof, and their functionalities can be expressed as means for performing specified functions as described hereinbelow.

Any one of a plurality of devices such as an anvil formed from a hard material such as tempered stainless steel, a laser shield anvil, a soft anvil, a balloon anvil, a combination of balloon and puncture resistant balloon sheath, an anvil with abrasion resistant material, an anvil with puncture resistant material, an anvil with distortion resistant material, and an anvil with an effective radiation absorbing material are exemplary embodiments of anvils. Note, however, that a tempered stainless steel anvil is preferred for ease of use. Additionally, each anvil is an example of anvil means for engaging the intima of the wall of a receiving blood vessel. Note that the balloon anvils disclosed herein are also examples of balloon anvil means for engaging the intima of a receiving blood vessel after being inflated.

The intraluminally directed anvil apparatus of this invention can have one or a plurality of access ports or luer fittings, and it can have one or a plurality of lumens. Additionally some embodiments of the intraluminally directed anvil apparatus can be utilized without a catheter tube to be moved within a blood vessel or other lumen to an anastomosis site.

Embodiments of the intraluminally directed anvil apparatus of this invention are provided with a positioning means for intraluminally positioning the anvil at the anastomosis site. Examples of this positioning means are provided by a positioning wire such as wire 152, by positioning shaft 182, and in embodiments of a balloon anvil with no positioning lumen such as balloon anvil 500, by positioning shaft 550. The positioning wire 152, positioning shaft 182, and positioning shaft 550 are also examples of a positioning stem.

Memory staples, memory clips, clips, staples with penetrating puncturing ends, staples with hooked puncturing ends, and staples with pre-bent prongs, staples with geometric modifications of the shapes thereof, and combinations thereof are exemplary embodiments of staple means for joining graft vessel 98 to receiving blood vessel 99 of this invention. Staple means, suture thread and combinations thereof are examples of means for mechanically joining graft vessel 98 to receiving blood vessel 99 of this invention.

Biocompatible adhesives or glue, solder, biological procoagulant solution, a combination of a chromophore and solder, and combinations thereof are exemplary embodiments of means for chemically joining graft vessel 98 to receiving blood vessel 99 of this invention.

Tissue welding radiation, such as laser radiation or radiofrequency radiation, the combination of substances and radiation for laser sealing, and combinations thereof are exemplary embodiments of radiation-based means for joining graft vessel 98 to receiving blood vessel 99 of this invention.

Means for mechanically joining graft vessel 98 to receiving blood vessel 99, and combinations thereof, means for chemically joining graft vessel 98 to receiving blood vessel 99, and combinations thereof, radiation-based means for joining graft vessel 98 to receiving blood vessel 99 of this invention and combinations thereof, and combinations of such mechanical means, such chemical means, and such radiation-based means for joining graft vessel 98 to receiving blood vessel 99 are exemplary embodiments of the means for joining graft vessel 98 to receiving blood vessel 99 of this invention.

Circumferential staple guide rings, non-circumferential staple guide rings, orthogonal staple guide rings, non-orthogonal staple guide rings, pre-loaded anastomosis rings, and combinations thereof are exemplary embodiments of the staple guide means for guiding staple means of this invention.

Circumferential anastomosis rings, orthogonal anastomosis rings, non-circumferential anastomosis rings, non-orthogonal anastomosis rings, pre-loaded anastomosis rings, and combinations thereof are exemplary embodiments of the anastomosis ring means for maintaining an end of a graft vessel in a desired position for end-to-side anastomosis. Permanent anastomosis rings, biocompatible dissolvable anastomosis rings, and removable anastomosis rings are also examples of such anastomosis ring means. However, permanent anastomosis rings are also examples of anastomosis ring means for maintaining an end of a graft vessel in a desired position and for providing support around the opening formed in the receiving blood vessel after the end of the graft vessel is attached to the receiving blood vessel at the anastomosis site.

Graft vessel holding tubes as discussed in Examples 8 and 9 are examples of tubular graft vessel holding means for holding an end of a graft vessel in a desired position for end-to-side anastomosis. Such holding tubes are particularly useful when joining is achieved by chemical means or radiation-based means for joining a graft vessel to a receiving blood vessel. Such graft vessel holding tubes as well as anastomosis rings are examples of graft vessel holding devices. Additionally, tubular graft vessel holding means and anastomosis ring means are both examples of graft vessel holding means for holding an end of a graft vessel in a desired position for end-to-side anastomosis.

Embodiments of the attachment means for attaching the wall of the receiving blood vessel to the end of the graft vessel of this invention include staple delivery means for delivering staple means such as the staple devices disclosed herein for joining the graft vessel to the receiving blood vessel; means for suturing an end of the graft vessel to the wall of the receiving blood vessel such as the suturing devices disclosed herein; means for clipping an end of the graft vessel to the wall of the receiving blood vessel such as the clipping devices disclosed herein; means for radiation welding an end of the graft vessel to the wall of the receiving blood vessel such as the devices for radiation welding disclosed herein and in particular the laser welding devices disclosed in Example 4 and radiofrequency radiation welding devices disclosed in Example 5; means for laser sealing an end of the graft vessel to the wall of the receiving blood vessel such as the laser sealing devices disclosed herein; means for soldering an end of the graft vessel to the wall of the receiving blood vessel such as the devices for soldering disclosed in Example 8; and means for gluing an end of the graft vessel to the wall of the receiving blood vessel such as the devices for gluing disclosed herein.

Centering core 207, a centering lumen, an axially extending tube, guide or any other similar passage that provides a housing for extending the piercing wire therethrough and, in general, a conduit disposed for receiving the wire of this invention are exemplary embodiments of the centering means for centering the staple delivery means over the anastomosis site by receiving the piercing wire of an intraluminally directed anvil apparatus.

Cutter 213 and devices that deliver radiation for opening the anastomosis fenestra as disclosed in Examples 4–5, and 7; combinations of a cutter and such devices are exemplary embodiments of the cutting means for forming an opening in the wall of the receiving blood vessel of this invention.

As indicated hereinabove, a staple delivery device is an example of staple delivery means for delivering staple means for joining graft vessel 98 to receiving blood vessel 99. The staple delivery means comprises staple engaging means for engaging the staples and activation means for acting on the staple engaging means to enable the staple engaging means to push the staples through the end of the graft vessel, through the receiving blood vessel around the opening in the receiving blood vessel, and through the anastomosis ring means. Staple engaging device 219 and functionally corresponding mechanisms are exemplary embodiments of the staple engaging means for engaging staples.

Activation sheath 233 and functionally corresponding parts in staple delivery devices are exemplary embodiments of the activation means for acting on the staple engaging means of this invention.

Exemplary embodiments of the means for anastomosing the wall of the receiving blood vessel with the end of a graft vessel according to this invention are provided by the set comprising attachment means and cutting means; by the set comprising attachment means, cutting means and centering means; by the set comprising staple delivery means, centering means, anastomosis ring means, and cutting means; by the set comprising clipping means, centering means and cutting means; by the set comprising suturing means, centering means, and cutting means; by the set comprising radiation welding means, centering means and cutting means; by the set comprising laser sealing means, centering means and cutting means; by the set comprising soldering means, centering means and cutting means; by the set comprising gluing means, centering means, and cutting means; and by any of the previously discussed embodiments with additional probes such as sensors and mechanical devices such as forceps, cutters and extractors.

The exemplary embodiments shown in FIGS. 1–21 and disclosed in the preceding discussion are not meant to be mutually exclusive. On the contrary, features of these exemplary embodiments can be suitably combined to generate embodiments of intraluminally directed anvil apparatus and of anastomosis means that are additional exemplary embodiments of the present invention. These additional combinations, however, can be performed with the aid of the objectives and teachings herein contained and ordinary skills in the art; thus no other combinations are offered as additional explicit examples.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by united states letters patent is:

1. An anastomosis apparatus for use with an intraluminally directed anvil apparatus, the anastomosis apparatus comprising:

attachment means for attaching an end of a graft vessel to a wall of a receiving blood vessel;

centering means for centering the anastomosis apparatus over an anastomosis site by receiving a piercing wire extending from an anvil of an intraluminally directed anvil apparatus and then engaging the piercing wire to enable the wall of the receiving blood vessel to be moved as needed at an anastomosis site as the intraluminal directed anvil apparatus is moved via the anastomosis apparatus; and cutting means for forming an opening in the wall of the receiving blood vessel at the anastomosis site through engagement with the anvil of the intraluminally directed anvil apparatus after the centering means has received and engaged the piercing wire, such that the opening is generally cylindrical, generally corresponds with the circumference of the end of the graft vessel and is centered on the piercing wire.

2. An anastomosis apparatus as claimed in claim 1, wherein the cutting means is a cutter.

3. An anastomosis apparatus as claimed in claim 1, wherein the cutting means is a device that delivers radiation.

4. An anastomosis apparatus as claimed in claim 1, wherein the attachment means is a staple delivery means for delivering staple means for joining the graft vessel to the receiving blood vessel.

5. An anastomosis apparatus as claimed in claim 1, wherein the attachment means is a suturing device.

6. An anastomosis apparatus as claimed in claim 1, wherein the attachment means is a clipping device.

7. An anastomosis apparatus as claimed in claim 1, wherein the attachment means is a device for radiation welding.

8. An anastomosis apparatus as claimed in claim 1, wherein the attachment means is a device for laser sealing.

9. An anastomosis apparatus as claimed in claim 1, wherein the attachment means is a device for soldering.

10. An anastomosis apparatus as claimed in claim 1, wherein the attachment means is a device for gluing.

11. An anastomosis apparatus as claimed in claim 1, wherein the centering means is a centering core.

12. An anastomosis apparatus as claimed in claim 1, wherein the centering means is a conduit in the cutting means.

13. An anastomosis apparatus as claimed in claim 1, wherein the centering means is a tube.

14. An anastomosis apparatus for use with an intraluminally directed anvil apparatus, the anastomosis apparatus comprising:
    an attachment device configured to attach an end of a graft vessel to wall of a receiving blood vessel;
    a centering core located within the attachment device and having a conduit configured to receive a piercing wire extending from an anvil of an intraluminally directed anvil apparatus such that the anastomosis apparatus can be centered over anastomosis site and engage the piercing wire to enable the wall of the receiving blood vessel to be moved as needed at the anastomosis site as the intraluminally directed anvil apparatus is moved via the anastomosis apparatus; and
    a cutter that is coaxial with the centering core and that is adapted to engage the anvil of the intraluminally directed anvil apparatus after the centering core has received and engaged the piercing wire wherein the cutter is configured to form a generally cylindrical opening in the wall of the receiving blood vessel at the anastomosis site that generally corresponds with the circumference of the end of the graft vessel and is centered on the piercing wire.

15. An anastomosis apparatus as claimed in claim 14, wherein the attachment device is a staple delivery device.

16. An anastomosis apparatus as claimed in claim 14, wherein the attachment device is a suturing device.

17. An anastomosis apparatus as claimed in claim 14, wherein the attachment device is a clipping device.

18. An anastomosis apparatus as claimed in claim 14, wherein the attachment device is a device for radiation welding.

19. An anastomosis apparatus as claimed in claim 14, wherein the attachment device is a device for laser sealing.

20. An anastomosis apparatus as claimed in claim 14, wherein the attachment device is a device for soldering.

21. An anastomosis apparatus as claimed in claim 14, wherein the attachment device is a device for gluing.

22. An anastomosis apparatus for use with an intraluminally directed anvil apparatus, the anastomosis apparatus comprising:
    an attachment device configured to attach an end of a graft vessel to a wall of a receiving blood vessel; and
    a cutter located within the attachment device that is adapted to engage an anvil of the intraluminally directed anvil apparatus and that is configured to form an opening in the wall of a receiving blood vessel at an anastomosis site that is generally cylindrical and generally corresponds with the circumference of the end of the graft vessel;
    wherein the cutter has a centering conduit centrally and coaxilly located within the cutter which is configured to receive a piercing wire extending from the anvil of the intraluminally directed anvil apparatus such that the anastomosis apparatus can be centered over the anastomosis site to enable the opening to be centered on the piercing wire, wherein the centering conduit is configured to enable the piercing wire to be engaged such that the wall of the receiving blood vessel may be moved as needed as the intraluminally directed anvil apparatus is moved via the anastomosis apparatus.

23. An anastomosis apparatus as claimed in claim 22, wherein the attachment device is a staple delivery device.

24. An anastomosis apparatus as claimed in claim 22, wherein the attachment device is a suturing device.

25. An anastomosis apparatus as claimed in claim 22, wherein the attachment device is a clipping device.

26. An anastomosis apparatus as claimed in claim 22, wherein the attachment device is a device for radiation welding.

27. An anastomosis apparatus as claimed in claim 22, wherein the attachment device is a device for laser sealing.

28. An anastomosis apparatus as claimed in claim 22, wherein the attachment device is a device for soldering.

29. An anastomosis apparatus as claimed in claim 22, wherein the attachment device is a device for gluing.

30. An anastomosis apparatus for use with an intraluminally directed anvil apparatus, the anastomosis apparatus comprising:
    centering means for centering the anastomosis apparatus over an anastomosis site by receiving a piercing wire extending from an anvil of an intraluminally directed anvil apparatus and then engaging the piercing wire to enable a wall of a receiving blood vessel to be moved as needed at the anastomosis site as the intraluminally directed anvil apparatus is moved via the anastomosis apparatus;
    cutting means for forming an opening in the wall of the receiving blood vessel at the anastomosis site through engagement with the anvil of the intraluminally directed anvil apparatus after the centering means has received and engaged the piercing wire, such that the opening is generally cylindrical, generally corresponds with the circumference of an end of a graft vessel and is centered on the piercing wire;
    anastomosis ring means for maintaining the end of the graft vessel in a desired position; and
    staple delivery means for delivering staples through the end of the graft vessel, through the receiving blood vessel around the opening in the receiving blood vessel and through the anastomosis ring means.

31. An anastomosis apparatus as recited in claim 30, wherein the cutting means is a cutter.

32. An anastomosis apparatus as recited in claim 30, wherein the cutting means is a device that delivers radiation.

33. An anastomosis apparatus as recited in claim 30, wherein the anastomosis ring means is a circumferential anastomosis ring.

34. An anastomosis apparatus as recited in claim 30, wherein the anastomosis ring means is a permanent anastomosis ring.

35. An anastomosis apparatus as recited in claim 30, wherein the anastomosis ring means is a biocompatible dissolvable anastomosis ring.

36. An anastomosis apparatus as recited in claim 30, wherein the anastomosis ring means is a removable anastomosis ring.

37. An anastomosis apparatus as recited in claim 30, wherein the anastomosis ring means is an anastomosis ring preloaded with staples.

38. An anastomosis apparatus as recited in claim 30, wherein the centering means is a centering core.

39. An anastomosis apparatus as recited in claim 30, wherein the centering means is a centering conduit in the cutting means.

40. An anastomosis apparatus as recited in claim 30, wherein the centering means is a tube.

41. An anastomosis apparatus for use with an intraluminally directed anvil apparatus, the anastomosis apparatus comprising:

centering means for centering the anastomosis apparatus over an anastomosis site by receiving a piercing wire extending from an anvil of an intraluminally directed anvil apparatus and then engaging the piercing wire to enable a wall of a receiving blood vessel to be moved as needed at the anastomosis site as the intraluminally directed anvil apparatus is moved via the anastomosis apparatus;

cutting means for forming an opening in the wall of the receiving blood vessel at the anastomosis site through engagement with the anvil of the intraluminally directed anvil apparatus after the centering means has received and engaged the piercing wire, such that the opening is generally cylindrical, generally corresponds with the circumference of an end of a graft vessel and is centered on the piercing wire; and means for clipping an end of the graft vessel to the wall of the receiving blood vessel.

42. An anastomosis apparatus for use with an intraluminally directed anvil apparatus, the anastomosis apparatus comprising:

centering means for centering the anastomosis apparatus over an anastomosis site by receiving a piercing wire extending from an anvil of an intraluminally directed anvil apparatus and then engaging the piercing wire to enable a wall of a receiving blood vessel to be moved as needed at the anastomosis site as the intraluminally directed anvil apparatus is moved via the anastomosis apparatus.

cutting means for forming an opening in the wall of the receiving blood vessel at the anastomosis site through engagement with the anvil of the intraluminally directed anvil apparatus after the centering means has received and engaged the piercing wire, such that the opening is generally cylindrical, generally corresponds with the circumference of an end of a graft vessel and is centered on the piercing wire; and means for suturing an end of the graft vessel to the wall of the receiving blood vessel.

43. An anastomosis apparatus for use with an intraluminally directed anvil apparatus, the anastomosis apparatus comprising:

centering means for centering the anastomosis apparatus over an anastomosis site by receiving a piercing extending from an anvil of an intraluminally directed anvil apparatus and then engaging the piercing to enable a wall of a receiving blood vessel to be moved as needed at the anastomosis site as the intraluminally directed anvil apparatus is moved via the ansastomosis apparatus;

cutting means for forming an opening in the wall of the receiving blood vessel at the anastomosis site through engagement with the anvil of the intraluminally directed anvil apparatus after the centering means has received and engaged the the piercing wire, such that the opening is generally cylindrical, generally corresponds with the circumference of an end of a graft vessel and is centered on the piercing wire; and means for radiation welding an end of the graft vessel to the wall of the receiving blood vessel.

44. An anastomosis apparatus for use with an intraluminally directed anvil apparatus, the anastomosis apparatus comprising:

centering means for centering the anastomosis apparatus over an anastomosis site by receiving a piercing wire extending from an anvil of an intraluminally directed anvil apparatus and then engaging the piercing wire to enable a wall of a receiving blood vessel to be moved as needed at the anastomosis site as the intraluminally directed anvil apparatus is moved via the anastomosis apparatus;

cutting means for forming an opening in the wall of the receiving blood vessel at the anastomosis site through engagement with the anvil of the intraluminally directed anvil apparatus after the centering means has received and engaged the piercing wire, such that the opening is generally cylindrical, generally corresponds with the circumference of an end of a graft vessel and is centered on the piercing wire; and means for laser sealing an end of the graft vessel to the wall of the receiving blood vessel.

45. An anastomosis apparatus for use with an intraluminally directed anvil apparatus, the anastomosis apparatus comprising:

centering means for centering the anastomosis apparatus over an anastomosis site by receiving a piercing wire extending from an anvil of an intraluminally directed anvil apparatus and then engaging the piercing wire to enable a wall of a receiving blood vessel to be moved as needed at the anastomosis site as the intraluminally directed anvil apparatus is moved via the anastomosis apparatus;

cutting means for forming an opening in the wall of the receiving blood vessel at the anastomosis site through engagement with the anvil of the intraluminally directed anvil apparatus after the centering means has received and engaged the piercing wire, such that the opening is generally cylindrical, generally corresponds with the circumference of an end of a graft vessel and is centered on the piercing wire; and means for soldering an end of the graft vessel to the wall of the receiving blood vessel.

46. An anastomosis apparatus for use with an intraluminally directed anvil apparatus, the anastomosis apparatus comprising:

centering means for centering the anastomosis apparatus over an anastomosis site by receiving a piercing wire extending from an anvil of an intraluminally directed anvil apparatus and then engaging the piercing wire to enable a wall of a receiving blood vessel to be moved as needed at the anastomosis site as the intraluminally directed anvil apparatus is moved via the anastomosis apparatus;

cutting means for forming an opening in the wall of the receiving blood vessel at the anastomosis site through engagement with the anvil of the intraluminally directed anvil apparatus after the centering means has received and engaged the piercing wire, such that the opening is generally cylindrical, generally corresponds with the circumference of an end of a graft vessel and is centered on the piercing wire; and means for gluing an end of the graft vessel to the wall of the receiving blood vessel.

47. An anastomosis apparatus for use with an intraluminally directed anvil apparatus, the anastomosis apparatus comprising:

an anastomosis ring having a plurality of pairs of staple prong passages extending from an outer wall to an inner wall;

a staple delivery device configured to deliver staples through staple prong passages of the anastomosis ring to attach an end of a graft vessel to a wall of a receiving blood vessel;

a centering core located within the staple delivery device and having a conduit configured to receive a piercing wire extending from an anvil of an intraluminally directed anvil apparatus such that the anastomosis apparatus can be centered over the anastomosis site and such that the piercing wire can be engaged by a locking mechanism to enable the wall of the receiving blood vessel to be moved as needed at the anastomosis site as the intraluminally directed anvil apparatus is moved via the anastomosis apparatus; and a cutter that is coaxial with the centering core and that is adapted to engage the anvil of the intraluminally directed anvil apparatus after the piercing wire has been received and engaged, wherein the cutter is configured to form a generally cylindrical opening in the wall of the receiving blood vessel at the anastomosis site that generally corresponds with the circumference of the end of the graft vessel and is centered on the piercing wire.

48. An anastomosis apparatus for use with an intraluminally directed anvil apparatus, the anastomosis apparatus comprising:

a suturing device configured to attach an end of a graft vessel to the wall of the receiving blood vessel;

a centering core located within the suturing device and having a conduit configured to receive a piercing wire extending from an anvil of an intraluminally directed anvil apparatus such that the anastomosis apparatus can be centered over the anastomosis site and such that the piercing wire can be engaged by a locking mechanism to enable the wall of the receiving blood vessel to be moved as needed at the anastomosis site as the intraluminally directed anvil apparatus is moved via the anastomosis apparatus; and a cutter that is coaxial with the centering core and that is adapted to engage the anvil of the intraluminally directed anvil apparatus after the piercing wire has been received and engaged, wherein the cutter is configured to form a generally cylindrical opening in the wall of the receiving blood vessel at the anastomosis site that generally corresponds with the circumference of the end of the graft vessel and is centered on the piercing wire.

49. An anastomosis apparatus for use with an intraluminally directed anvil apparatus, the anastomosis apparatus comprising:

a clipping device configured to attach an end of a graft vessel to the wall of the receiving blood vessel;

a centering core located within the clipping device and having a conduit configured to receive a piercing wire extending from an anvil of an intraluminally directed anvil apparatus such that the anastomosis apparatus can be centered over the anastomosis site and such that the piercing wire can be engaged by a locking mechanism to enable the wall of the receiving blood vessel to be moved as needed at the anastomosis site as the intraluminally directed anvil apparatus is moved via the anastomosis apparatus; and a cutter that is coaxial with the centering core and that is adapted to engage the anvil of the intraluminally directed anvil apparatus after the piercing wire has been received and engaged, wherein the cutter is configured to form a generally cylindrical opening in the wall of the receiving blood vessel at the anastomosis site that generally corresponds with the circumference of the end of the graft vessel and is centered on the piercing wire.

50. An anastomosis apparatus for use with an intraluminally directed anvil apparatus, the anastomosis apparatus comprising:

a device for radiation welding configured to attach an end of a graft vessel to the wall of the receiving blood vessel;

a centering core located within the radition welding device and having a conduit configured to receive a piercing wire extending from an anvil of an intraluminally directed anvil apparatus such that the anastomosis apparatus can be centered over the anastomosis site and such that the piercing wire can be engaged by a locking mechanism to enable the wall of the receiving blood vessel to be moved as needed at the anastomosis site as the intraluminally directed anvil apparatus is moved via the anastomosis apparatus; and a cutter that is coaxial with the centering core and that is adapted to engage the anvil of the intraluminally directed anvil apparatus after the piercing wire has been received and engaged, wherein the cutter is configured to form a generally cylindrical opening in the wall of the receiving blood vessel at the anastomosis site that generally corresponds with the circumference of the end of the graft vessel and is centered on the piercing wire.

51. An anastomosis apparatus for use with an intraluminally directed anvil apparatus, the anastomosis apparatus comprising:

a device for laser sealing configured to attach an end of a graft vessel to the wall of the receiving blood vessel;

a centering core located within the laser sealing device and having a conduit configured to receive a piercing wire extending from an anvil of an intraluminally directed anvil apparatus such that the anastomosis apparatus can be centered over the anastomosis site and such that the piercing wire can be engaged by a locking mechanism to enable the wall of the receiving blood vessel to be moved as needed at the anastomosis site as the intraluminally directed anvil apparatus is moved via the anastomosis apparatus; and a cutter that is coaxial with the centering core and that is adapted to engage the anvil of the intraluminally directed anvil apparatus after the piercing wire has been received and engaged, wherein the cutter is configured to form a generally cylindrical opening in the wall of the receiving blood vessel at the anastomosis site that generally corresponds with the circumference of the end of the graft vessel and is centered on the piercing wire.

52. An anastomosis apparatus for use with an intraluminally directed anvil apparatus, the anastomosis apparatus comprising:
- a device for soldering configured to attach an end of a graft vessel to the wall of the receiving blood vessel;
- a centering core located within the soldering device and having a conduit configured to receive a piercing wire extending from an anvil of an intraluminally directed anvil apparatus such that the anastomosis apparatus can be centered over the anastomosis site and such that the piercing wire can be engaged by a locking mechanism to enable the wall of the receiving blood vessel to be moved as needed at the anastomosis site as the intraluminally directed anvil apparatus is moved via the anastomosis apparatus; and
- a cutter that is coaxial with the centering core and that is adapted to engage the anvil of the intraluminally directed anvil apparatus after the piercing wire has been received and engaged, wherein the cutter is configured to form a generally cylindrical opening in the wall of the receiving blood vessel at the anastomosis site that generally corresponds with the circumference of the end of the graft vessel and is centered on the piercing wire.

53. An anastomosis apparatus for use with an intraluminally directed anvil apparatus, the anastomosis apparatus comprising:
- a device for gluing configured to attach an end of a graft vessel to the wall of the receiving blood vessel;
- a centering core located within the gluing device and having a conduit configured to receive a piercing wire extending from an anvil of an intraluminally directed anvil apparatus such that the anastomosis apparatus can be centered over the anastomosis site and such that the piercing wire can be engaged by a locking mechanism to enable the wall of the receiving blood vessel to be moved as needed at the anastomosis site as the intraluminally directed anvil apparatus is moved via the anastomosis apparatus; and
- a cutter that is coaxial with the centering core and that is adapted to engage the anvil of the intraluminally directed anvil apparatus after the piercing wire has been received and engaged, wherein the cutter is configured to form a generally cylindrical opening in the wall of the receiving blood vessel at the anastomosis site that generally corresponds with the circumference of the end of the graft vessel and is centered on the piercing wire.

54. An anastomosis apparatus for use with an intraluminally directed anvil apparatus, the anastomosis apparatus comprising:
- centering means for centering the anastomosis apparatus over an anastomosis site by receiving a piercing wire extending from an anvil of an intraluminally directed anvil apparatus such that the piercing wire can be engaged to enable a wall of the receiving blood vessel to be moved as needed at the anastomosis site as the intraluminally directed anvil apparatus is moved via the anastomosis apparatus; and
- cutting means for forming an opening in the wall of the receiving blood vessel at an anastomosis site through engagement with an anvil of the intraluminally directed anvil apparatus after the centering means has received and engaged the piercing wire, such that the opening is generally cylindrical, generally corresponds with the circumference of the end of the graft vessel and is centered on the piercing wire;
- anastomosis ring means for maintaining the end of the graft vessel in a desired position;
- staple engaging means for engaging staples positioned around the opening in the wall of the receiving blood vessel; and
- activation means for acting on the staple engaging means to enable the staple engaging means to push the staples through the end of the graft vessel, through the receiving blood vessel around the opening in the receiving blood vessel and through the anastomosis ring means.

55. An anastomosis apparatus as recited in claim 54, wherein the cutting means is a cutter.

56. An anastomosis apparatus as recited in claim 54, wherein the cutting means is a device that delivers radiation.

57. An anastomosis apparatus as recited in claim 54, wherein the anastomosis ring means is a permanent anastomosis ring.

58. An anastomosis apparatus as recited in claim 54, wherein the anastomosis ring means is a biocompatible dissolvable anastomosis ring.

59. An anastomosis apparatus as recited in claim 54, wherein the anastomosis ring means is a removable anastomosis ring.

60. An anastomosis apparatus as recited in claim 54, wherein the anastomosis ring means is a pre-loaded anastomosis ring.

61. An anastomosis apparatus as recited in claim 54, wherein the centering means is a centering core.

62. An anastomosis apparatus as recited in claim 54, wherein the centering means is a centering conduit in the cutting means.

63. An anastomosis apparatus as recited in claim 54, wherein the centering means is a tube.

64. An anastomosis apparatus as recited in claim 54, wherein the staple engaging means is a staple pushing device.

65. An anastomosis apparatus as recited in claim 54, wherein the activation means is an activation sheath.

66. An anastomosis apparatus for use with an intraluminally directed anvil apparatus, the anastomosis apparatus comprising:
- centering means for centering the anastomosis apparatus over an anastomosis site by receiving a piercing wire extending from an anvil of an intraluminally directed anvil apparatus such that the piercing wire can be engaged to enable a wall of the receiving blood vessel to be moved as needed at the anastomosis site as the intraluminally directed anvil apparatus is moved via the anastomosis apparatus; and
- cutting means for forming an opening in the wall of the receiving blood vessel at an anastomosis site through engagement with an anvil of the intraluminally directed anvil apparatus after the centering means has received and engaged the piercing wire, such that the opening is generally cylindrical, generally corresponds with the circumference of the end of the graft vessel and is centered on the piercing wire;
- anastomosis ring means for maintaining the end of the graft vessel in a desired position;
- staple guide means for guiding staples into the anastomosis ring means, the staple guide means being coaxially disposed around the anastomosis ring means;
- staple engaging means for engaging the staples; and
- activation means for acting on the staple engaging means to enable the staple engaging means to push the staples through the end of the graft vessel, through the receiving blood vessel and through the anastomosis ring means.

67. An anastomosis apparatus as recited in claim 66, wherein the cutting means is a cutter.

68. An anastomosis apparatus as recited in claim 66, wherein the cutting means is a device that delivers radiation.

69. An anastomosis apparatus as recited in claim 66, wherein the anastomosis ring means is a permanent anastomosis ring.

70. An anastomosis apparatus as recited in claim 66, wherein the anastomosis ring means is a biocompatible dissolvable anastomosis ring.

71. An anastomosis apparatus as recited in claim 66, wherein the anastomosis ring means is a removable anastomosis ring.

72. An anastomosis apparatus as recited in claim 66, wherein the anastomosis ring means is a pre-loaded anastomosis ring.

73. An anastomosis apparatus as recited in claim 66, wherein the centering means is a centering core.

74. An anastomosis apparatus as recited in claim 66, wherein the centering means is a centering conduit in the cutting means.

75. An anastomosis apparatus as recited in claim 66, wherein the centering means a tube.

76. An anastomosis apparatus as recited in claim 66, wherein the staple engaging means is a staple engaging device.

77. An anastomosis apparatus as recited in claim 66, wherein the activation means is an activation sheath.

78. An anastomosis apparatus for use with an intraluminally directed anvil apparatus, the anastomosis apparatus comprising:

an anastomosis ring having a plurality of pairs of staple prong passages extending from an outer wall to an inner wall;

a staple guide ring coaxially disposed around the anastomosis ring, the staple guide having a plurality of staple grooves aligned with a pair of passages in the anastomosis ring such that a staple can be pushed along within the grooves and into the pair of passages in the anastomosis ring, a plurality of staples, each staple being positioned to be pushed through a groove in the staple guide ring and into a pair of passages in the anastomosis ring;

a centering core coaxially positioned within the anastomosis ring, the centering core having a centrally and longitudinally located conduit configured to receive a piercing wire extending from an anvil of an intraluminally directed anvil apparatus such that the anastomosis apparatus can be centered over an anastomosis site and such that the piercing wire can be enraged by a locking mechanism of the centering core to enable a wall of the receiving blood vessel to be moved as needed at the anastomosis site as the intraluminally directed anvil apparatus is moved via the anastomosis apparatus; and a cutter coaxially disposed around the centering core and having a distal cutting end opposite a proximal end, wherein the cutter is adapted to engage the anvil of the intraluminally directed anvil apparatus after the piercing wire has been received and engaged, wherein the cutter is configured to form a generally cylindrical opening in the wall of the receiving blood vessel at the anastomosis site that generally corresponds with the circumference of the end of the graft vessel and is centered on the piercing wire;

a staple engaging device coaxially disposed around the cutter and having a plurality of staple pushing arms, each staple pushing arm having a proximal end opposite a distal pushing end positioned in contact with a staple; and an activation sheath coaxially disposed around the staple engaging device and being configured to slide on the staple pushing device such that the sheath can slide from the proximal ends of the staple pushing arms downward to force the pushing ends of the pushing arms against the staples and then back up the staple engaging device to release the pushing arms, thereby enabling the staples to be pushed through the anastomosis ring and into an end of the graft vessel and the wall of the receiving blood vessel.

79. An anastomosis apparatus for use with with an intraluminally directed anvil apparatus, the anastomosis apparatus comprising:

an anastomosis ring having an inner wall opposite an outer wall, a retention side opposite a bottom side, and a plurality of pairs of staple prong passages extending from the outer wall to the inner wall such that each pair of passages can receive opposing prongs of a staple; the retention side of the anastomosis ring having a plurality of notches extending from the outer wall towards the inner wall;

a staple guide ring coaxially disposed around the anastomosis ring, the staple guide having an outer wall opposite an inner wall positioned adjacent to the outer wall of the anastomosis ring, a retention side opposite a bottom side, and a plurality of staple grooves extending through the retention side from the outer wall to the inner wall; each staple groove being aligned with a pair of passages in the anastomosis ring such that a staple can be pushed along within the grooves and into a pair of passages in the anastomosis ring, the retention side of the staple guide ring having a plurality of notches extending from the inner wall towards the outer wall, each notch being configured to align with a notch in the anastomosis ring to yield a plurality of retention slots;

a plurality of staples, each staple having a driving portion between opposing prongs, each pair of prongs of each staple being positioned at least partially within one of the pairs of passages in the anastomosis ring and within one of the staple grooves of the staple guide ring;

a centering core having a distal coupling end opposite a proximal control end, the centering core being configured and sized for coaxial movement through the anastomosis ring, the centering core having a centrally and longitudinally located conduit configured to receive a catheter wire, the centering core having a locking element to retain the catheter wire in a fixed position within the conduit;

a cutter coaxially disposed around the centering core and having a distal cutting end opposite a proximal end;

a staple pushing device coaxially disposed around the cutter and having a plurality of staple pushing arms and a plurality of retention arms, each staple pushing arm having a distal pushing end opposite a proximal end, each retention arm having a retention end opposite a proximal end, the retention ends being positioned within the retention slots defined by the notches in the anastomosis ring and the staple guide ring, each staple pushing end being positioned in contact with a driving portion of a staple; and an activation sheath coaxially disposed around the staple pushing device and being configured to slide on the staple pushing device such that the sheath can slide from the proximal ends of the staple pushing arms and the retention arms downward to force the pushing ends of the pushing arms against the driving portions of the staples and then back up the staple pushing device to release the pushing arms, thereby enabling the staples to be pushed through the anastomosis ring and into an end of the graft vessel and the wall of the receiving blood vessel.

* * * * *

UNITED STATES PATENT AND TRADEMARK OFFICE
CERTIFICATE OF CORRECTION

| | |
|---|---|
| PATENT NO. | : 6,248,117 B1 |
| APPLICATION NO. | : 09/293617 |
| DATED | : June 19, 2001 |
| INVENTOR(S) | : Duane D. Blatter |

It is certified that error appears in the above-identified patent and that said Letters Patent is hereby corrected as shown below:

The name of the Assignee should be "Vital Access Corporation, Salt Lake City, UT (US)" pursuant to a Merger Agreement recorded on February 5, 2008, at Reel 020462, Frame 0595

Column 8, line 60—the word "stapled" should be capitalized.

Column 9, line 5—the name "Nonnan" Rich should be changed to "Norman" Rich.

Column 10, line 15—the word "stapled" should be capitalized.

Column 11, line 41—the name "Sanbom" should read "Sanborn"; line 51—the word "laser" should be capitalized.

Column 13, line 18—the word "low" should be capitalized.

Column 19, line 48—"logitudinal" should be spelled "longitudinal."

Column 24, line 44—should have a --.-- at the end of the sentence.

Column 30, line 33—"bioabsorvable" should be spelled "bioabsorbable."

Column 37, line 53—the word "laser" should be capitalized.

Column 40, line 62—the word "laser" should be capitalized.

Column 41, line 35—"anastmosis" should be spelled "anastomosis."

Column 42, line 16—the word --deliver-- should be inserted between the words "that" and "radiation."

Signed and Sealed this
Thirtieth Day of August, 2011

David J. Kappos
*Director of the United States Patent and Trademark Office*

Column 46, line 34—"united states" should read "United States."

Column 47, line 23—the word --a-- should be inserted between the words "to" and "wall"; line 28—the word --an-- should be inserted between the words "over" and "anastomosis."

Column 49, lines 61-62—the word --wire-- should be inserted between the words "piercing" and "extending"; line 63—the word "wire" should be placed between the words "piercing" and "to."

Column 50, line 5—delete the extra word "the."

Column 52, line 24—"radition" should be spelled "radiation."

Column 54, line 66— --around the opening in the receiving blood vessel-- should be inserted between the words "vessel" and "and."

Column 55, line 23—the word --is-- should be inserted between the words "means" and "a"; line 51—the word "enraged" should read "engaged."